(12) United States Patent
Delcayre et al.

(10) Patent No.: US 7,914,792 B2
(45) Date of Patent: Mar. 29, 2011

(54) METHODS AND COMPOUNDS FOR RAISING ANTIBODIES AND FOR SCREENING ANTIBODY REPERTOIRES

(75) Inventors: Alain Delcayre, San Jose, CA (US); Jean-Bernard Le Pecq, Menlo Park, CA (US)

(73) Assignee: Exothera L.L.C., Menlo Park, CA (US)

( * ) Notice: Subject to any disclaimer, the term of this patent is extended or adjusted under 35 U.S.C. 154(b) by 750 days.

(21) Appl. No.: 10/545,557

(22) PCT Filed: Feb. 13, 2004

(86) PCT No.: PCT/IB2004/000888
§ 371 (c)(1), (2), (4) Date: Nov. 18, 2005

(87) PCT Pub. No.: WO2004/073319
PCT Pub. Date: Aug. 26, 2004

(65) Prior Publication Data
US 2006/0222654 A1 Oct. 5, 2006

Related U.S. Application Data

(60) Provisional application No. 60/447,291, filed on Feb. 14, 2003.

(51) Int. Cl.
*A61K 39/00* (2006.01)
*C12P 21/04* (2006.01)

(52) U.S. Cl. .................................. 424/184.1; 435/70.1
(58) Field of Classification Search ............... 424/184.1; 435/70.1
See application file for complete search history.

(56) References Cited

U.S. PATENT DOCUMENTS

| | | | | |
|---|---|---|---|---|
| 5,688,936 A | * | 11/1997 | Edwards | ............ 536/23.5 |
| 2004/0197314 A1 | * | 10/2004 | Delcayre et al. | ............ 424/93.21 |

FOREIGN PATENT DOCUMENTS

| | | |
|---|---|---|
| EP | 1 004 664 A | 5/2000 |
| WO | 97/05900 | 2/1997 |
| WO | 98/10749 | 3/1998 |
| WO | WO 00/28001 A | 5/2000 |
| WO | 01/82958 | 11/2001 |
| WO | 02/00729 | 1/2002 |
| WO | 02/056831 | 7/2002 |
| WO | 03/016522 | 2/2003 |
| WO | 03/076603 | 9/2003 |

OTHER PUBLICATIONS

Scholnick et al (Trends in Biotechnology, 18(1):34-39, 2000).*
Burgess et al, Journal of Cell Biology vol. 111 Nov. 1990 2129-2138.*
Lazar et al Molecular and Cellular Biology Mar. 1988 vol. 8 No. 3 1247-1252.*
Pietravalle et al. (Eur. J. Immunol. 26(3):725-728 (1996) Abstract only).*
Thery et al; "Molecular Characterization of Dendritic Cell-Derived Exosomes, Selective Accumulation of the Heat Shock Protein HSC73"; The Journal of Cell Biology, Rockefeller University Press, US, vol. 147, No. 3, Nov. 1, 1999, pp. 599-610, XP000918507.
Oshima et al; "Secretion of a Peripheral Membrane Protein, MFG-E8, As a Complex With Membrane Vesicles"; European Journal of Biochemistry/FEBS., Germany, Feb. 2002, vol. 269, No. 4, pp. 1209-1218, XP002233407.
Andersen et al, *Functional Analysis of Two Cellular Binding Domains of Bovine Lactadherin*, Biochemistry, vol. 39, No. 20, May 23, 2000, pp. 6200-6206, XP000917941.
Le Pecq & Delcayre Declaration Under Rule 132 executed Mar. 26, 2008 in U.S. Appl. No. 10/485,360, filed May 24, 2010.
Le Pecq & Delcayre Declaration Under Rule 132 executed May 18, 2010 and filed May 24, 2010.
Delcayre et al, "Exosomes as novel therapeutic nanodevices" Current Opinions in Molecular Therapeutics 2006 8(1):31-36.
Thery et al, "Molecular Characterization of Dendritic Cell-derived Exosomes: Selective Accumulation of the Heat Shock Protein hsc73" The Journal of Cell Biology, vol. 147, No. 3, Nov. 1, 1999, 599-610.

* cited by examiner

*Primary Examiner* — Lynn Bristol
(74) *Attorney, Agent, or Firm* — Nixon & Vanderhye P.C.

(57) ABSTRACT

The present invention relates to compositions and methods for raising antibodies generally comprising 1) providing highly immunogenic vesicles bearing at least one target antigen and 2) immunizing animals with the said antigen-bearing vesicles to induce antigen-specific antibody responses. The invention also relates to methods of screening antibody repertoires comprising 1) providing vesicles bearing at least one target antigen and one marker and 2) isolating antibody-producing cells or particles with defined antigen specificity using the said antigen- and marker-bearing vesicles. Antibodies with defined antigen specificity can then be prepared from isolated antibody-producing cells using known methods of the art. This invention can be used in experimental, research, therapeutic, prophylactic or diagnostic areas.

32 Claims, 16 Drawing Sheets

Figure 1:
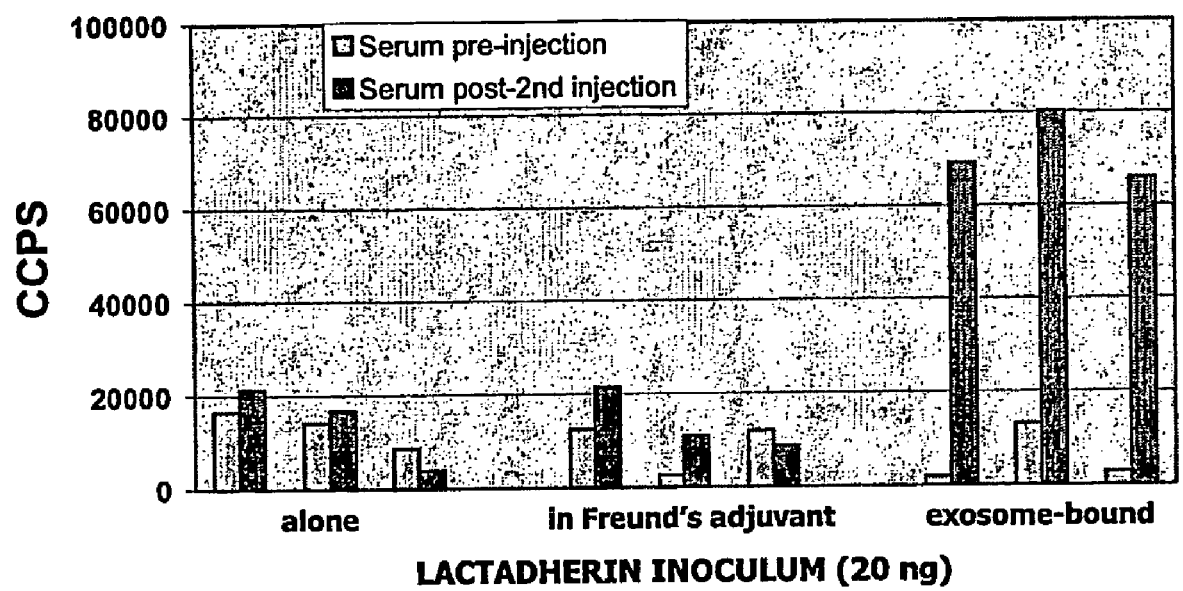

ELISA detecting anti-Lactadherin antibody in sera of Lactadherin-immunized mice

FACS analysis of recombinant cells transfected with HApC3.1/SSTR2 and labelled with anti-HA tag antibody Western blot analysis detecting HA-SSTR2 expressed in exosomes produced by HApC3.1/SSTR2-transfected cells FACS analysis of a panel of 293 cells transfected with various GPCR-encoding HApC3.1 and labelled with anti-HA tag antibody Capture-ELISA detecting HA-GPCR expression on exosomes derived from a panel of 293 cells transfected with various GPCR-encoding HApC3.1

Capture ELISA detecting HLA-A2 and β2-microglobulin expression on 293 exosomes

Capture-ELISA detecting Reference peptide bound to HLA-A2 on exosomes

Western Blot analysis detecting the expression of CD40L and mutCD40L on recombinant 293 exosomes DC-maturation assay measuring the biological activity of recombinant exosomes displaying CD40L Measurement of fluorescence associated with recombinant exosome expressing GFP/C1C2 chimeric protein 293 Exosomes Capture ELISA detecting fluorescence associated with exosomes derived from cells metabolically labelled with Rh-DOPE FACS analysis detecting PLNC bearing GFP/CCR7-293 exosomes FACS analysis detecting PLNC bearing GFP/A2/MART1-293 exosomes Gel analysis of single cell-derived RT-PCR products Capture-ELISA detecting recombinant IgG M90/12 in CHO-culture supernatants FACS analysis of AbTrap- and + cells incubated with biotinylated exosomes

SEQUENCE LISTING

```
<160> NUMBER OF SEQ ID NOS: 86

<210> SEQ ID NO 1
<211> LENGTH: 434
<212> TYPE: PRT
<213> ORGANISM: artificial sequence
<220> FEATURE:
<223> OTHER INFORMATION: mouse lactadherin + His Tag

<400> SEQUENCE: 1

Met Gln Val Ser Arg Val Leu Ala Ala Leu Cys Gly Met Leu Leu Cys
1               5                   10                  15

Ala Ser Gly Leu Phe Ala Ala Ser Gly Asp Phe Cys Asp Ser Ser Leu
            20                  25                  30

Cys Leu Asn Gly Gly Thr Cys Leu Thr Gly Gln Asp Asn Asp Ile Tyr
        35                  40                  45

Cys Leu Cys Pro Glu Gly Phe Thr Gly Leu Val Cys Asn Glu Thr Glu
    50                  55                  60

Arg Gly Pro Cys Ser Pro Asn Pro Cys Tyr Asn Asp Ala Lys Cys Leu
65                  70                  75                  80

Val Thr Leu Asp Thr Gln Arg Gly Asp Ile Phe Thr Glu Tyr Ile Cys
                85                  90                  95

Gln Cys Pro Val Gly Tyr Ser Gly Ile His Cys Glu Thr Gly Cys Ser
```

```
                    100                 105                 110
Thr Gln Leu Gly Met Glu Gly Gly Ala Ile Ala Asp Ser Gln Ile Ser
            115                 120                 125
Ala Ser Tyr Val Tyr Met Gly Phe Met Gly Leu Gln Arg Trp Gly Pro
        130                 135                 140
Glu Leu Ala Arg Leu Tyr Arg Thr Gly Ile Val Asn Ala Trp His Ala
145                 150                 155                 160
Ser Asn Tyr Asp Ser Lys Pro Trp Ile Gln Val Asn Leu Leu Arg Lys
                165                 170                 175
Met Arg Val Ser Gly Val Met Thr Gln Gly Ala Ser Arg Ala Gly Arg
            180                 185                 190
Ala Glu Tyr Leu Lys Thr Phe Lys Val Ala Tyr Ser Leu Asp Gly Arg
        195                 200                 205
Lys Phe Glu Phe Ile Gln Asp Glu Ser Gly Gly Asp Lys Glu Phe Leu
    210                 215                 220
Gly Asn Leu Asp Asn Asn Ser Leu Lys Val Asn Met Phe Asn Pro Thr
225                 230                 235                 240
Leu Glu Ala Gln Tyr Ile Arg Leu Tyr Pro Val Ser Cys His Arg Gly
                245                 250                 255
Cys Thr Leu Arg Phe Glu Leu Leu Gly Cys Glu Leu His Gly Cys Leu
            260                 265                 270
Glu Pro Leu Gly Leu Lys Asn Asn Thr Ile Pro Asp Ser Gln Met Ser
        275                 280                 285
Ala Ser Ser Ser Tyr Lys Thr Trp Asn Leu Arg Ala Phe Gly Trp Tyr
    290                 295                 300
Pro His Leu Gly Arg Leu Asp Asn Gln Gly Lys Ile Asn Ala Trp Thr
305                 310                 315                 320
Ala Gln Ser Asn Ser Ala Lys Glu Trp Leu Gln Val Asp Leu Gly Thr
                325                 330                 335
Gln Arg Gln Val Thr Gly Ile Ile Thr Gln Gly Ala Arg Asp Phe Gly
            340                 345                 350
His Ile Gln Tyr Val Glu Ser Tyr Lys Val Ala His Ser Asp Asp Gly
        355                 360                 365
Val Gln Trp Thr Val Tyr Glu Glu Gln Gly Ser Ser Lys Val Phe Gln
    370                 375                 380
Gly Asn Leu Asp Asn Asn Ser His Lys Lys Asn Ile Phe Glu Lys Pro
385                 390                 395                 400
Phe Met Ala Arg Tyr Val Arg Val Leu Pro Val Ser Trp His Asn Arg
                405                 410                 415
Ile Thr Leu Arg Leu Glu Leu Leu Gly Cys Thr Gly His His His His
            420                 425                 430
His His

<210> SEQ ID NO 2
<211> LENGTH: 1188
<212> TYPE: DNA
<213> ORGANISM: artificial sequence
<220> FEATURE:
<223> OTHER INFORMATION: human lactadherin + his tag

<400> SEQUENCE: 2
atgccgcgcc ccgcctgct  ggccgcgctg tgcggcgcgc tgctctgcgc ccccagcctc      60
ctcgtcgccc tggatatctg ttccaaaaac ccctgccaca acggtggttt atgcgaggag     120
atttcccaag aagtgcgagg agatgtcttc ccctcgtaca cctgcacgtg ccttaagggc     180
```

```
tacgcgggca accactgtga gacgaaatgt gtcgagccac tgggcatgga gaatgggaac    240
attgccaact cacagatcgc cgcctcatct gtgcgtgtga ccttcttggg tttgcagcat    300
tgggtcccgg agctggcccg cctgaaccgc gcaggcatgg tcaatgcctg acacccagc    360 agcaatgacg ataacccctg gatccaggtg aacctgctgc ggaggatgtg ggtaacaggt    420
gtggtgacgc agggtgccag ccgcttggcc agtcatgagt acctgaaggc cttcaaggtg    480
gcctacagcc ttaatggaca cgaattcgat ttcatccatg atgttaataa aaaacacaag    540
gagtttgtgg gtaactggaa caaaaacgcg gtgcatgtca acctgtttga ccccctgtg    600 gaggctcagt acgtgagatt gtaccccacg agctgccaca cggcctgcac tctgcgcttt    660
gagctactgg gctgtgagct gaacggatgc gccaatcccc tgggcctgaa gaataacagc    720
atccctgaca gcagatcac ggcctccagc agctacaaga cctggggctt gcatctcttc    780
agctggaacc cctcctatgc acggctggac aagcagggca acttcaacgc ctgggttgcg    840
gggagctacg gtaacgatca gtggctgcag gtggacctgg gctcctcgaa ggaggtgaca    900
ggcatcatca cccagggggc ccgtaacttt ggctctgtcc agtttgtggc atcctacaag    960
gttgcctaca gtaatgacag tgcgaactgg actgagtacc aggacccag gactggcagc    1020 agtaagatct tccctggcaa ctgggacaac cactcccaca gaagaacttt gtttgagacg    1080
cccatcctgg ctcgctatgt gcgcatcctg cctgtagcct ggcacaaccg catcgccctg    1140
cgcctggagc tgctgggctg taggcctcat catcaccatc accattga               1188

<210> SEQ ID NO 3
<211> LENGTH: 30
<212> TYPE: DNA
<213> ORGANISM: artificial sequence
<220> FEATURE:
<223> OTHER INFORMATION: primer

<400> SEQUENCE: 3
tataagctta gcatgccgcg cccccgcctg                                     30

<210> SEQ ID NO 4
<211> LENGTH: 21
<212> TYPE: DNA
<213> ORGANISM: artificial sequence
<220> FEATURE:
<223> OTHER INFORMATION: primer

<400> SEQUENCE: 4
ggattggcgc atccgttcag c                                              21

<210> SEQ ID NO 5
<211> LENGTH: 18
<212> TYPE: DNA
<213> ORGANISM: artificial sequence
<220> FEATURE:
<223> OTHER INFORMATION: primer

<400> SEQUENCE: 5
gccctggata tctgttcc                                                  18

<210> SEQ ID NO 6
<211> LENGTH: 30
<212> TYPE: DNA
<213> ORGANISM: artificial sequence
<220> FEATURE:
<223> OTHER INFORMATION: primer

<400> SEQUENCE: 6
```

```
ataaccggta cagcccagca gctccaggcg                                              30
```

<210> SEQ ID NO 7
<211> LENGTH: 30
<212> TYPE: DNA
<213> ORGANISM: artificial sequence
<220> FEATURE:
<223> OTHER INFORMATION: primer

<400> SEQUENCE: 7

```
tataagcttg acatggcgga tgagccactc                                              30
```

<210> SEQ ID NO 8
<211> LENGTH: 32
<212> TYPE: DNA
<213> ORGANISM: artificial sequence
<220> FEATURE:
<223> OTHER INFORMATION: primer

<400> SEQUENCE: 8

```
atagcggccg ctcagatact ggtttggagg tc                                           32
```

<210> SEQ ID NO 9
<211> LENGTH: 1143
<212> TYPE: DNA
<213> ORGANISM: artificial sequence
<220> FEATURE:
<223> OTHER INFORMATION: HApC3.1/SSTR2
<220> FEATURE:
<221> NAME/KEY: CDS
<222> LOCATION: (1)..(1143)
<223> OTHER INFORMATION: HApC3.1/SSTR2

<400> SEQUENCE: 9

```
atg tac cct tac gac gtg ccc gac tat gct aag ctt gac atg gcg gat              48
Met Tyr Pro Tyr Asp Val Pro Asp Tyr Ala Lys Leu Asp Met Ala Asp
1               5                   10                  15 gag cca ctc aat gga agc cac aca tgg cta tcc att cca ttt gac ctc              96
Glu Pro Leu Asn Gly Ser His Thr Trp Leu Ser Ile Pro Phe Asp Leu
            20                  25                  30 aat ggc tct gtg gtg tca acc aac acc tca aac cag aca gag ccg tac             144
Asn Gly Ser Val Val Ser Thr Asn Thr Ser Asn Gln Thr Glu Pro Tyr
        35                  40                  45 tat gac ctg aca agc aat gca gtc ctc aca ttc atc tat ttt gtg gtc             192
Tyr Asp Leu Thr Ser Asn Ala Val Leu Thr Phe Ile Tyr Phe Val Val
    50                  55                  60 tgc atc att ggg ttg tgt ggc aac aca ctt gtc att tat gtc atc ctc             240
Cys Ile Ile Gly Leu Cys Gly Asn Thr Leu Val Ile Tyr Val Ile Leu
65                  70                  75                  80 cgc tat gcc aag atg aag acc atc acc aac att tac atc ctc aac ctg             288
Arg Tyr Ala Lys Met Lys Thr Ile Thr Asn Ile Tyr Ile Leu Asn Leu
                85                  90                  95 gcc atc gca gat gag ctc ttc atg ctg ggt ctg cct ttc ttg gct atg             336
Ala Ile Ala Asp Glu Leu Phe Met Leu Gly Leu Pro Phe Leu Ala Met
            100                 105                 110 cag gtg gct ctg gtc cac tgg ccc ttt ggc aag gcc att tgc cgg gtg             384
Gln Val Ala Leu Val His Trp Pro Phe Gly Lys Ala Ile Cys Arg Val
        115                 120                 125 gtc atg act gtg gat ggc atc aat cag ttc acc agc atc ttc tgc ctg             432
Val Met Thr Val Asp Gly Ile Asn Gln Phe Thr Ser Ile Phe Cys Leu
    130                 135                 140 aca gtc atg agc atc gac cga tac ctg gct gtg gtc cac ccc atc aag             480
Thr Val Met Ser Ile Asp Arg Tyr Leu Ala Val Val His Pro Ile Lys
145                 150                 155                 160
```

```
tcg gcc aag tgg agg aga ccc cgg acg gcc aag atg atc acc atg gct    528
Ser Ala Lys Trp Arg Arg Pro Arg Thr Ala Lys Met Ile Thr Met Ala
            165                 170                 175 gtg tgg gga gtc tct ctg ctg gtc atc ttg ccc atc atg ata tat gct    576
Val Trp Gly Val Ser Leu Leu Val Ile Leu Pro Ile Met Ile Tyr Ala
        180                 185                 190 ggg ctc cgg agc aac cag tgg ggg aga agc agc tgc acc atc aac tgg    624
Gly Leu Arg Ser Asn Gln Trp Gly Arg Ser Ser Cys Thr Ile Asn Trp
                195                 200                 205 cca ggt gaa tct ggg gct tgg tac aca ggg ttc atc atc tac act ttc    672
Pro Gly Glu Ser Gly Ala Trp Tyr Thr Gly Phe Ile Ile Tyr Thr Phe
210                 215                 220 att ctg ggg ttc ctg gta ccc ctc acc atc atc tgt ctt tgc tac ctg    720
Ile Leu Gly Phe Leu Val Pro Leu Thr Ile Ile Cys Leu Cys Tyr Leu
225                 230                 235                 240 ttc att atc atc aag gtg aag tcc tct gga atc cga gtg ggc tcc tct    768
Phe Ile Ile Ile Lys Val Lys Ser Ser Gly Ile Arg Val Gly Ser Ser
                245                 250                 255 aag agg aag aag tct gag aag aag gtc acc cga atg gtg tcc atc gtg    816
Lys Arg Lys Lys Ser Glu Lys Lys Val Thr Arg Met Val Ser Ile Val
            260                 265                 270 gtg gct gtc ttc atc ttc tgc tgg ctt ccc ttc tac ata ttc aac gtt    864
Val Ala Val Phe Ile Phe Cys Trp Leu Pro Phe Tyr Ile Phe Asn Val
        275                 280                 285 tct tcc gtc tcc atg gcc atc agc ccc acc cca gcc ctt aaa ggc atg    912
Ser Ser Val Ser Met Ala Ile Ser Pro Thr Pro Ala Leu Lys Gly Met
    290                 295                 300 ttt gac ttt gtg gtg gtc ctc acc tat gct aac agc tgt gcc aac cct    960
Phe Asp Phe Val Val Val Leu Thr Tyr Ala Asn Ser Cys Ala Asn Pro
305                 310                 315                 320 atc cta tat gcc ttc ttg tct gac aac ttc aag aag agc ttc cag aat   1008
Ile Leu Tyr Ala Phe Leu Ser Asp Asn Phe Lys Lys Ser Phe Gln Asn
                325                 330                 335 gtc ctc tgc ttg gtc aag gtg agc ggc aca gat gat ggg gag cgg agt   1056
Val Leu Cys Leu Val Lys Val Ser Gly Thr Asp Asp Gly Glu Arg Ser
            340                 345                 350 gac agt aag cag gac aaa tcc cgg ctg aat gag acc acg gag acc cag   1104
Asp Ser Lys Gln Asp Lys Ser Arg Leu Asn Glu Thr Thr Glu Thr Gln
        355                 360                 365 agg acc ctc ctc aat gga gac ctc caa acc agt atc tga               1143
Arg Thr Leu Leu Asn Gly Asp Leu Gln Thr Ser Ile
    370                 375                 380

<210> SEQ ID NO 10
<211> LENGTH: 380
<212> TYPE: PRT
<213> ORGANISM: artificial sequence
<220> FEATURE:
<223> OTHER INFORMATION: HApC3.1/SSTR2

<400> SEQUENCE: 10

Met Tyr Pro Tyr Asp Val Pro Asp Tyr Ala Lys Leu Asp Met Ala Asp
1               5                   10                  15

Glu Pro Leu Asn Gly Ser His Thr Trp Leu Ser Ile Pro Phe Asp Leu
            20                  25                  30

Asn Gly Ser Val Val Ser Thr Asn Thr Ser Asn Gln Thr Glu Pro Tyr
        35                  40                  45

Tyr Asp Leu Thr Ser Asn Ala Val Leu Thr Phe Ile Tyr Phe Val Val
    50                  55                  60

Cys Ile Ile Gly Leu Cys Gly Asn Thr Leu Val Ile Tyr Val Ile Leu
65                  70                  75                  80
```

Arg Tyr Ala Lys Met Lys Thr Ile Thr Asn Ile Tyr Ile Leu Asn Leu
            85                  90                  95

Ala Ile Ala Asp Glu Leu Phe Met Leu Gly Leu Pro Phe Leu Ala Met
        100                 105                 110

Gln Val Ala Leu Val His Trp Pro Phe Gly Lys Ala Ile Cys Arg Val
        115                 120                 125

Val Met Thr Val Asp Gly Ile Asn Gln Phe Thr Ser Ile Phe Cys Leu
130                 135                 140

Thr Val Met Ser Ile Asp Arg Tyr Leu Ala Val Val His Pro Ile Lys
145                 150                 155                 160

Ser Ala Lys Trp Arg Arg Pro Arg Thr Ala Lys Met Ile Thr Met Ala
                165                 170                 175

Val Trp Gly Val Ser Leu Leu Val Ile Leu Pro Ile Met Ile Tyr Ala
            180                 185                 190

Gly Leu Arg Ser Asn Gln Trp Gly Arg Ser Ser Cys Thr Ile Asn Trp
        195                 200                 205

Pro Gly Glu Ser Gly Ala Trp Tyr Thr Gly Phe Ile Ile Tyr Thr Phe
        210                 215                 220

Ile Leu Gly Phe Leu Val Pro Leu Thr Ile Ile Cys Leu Cys Tyr Leu
225                 230                 235                 240

Phe Ile Ile Ile Lys Val Lys Ser Ser Gly Ile Arg Val Gly Ser Ser
                245                 250                 255

Lys Arg Lys Lys Ser Glu Lys Lys Val Thr Arg Met Val Ser Ile Val
                260                 265                 270

Val Ala Val Phe Ile Phe Cys Trp Leu Pro Phe Tyr Ile Phe Asn Val
            275                 280                 285

Ser Ser Val Ser Met Ala Ile Ser Pro Thr Pro Ala Leu Lys Gly Met
        290                 295                 300

Phe Asp Phe Val Val Leu Thr Tyr Ala Asn Ser Cys Ala Asn Pro
305                 310                 315                 320

Ile Leu Tyr Ala Phe Leu Ser Asp Asn Phe Lys Ser Phe Gln Asn
                325                 330                 335

Val Leu Cys Leu Val Lys Val Ser Gly Thr Asp Asp Gly Glu Arg Ser
                340                 345                 350

Asp Ser Lys Gln Asp Lys Ser Arg Leu Asn Glu Thr Thr Glu Thr Gln
        355                 360                 365

Arg Thr Leu Leu Asn Gly Asp Leu Gln Thr Ser Ile
370                 375                 380

<210> SEQ ID NO 11
<211> LENGTH: 100
<212> TYPE: DNA
<213> ORGANISM: artificial sequence
<220> FEATURE:
<223> OTHER INFORMATION: HA tag-insert

<400> SEQUENCE: 11
atatagctag catgtaccct tacgacgtgc ccgactatgc taagctttat tatatcgatc      60
gtacatggga atgctgcacg ggctgatacg attcgaaata                          100

<210> SEQ ID NO 12
<211> LENGTH: 32
<212> TYPE: DNA
<213> ORGANISM: artificial sequence
<220> FEATURE:
<223> OTHER INFORMATION: primer

```
<400> SEQUENCE: 12
aggattaagc ttgaggggat cagtatatac ac                           32

<210> SEQ ID NO 13
<211> LENGTH: 31
<212> TYPE: DNA
<213> ORGANISM: artificial sequence
<220> FEATURE:
<223> OTHER INFORMATION: primer

<400> SEQUENCE: 13
atagcggccg cttagctgga gtgaaaactt g                            31

<210> SEQ ID NO 14
<211> LENGTH: 32
<212> TYPE: DNA
<213> ORGANISM: artificial sequence
<220> FEATURE:
<223> OTHER INFORMATION: primer

<400> SEQUENCE: 14
aggattaagc ttgattatca agtgtcaagt cc                           32

<210> SEQ ID NO 15
<211> LENGTH: 33
<212> TYPE: DNA
<213> ORGANISM: artificial sequence
<220> FEATURE:
<223> OTHER INFORMATION: primer

<400> SEQUENCE: 15
atagcggccg ctcacaagcc cacagatatt tcc                          33

<210> SEQ ID NO 16
<211> LENGTH: 28
<212> TYPE: DNA
<213> ORGANISM: artificial sequence
<220> FEATURE:
<223> OTHER INFORMATION: primer

<400> SEQUENCE: 16
tataagcttt gtcaagatga ggtcacgg                                28

<210> SEQ ID NO 17
<211> LENGTH: 27
<212> TYPE: DNA
<213> ORGANISM: artificial sequence
<220> FEATURE:
<223> OTHER INFORMATION: primer

<400> SEQUENCE: 17
atagcggccg ctatggggag aaggtgg                                 27

<210> SEQ ID NO 18
<211> LENGTH: 1092
<212> TYPE: DNA
<213> ORGANISM: artificial sequence
<220> FEATURE:
<223> OTHER INFORMATION: CXCR4 + HA Tag
<220> FEATURE:
<221> NAME/KEY: CDS
<222> LOCATION: (1)..(1092)
<223> OTHER INFORMATION: CXCR4 + HA Tag

<400> SEQUENCE: 18 atg tac cct tac gac gtg ccc gac tat gct aag ctt gag ggg atc agt      48
Met Tyr Pro Tyr Asp Val Pro Asp Tyr Ala Lys Leu Glu Gly Ile Ser
```

```
                                                        -continued
1               5                    10                   15 ata tac act tca gat aac tac acc gag gaa atg ggc tca ggg gac tat        96
Ile Tyr Thr Ser Asp Asn Tyr Thr Glu Glu Met Gly Ser Gly Asp Tyr
            20                  25                  30 gac tcc atg aag gaa ccc tgt ttc cgt gaa gaa aat gct aat ttc aat       144
Asp Ser Met Lys Glu Pro Cys Phe Arg Glu Glu Asn Ala Asn Phe Asn
        35                  40                  45 aaa atc ttc ctg ccc acc atc tac tcc atc atc ttc tta act ggc att       192
Lys Ile Phe Leu Pro Thr Ile Tyr Ser Ile Ile Phe Leu Thr Gly Ile
    50                  55                  60 gtg ggc aat gga ttg gtc atc ctg gtc atg ggt tac cag aag aaa ctg       240
Val Gly Asn Gly Leu Val Ile Leu Val Met Gly Tyr Gln Lys Lys Leu
65                  70                  75                  80 aga agc atg acg gac aag tac agg ctg cac ctg tca gtg gcc gac ctc       288
Arg Ser Met Thr Asp Lys Tyr Arg Leu His Leu Ser Val Ala Asp Leu
                85                  90                  95 ctc ttt gtc atc acg ctt ccc ttc tgg gca gtt gat gcc gtg gca aac       336
Leu Phe Val Ile Thr Leu Pro Phe Trp Ala Val Asp Ala Val Ala Asn
            100                 105                 110 tgg tac ttt ggg aac ttc cta tgc aag gca gtc cat gtc atc tac aca       384
Trp Tyr Phe Gly Asn Phe Leu Cys Lys Ala Val His Val Ile Tyr Thr
        115                 120                 125 gtc aac ctc tac agc agt gtc ctc atc ctg gcc ttc atc agt ctg gac       432
Val Asn Leu Tyr Ser Ser Val Leu Ile Leu Ala Phe Ile Ser Leu Asp
    130                 135                 140 cgc tac ctg gcc atc gtc cac gcc acc aac agt cag agg cca agg aag       480
Arg Tyr Leu Ala Ile Val His Ala Thr Asn Ser Gln Arg Pro Arg Lys
145                 150                 155                 160 ctg ttg gct gaa aag gtg gtc tat gtt ggc gtc tgg atc cct gcc ctc       528
Leu Leu Ala Glu Lys Val Val Tyr Val Gly Val Trp Ile Pro Ala Leu
                165                 170                 175 ctg ctg act att ccc gac ttc atc ttt gcc aac gtc agt gag gca gat       576
Leu Leu Thr Ile Pro Asp Phe Ile Phe Ala Asn Val Ser Glu Ala Asp
            180                 185                 190 gac aga tat atc tgt gac cgc ttc tac ccc aat gac ttg tgg gtg gtt       624
Asp Arg Tyr Ile Cys Asp Arg Phe Tyr Pro Asn Asp Leu Trp Val Val
        195                 200                 205 gtg ttc cag ttt cag cac atc atg gtt ggc ctt atc ctg cct ggt att       672
Val Phe Gln Phe Gln His Ile Met Val Gly Leu Ile Leu Pro Gly Ile
    210                 215                 220 gtc atc ctg tcc tgc tat tgc att atc atc tcc aag ctg tca cac tcc       720
Val Ile Leu Ser Cys Tyr Cys Ile Ile Ile Ser Lys Leu Ser His Ser
225                 230                 235                 240 aag ggc cac cag aag cgc aag gcc ctc aag acc aca gtc atc ctc atc       768
Lys Gly His Gln Lys Arg Lys Ala Leu Lys Thr Thr Val Ile Leu Ile
                245                 250                 255 ctg gct ttc ttc gcc tgt tgg ctg cct tac tac att ggg atc agc atc       816
Leu Ala Phe Phe Ala Cys Trp Leu Pro Tyr Tyr Ile Gly Ile Ser Ile
            260                 265                 270 gac tcc ttc atc ctc ctg gaa atc atc aag caa ggg tgt gag ttt gag       864
Asp Ser Phe Ile Leu Leu Glu Ile Ile Lys Gln Gly Cys Glu Phe Glu
        275                 280                 285 aac act gtg cac aag tgg att tcc atc acc gag gcc cta gct ttc ttc       912
Asn Thr Val His Lys Trp Ile Ser Ile Thr Glu Ala Leu Ala Phe Phe
    290                 295                 300 cac tgt tgt ctg aac ccc atc ctc tat gct ttc ctt gga gcc aaa ttt       960
His Cys Cys Leu Asn Pro Ile Leu Tyr Ala Phe Leu Gly Ala Lys Phe
305                 310                 315                 320 aaa acc tct gcc cag cac gca ctc acc tct gtg agc aga ggg tcc agc      1008
Lys Thr Ser Ala Gln His Ala Leu Thr Ser Val Ser Arg Gly Ser Ser
```

```
                    325                 330                 335
ctc aag atc ctc tcc aaa gga aag cga ggt gga cat tca tct gtt tcc    1056
Leu Lys Ile Leu Ser Lys Gly Lys Arg Gly Gly His Ser Ser Val Ser
            340                 345                 350 act gag tct gag tct tca agt ttt cac tcc agc taa                    1092
Thr Glu Ser Glu Ser Ser Ser Phe His Ser Ser
        355                 360
```

<210> SEQ ID NO 19
<211> LENGTH: 363
<212> TYPE: PRT
<213> ORGANISM: artificial sequence
<220> FEATURE:
<223> OTHER INFORMATION: CXCR4 + HA Tag

<400> SEQUENCE: 19

```
Met Tyr Pro Tyr Asp Val Pro Asp Tyr Ala Lys Leu Glu Gly Ile Ser
1               5                   10                  15

Ile Tyr Thr Ser Asp Asn Tyr Thr Glu Glu Met Gly Ser Gly Asp Tyr
            20                  25                  30

Asp Ser Met Lys Glu Pro Cys Phe Arg Glu Glu Asn Ala Asn Phe Asn
        35                  40                  45

Lys Ile Phe Leu Pro Thr Ile Tyr Ser Ile Ile Phe Leu Thr Gly Ile
    50                  55                  60

Val Gly Asn Gly Leu Val Ile Leu Val Met Gly Tyr Gln Lys Lys Leu
65                  70                  75                  80

Arg Ser Met Thr Asp Lys Tyr Arg Leu His Leu Ser Val Ala Asp Leu
                85                  90                  95

Leu Phe Val Ile Thr Leu Pro Phe Trp Ala Val Asp Ala Val Ala Asn
            100                 105                 110

Trp Tyr Phe Gly Asn Phe Leu Cys Lys Ala Val His Val Ile Tyr Thr
        115                 120                 125

Val Asn Leu Tyr Ser Ser Val Leu Ile Leu Ala Phe Ile Ser Leu Asp
    130                 135                 140

Arg Tyr Leu Ala Ile Val His Ala Thr Asn Ser Gln Arg Pro Arg Lys
145                 150                 155                 160

Leu Leu Ala Glu Lys Val Val Tyr Val Gly Val Trp Ile Pro Ala Leu
                165                 170                 175

Leu Leu Thr Ile Pro Asp Phe Ile Phe Ala Asn Val Ser Glu Ala Asp
            180                 185                 190

Asp Arg Tyr Ile Cys Asp Arg Phe Tyr Pro Asn Asp Leu Trp Val Val
        195                 200                 205

Val Phe Gln Phe Gln His Ile Met Val Gly Leu Ile Leu Pro Gly Ile
    210                 215                 220

Val Ile Leu Ser Cys Tyr Cys Ile Ile Ile Ser Lys Leu Ser His Ser
225                 230                 235                 240

Lys Gly His Gln Lys Arg Lys Ala Leu Lys Thr Thr Val Ile Leu Ile
                245                 250                 255

Leu Ala Phe Phe Ala Cys Trp Leu Pro Tyr Tyr Ile Gly Ile Ser Ile
            260                 265                 270

Asp Ser Phe Ile Leu Leu Glu Ile Ile Lys Gln Gly Cys Glu Phe Glu
        275                 280                 285

Asn Thr Val His Lys Trp Ile Ser Ile Thr Glu Ala Leu Ala Phe Phe
    290                 295                 300

His Cys Cys Leu Asn Pro Ile Leu Tyr Ala Phe Leu Gly Ala Lys Phe
305                 310                 315                 320
```

```
Lys Thr Ser Ala Gln His Ala Leu Thr Ser Val Ser Arg Gly Ser Ser
                325                 330                 335

Leu Lys Ile Leu Ser Lys Gly Lys Arg Gly Gly His Ser Ser Val Ser
                340                 345                 350

Thr Glu Ser Glu Ser Ser Ser Phe His Ser Ser
                355                 360

<210> SEQ ID NO 20
<211> LENGTH: 1092
<212> TYPE: DNA
<213> ORGANISM: artificial sequence
<220> FEATURE:
<223> OTHER INFORMATION: HA-CCR5
<220> FEATURE:
<221> NAME/KEY: CDS
<222> LOCATION: (1)..(1092)
<223> OTHER INFORMATION: HA-CCR5

<400> SEQUENCE: 20
```

| | | | | | | | | | | | | | | | | |
|---|---|---|---|---|---|---|---|---|---|---|---|---|---|---|---|---|
| atg | tac | cct | tac | gac | gtg | ccc | gac | tat | gct | aag | ctt | gat | tat | caa | gtg | 48 |
| Met | Tyr | Pro | Tyr | Asp | Val | Pro | Asp | Tyr | Ala | Lys | Leu | Asp | Tyr | Gln | Val | |
| 1 | | | | 5 | | | | | 10 | | | | | 15 | | |
| tca | agt | cca | atc | tat | gac | atc | aat | tat | tat | aca | tcg | gag | ccc | tgc | caa | 96 |
| Ser | Ser | Pro | Ile | Tyr | Asp | Ile | Asn | Tyr | Tyr | Thr | Ser | Glu | Pro | Cys | Gln | |
| | | | 20 | | | | | 25 | | | | | 30 | | | |
| aaa | atc | aat | gtg | aag | caa | atc | gca | gcc | cgc | ctc | ctg | cct | ccg | ctc | tac | 144 |
| Lys | Ile | Asn | Val | Lys | Gln | Ile | Ala | Ala | Arg | Leu | Leu | Pro | Pro | Leu | Tyr | |
| | | 35 | | | | | 40 | | | | | 45 | | | | |
| tca | ctg | gtg | ttc | atc | ttt | ggt | ttt | gtg | ggc | aac | atg | ctg | gtc | atc | ctc | 192 |
| Ser | Leu | Val | Phe | Ile | Phe | Gly | Phe | Val | Gly | Asn | Met | Leu | Val | Ile | Leu | |
| | 50 | | | | | 55 | | | | | 60 | | | | | |
| atc | ctg | ata | aac | tgc | aaa | agg | ctg | aag | agc | atg | act | gac | atc | tac | ctg | 240 |
| Ile | Leu | Ile | Asn | Cys | Lys | Arg | Leu | Lys | Ser | Met | Thr | Asp | Ile | Tyr | Leu | |
| 65 | | | | | 70 | | | | | 75 | | | | | 80 | |
| ctc | aac | ctg | gcc | atc | tct | gac | ctg | ttt | ttc | ctt | ctt | act | gtc | ccc | ttc | 288 |
| Leu | Asn | Leu | Ala | Ile | Ser | Asp | Leu | Phe | Phe | Leu | Leu | Thr | Val | Pro | Phe | |
| | | | | 85 | | | | | 90 | | | | | 95 | | |
| tgg | gct | cac | tat | gct | gcc | gcc | cag | tgg | gac | ttt | gga | aat | aca | atg | tgt | 336 |
| Trp | Ala | His | Tyr | Ala | Ala | Ala | Gln | Trp | Asp | Phe | Gly | Asn | Thr | Met | Cys | |
| | | | 100 | | | | | 105 | | | | | 110 | | | |
| caa | ctc | ttg | aca | ggg | ctc | tat | ttt | ata | ggc | ttc | ttc | tct | gga | atc | ttc | 384 |
| Gln | Leu | Leu | Thr | Gly | Leu | Tyr | Phe | Ile | Gly | Phe | Phe | Ser | Gly | Ile | Phe | |
| | | 115 | | | | | 120 | | | | | 125 | | | | |
| ttc | atc | atc | ctc | ctg | aca | atc | gat | agg | tac | ctg | gct | gtc | gtc | cat | gct | 432 |
| Phe | Ile | Ile | Leu | Leu | Thr | Ile | Asp | Arg | Tyr | Leu | Ala | Val | Val | His | Ala | |
| | 130 | | | | | 135 | | | | | 140 | | | | | |
| gtg | ttt | gct | tta | aaa | gcc | agg | acg | gtc | acc | ttt | ggg | gtg | gtg | aca | agt | 480 |
| Val | Phe | Ala | Leu | Lys | Ala | Arg | Thr | Val | Thr | Phe | Gly | Val | Val | Thr | Ser | |
| 145 | | | | | 150 | | | | | 155 | | | | | 160 | |
| gtg | atc | act | tgg | gtg | gtg | gct | gtg | ttt | gcg | tct | ctc | cca | gga | atc | atc | 528 |
| Val | Ile | Thr | Trp | Val | Val | Ala | Val | Phe | Ala | Ser | Leu | Pro | Gly | Ile | Ile | |
| | | | | 165 | | | | | 170 | | | | | 175 | | |
| ttt | acc | aga | tct | caa | aaa | gaa | ggt | ctt | cat | tac | acc | tgc | agc | tct | cat | 576 |
| Phe | Thr | Arg | Ser | Gln | Lys | Glu | Gly | Leu | His | Tyr | Thr | Cys | Ser | Ser | His | |
| | | | 180 | | | | | 185 | | | | | 190 | | | |
| ttt | cca | tac | agt | cag | tat | caa | ttc | tgg | aag | aat | ttc | cag | aca | tta | aag | 624 |
| Phe | Pro | Tyr | Ser | Gln | Tyr | Gln | Phe | Trp | Lys | Asn | Phe | Gln | Thr | Leu | Lys | |
| | | 195 | | | | | 200 | | | | | 205 | | | | |
| ata | gtc | atc | ttg | ggg | ctg | gtc | ctg | ccg | ctg | ctt | gtc | atg | gtc | atc | tgc | 672 |
| Ile | Val | Ile | Leu | Gly | Leu | Val | Leu | Pro | Leu | Leu | Val | Met | Val | Ile | Cys | |
| | 210 | | | | | 215 | | | | | 220 | | | | | |
| tac | tcg | gga | atc | cta | aaa | act | ctg | ctt | cgg | tgt | cga | aat | gag | aag | aag | 720 |

```
Tyr Ser Gly Ile Leu Lys Thr Leu Leu Arg Cys Arg Asn Glu Lys Lys
225                 230                 235                 240 agg cac agg gct gtg agg ctt atc ttc acc atc atg att gtt tat ttt    768
Arg His Arg Ala Val Arg Leu Ile Phe Thr Ile Met Ile Val Tyr Phe
                245                 250                 255 ctc ttc tgg gct ccc tac aac att gtc ctt ctc ctg aac acc ttc cag    816
Leu Phe Trp Ala Pro Tyr Asn Ile Val Leu Leu Leu Asn Thr Phe Gln
            260                 265                 270 gaa ttc ttt ggc ctg aat aat tgc agt agc tct aac agg ttg gac caa    864
Glu Phe Phe Gly Leu Asn Asn Cys Ser Ser Ser Asn Arg Leu Asp Gln
        275                 280                 285 gct atg cag gtg aca gag act ctt ggg atg acg cac tgc tgc atc aac    912
Ala Met Gln Val Thr Glu Thr Leu Gly Met Thr His Cys Cys Ile Asn
    290                 295                 300 ccc atc atc tat gcc ttt gtc ggg gag aag ttc aga aac tac ctc tta    960
Pro Ile Ile Tyr Ala Phe Val Gly Glu Lys Phe Arg Asn Tyr Leu Leu
305                 310                 315                 320 gtc ttc ttc caa aag cac att gcc aaa cgc ttc tgc aaa tgc tgt tct   1008
Val Phe Phe Gln Lys His Ile Ala Lys Arg Phe Cys Lys Cys Cys Ser
                325                 330                 335 att ttc cag caa gag gct ccc gag cga gca agc tca gtt tac acc cga   1056
Ile Phe Gln Gln Glu Ala Pro Glu Arg Ala Ser Ser Val Tyr Thr Arg
            340                 345                 350 tcc act ggg gag cag gaa ata tct gtg ggc ttg tga                    1092
Ser Thr Gly Glu Gln Glu Ile Ser Val Gly Leu
        355                 360

<210> SEQ ID NO 21
<211> LENGTH: 363
<212> TYPE: PRT
<213> ORGANISM: artificial sequence
<220> FEATURE:
<223> OTHER INFORMATION: HA-CCR5

<400> SEQUENCE: 21

Met Tyr Pro Tyr Asp Val Pro Asp Tyr Ala Lys Leu Asp Tyr Gln Val
1               5                   10                  15

Ser Ser Pro Ile Tyr Asp Ile Asn Tyr Tyr Thr Ser Glu Pro Cys Gln
                20                  25                  30

Lys Ile Asn Val Lys Gln Ile Ala Ala Arg Leu Leu Pro Pro Leu Tyr
            35                  40                  45

Ser Leu Val Phe Ile Phe Gly Phe Val Gly Asn Met Leu Val Ile Leu
        50                  55                  60

Ile Leu Ile Asn Cys Lys Arg Leu Lys Ser Met Thr Asp Ile Tyr Leu
65                  70                  75                  80

Leu Asn Leu Ala Ile Ser Asp Leu Phe Phe Leu Thr Val Pro Phe
                85                  90                  95

Trp Ala His Tyr Ala Ala Ala Gln Trp Asp Phe Gly Asn Thr Met Cys
            100                 105                 110

Gln Leu Leu Thr Gly Leu Tyr Phe Ile Gly Phe Phe Ser Gly Ile Phe
        115                 120                 125

Phe Ile Ile Leu Leu Thr Ile Asp Arg Tyr Leu Ala Val Val His Ala
    130                 135                 140

Val Phe Ala Leu Lys Ala Arg Thr Val Thr Phe Gly Val Val Thr Ser
145                 150                 155                 160

Val Ile Thr Trp Val Val Ala Val Phe Ala Ser Leu Pro Gly Ile Ile
                165                 170                 175

Phe Thr Arg Ser Gln Lys Glu Gly Leu His Tyr Thr Cys Ser Ser His
            180                 185                 190
```

```
Phe Pro Tyr Ser Gln Tyr Gln Phe Trp Lys Asn Phe Gln Thr Leu Lys
        195                 200                 205

Ile Val Ile Leu Gly Leu Val Leu Pro Leu Leu Val Met Val Ile Cys
        210                 215                 220

Tyr Ser Gly Ile Leu Lys Thr Leu Leu Arg Cys Arg Asn Glu Lys Lys
225                 230                 235                 240

Arg His Arg Ala Val Arg Leu Ile Phe Thr Ile Met Ile Val Tyr Phe
                245                 250                 255

Leu Phe Trp Ala Pro Tyr Asn Ile Val Leu Leu Leu Asn Thr Phe Gln
                260                 265                 270

Glu Phe Phe Gly Leu Asn Asn Cys Ser Ser Ser Asn Arg Leu Asp Gln
                275                 280                 285

Ala Met Gln Val Thr Glu Thr Leu Gly Met Thr His Cys Cys Ile Asn
        290                 295                 300

Pro Ile Ile Tyr Ala Phe Val Gly Glu Lys Phe Arg Asn Tyr Leu Leu
305                 310                 315                 320

Val Phe Phe Gln Lys His Ile Ala Lys Arg Phe Cys Lys Cys Cys Ser
                325                 330                 335

Ile Phe Gln Gln Glu Ala Pro Glu Arg Ala Ser Ser Val Tyr Thr Arg
                340                 345                 350

Ser Thr Gly Glu Gln Glu Ile Ser Val Gly Leu
        355                 360

<210> SEQ ID NO 22
<211> LENGTH: 1170
<212> TYPE: DNA
<213> ORGANISM: artificial sequence
<220> FEATURE:
<223> OTHER INFORMATION: HA-CCR7
<220> FEATURE:
<221> NAME/KEY: CDS
<222> LOCATION: (1)..(1170)
<223> OTHER INFORMATION: HA-CCR7

<400> SEQUENCE: 22 atg tac cct tac gac gtg ccc gac tat gct aag ctt gac ctg ggg aaa    48
Met Tyr Pro Tyr Asp Val Pro Asp Tyr Ala Lys Leu Asp Leu Gly Lys
1               5                   10                  15 cca atg aaa agc gtg ctg gtg gtg gct ctc ctt gtc att ttc cag gta    96
Pro Met Lys Ser Val Leu Val Val Ala Leu Leu Val Ile Phe Gln Val
            20                  25                  30 tgc ctg tgt caa gat gag gtc acg gac gat tac atc gga gac aac acc   144
Cys Leu Cys Gln Asp Glu Val Thr Asp Asp Tyr Ile Gly Asp Asn Thr
        35                  40                  45 aca gtg gac tac act ttg ttc gag tct ttg tgc tcc aag aag gac gtg   192
Thr Val Asp Tyr Thr Leu Phe Glu Ser Leu Cys Ser Lys Lys Asp Val
    50                  55                  60 cgg aac ttt aaa gcc tgg ttc ctc cct atc atg tac tcc atc att tgt   240
Arg Asn Phe Lys Ala Trp Phe Leu Pro Ile Met Tyr Ser Ile Ile Cys
65                  70                  75                  80 ttc gtg ggc cta ctg ggc aat ggg ctg gtc gtg ttg acc tat atc tat   288
Phe Val Gly Leu Leu Gly Asn Gly Leu Val Val Leu Thr Tyr Ile Tyr
                85                  90                  95 ttc aag agg ctc aag acc atg acc gat acc tac ctg ctc aac ctg gcg   336
Phe Lys Arg Leu Lys Thr Met Thr Asp Thr Tyr Leu Leu Asn Leu Ala
            100                 105                 110 gtg gca gac atc ctc ttc ctc ctg acc ctt ccc ttc tgg gcc tac agc   384
Val Ala Asp Ile Leu Phe Leu Leu Thr Leu Pro Phe Trp Ala Tyr Ser
        115                 120                 125
```

```
gcg gcc aag tcc tgg gtc ttc ggt gtc cac ttt tgc aag ctc atc ttt      432
Ala Ala Lys Ser Trp Val Phe Gly Val His Phe Cys Lys Leu Ile Phe
    130             135                 140 gcc atc tac aag atg agc ttc ttc agt ggc atg ctc cta ctt ctt tgc      480
Ala Ile Tyr Lys Met Ser Phe Phe Ser Gly Met Leu Leu Leu Leu Cys
145                 150                 155                 160 atc agc att gac cgc tac gtg gcc atc gtc cag gct gtc tca gct cac      528
Ile Ser Ile Asp Arg Tyr Val Ala Ile Val Gln Ala Val Ser Ala His
                165                 170                 175 cgc cac cgt gcc cgc gtc ctt ctc atc agc aag ctg tcc tgt gtg ggc      576
Arg His Arg Ala Arg Val Leu Leu Ile Ser Lys Leu Ser Cys Val Gly
            180                 185                 190 atc tgg ata cta gcc aca gtg ctc tcc atc cca gag ctc ctg tac agt      624
Ile Trp Ile Leu Ala Thr Val Leu Ser Ile Pro Glu Leu Leu Tyr Ser
        195                 200                 205 gac ctc cag agg agc agc agt gag caa gcg atg cga tgc tct ctc atc      672
Asp Leu Gln Arg Ser Ser Ser Glu Gln Ala Met Arg Cys Ser Leu Ile
    210                 215                 220 aca gag cat gtg gag gcc ttt atc acc atc cag gtg gcc cag atg gtg      720
Thr Glu His Val Glu Ala Phe Ile Thr Ile Gln Val Ala Gln Met Val
225                 230                 235                 240 atc ggc ttt ctg gtc ccc ctg ctg gcc atg agc ttc tgt tac ctt gtc      768
Ile Gly Phe Leu Val Pro Leu Leu Ala Met Ser Phe Cys Tyr Leu Val
                245                 250                 255 atc atc cgc acc ctg ctc cag gca cgc aac ttt gag cgc aac aag gcc      816
Ile Ile Arg Thr Leu Leu Gln Ala Arg Asn Phe Glu Arg Asn Lys Ala
            260                 265                 270 atc aag gtg atc atc gct gtg gtc gtg gtc ttc ata gtc ttc cag ctg      864
Ile Lys Val Ile Ile Ala Val Val Val Phe Ile Val Phe Gln Leu
        275                 280                 285 ccc tac aat ggg gtg gtc ctg gcc cag acg gtg gcc aac ttc aac atc      912
Pro Tyr Asn Gly Val Val Leu Ala Gln Thr Val Ala Asn Phe Asn Ile
    290                 295                 300 acc agt agc acc tgt gag ctc agt aag caa ctc aac atc gcc tac gac      960
Thr Ser Ser Thr Cys Glu Leu Ser Lys Gln Leu Asn Ile Ala Tyr Asp
305                 310                 315                 320 gtc acc tac agc ctg gcc tgt gtc cgc tgc tgc gtc aac cct ttc ttg     1008
Val Thr Tyr Ser Leu Ala Cys Val Arg Cys Cys Val Asn Pro Phe Leu
                325                 330                 335 tac gcc ttc atc ggc gtc aag ttc cgc aac gat ctc ttc aag ctc ttc     1056
Tyr Ala Phe Ile Gly Val Lys Phe Arg Asn Asp Leu Phe Lys Leu Phe
            340                 345                 350 aag gac ctg ggc tgc ctc agc cag gag cag ctc cgg cag tgg tct tcc     1104
Lys Asp Leu Gly Cys Leu Ser Gln Glu Gln Leu Arg Gln Trp Ser Ser
        355                 360                 365 tgt cgg cac atc cgg cgc tcc tcc atg agt gtg gag gcc gag acc acc     1152
Cys Arg His Ile Arg Arg Ser Ser Met Ser Val Glu Ala Glu Thr Thr
    370                 375                 380 acc acc ttc tcc cca tag                                              1170
Thr Thr Phe Ser Pro
385

<210> SEQ ID NO 23
<211> LENGTH: 389
<212> TYPE: PRT
<213> ORGANISM: artificial sequence
<220> FEATURE:
<223> OTHER INFORMATION: HA-CCR7

<400> SEQUENCE: 23

Met Tyr Pro Tyr Asp Val Pro Asp Tyr Ala Lys Leu Asp Leu Gly Lys
1               5                   10                  15
```

Pro Met Lys Ser Val Leu Val Ala Leu Leu Val Ile Phe Gln Val
         20                  25                  30

Cys Leu Cys Gln Asp Glu Val Thr Asp Asp Tyr Ile Gly Asp Asn Thr
             35                  40                  45

Thr Val Asp Tyr Thr Leu Phe Glu Ser Leu Cys Ser Lys Lys Asp Val
 50                  55                  60

Arg Asn Phe Lys Ala Trp Phe Leu Pro Ile Met Tyr Ser Ile Ile Cys
 65                  70                  75                  80

Phe Val Gly Leu Leu Gly Asn Gly Leu Val Val Leu Thr Tyr Ile Tyr
                 85                  90                  95

Phe Lys Arg Leu Lys Thr Met Thr Asp Thr Tyr Leu Leu Asn Leu Ala
                100                 105                 110

Val Ala Asp Ile Leu Phe Leu Leu Thr Leu Pro Phe Trp Ala Tyr Ser
            115                 120                 125

Ala Ala Lys Ser Trp Val Phe Gly Val His Phe Cys Lys Leu Ile Phe
        130                 135                 140

Ala Ile Tyr Lys Met Ser Phe Phe Ser Gly Met Leu Leu Leu Leu Cys
145                 150                 155                 160

Ile Ser Ile Asp Arg Tyr Val Ala Ile Val Gln Ala Val Ser Ala His
                165                 170                 175

Arg His Arg Ala Arg Val Leu Leu Ile Ser Lys Leu Ser Cys Val Gly
            180                 185                 190

Ile Trp Ile Leu Ala Thr Val Leu Ser Ile Pro Glu Leu Leu Tyr Ser
        195                 200                 205

Asp Leu Gln Arg Ser Ser Ser Glu Gln Ala Met Arg Cys Ser Leu Ile
210                 215                 220

Thr Glu His Val Glu Ala Phe Ile Thr Ile Gln Val Ala Gln Met Val
225                 230                 235                 240

Ile Gly Phe Leu Val Pro Leu Leu Ala Met Ser Phe Cys Tyr Leu Val
                245                 250                 255

Ile Ile Arg Thr Leu Leu Gln Ala Arg Asn Phe Glu Arg Asn Lys Ala
            260                 265                 270

Ile Lys Val Ile Ile Ala Val Val Val Phe Ile Val Phe Gln Leu
        275                 280                 285

Pro Tyr Asn Gly Val Val Leu Ala Gln Thr Val Ala Asn Phe Asn Ile
290                 295                 300

Thr Ser Ser Thr Cys Glu Leu Ser Lys Gln Leu Asn Ile Ala Tyr Asp
305                 310                 315                 320

Val Thr Tyr Ser Leu Ala Cys Val Arg Cys Cys Val Asn Pro Phe Leu
                325                 330                 335

Tyr Ala Phe Ile Gly Val Lys Phe Arg Asn Asp Leu Phe Lys Leu Phe
            340                 345                 350

Lys Asp Leu Gly Cys Leu Ser Gln Glu Gln Leu Arg Gln Trp Ser Ser
        355                 360                 365

Cys Arg His Ile Arg Arg Ser Ser Met Ser Val Glu Ala Glu Thr Thr
370                 375                 380

Thr Thr Phe Ser Pro
385

<210> SEQ ID NO 24
<211> LENGTH: 30
<212> TYPE: DNA
<213> ORGANISM: artificial sequence
<220> FEATURE:
<223> OTHER INFORMATION: primer

```
<400> SEQUENCE: 24
aggaggaagc ttatggccgt catggctccc                                            30

<210> SEQ ID NO 25
<211> LENGTH: 30
<212> TYPE: DNA
<213> ORGANISM: artificial sequence
<220> FEATURE:
<223> OTHER INFORMATION: primer

<400> SEQUENCE: 25
ggaaggttcg aacactttac aagctgtgag                                            30

<210> SEQ ID NO 26
<211> LENGTH: 1164
<212> TYPE: DNA
<213> ORGANISM: artificial sequence
<220> FEATURE:
<223> OTHER INFORMATION: HLA A201 + Myc His

<400> SEQUENCE: 26
atggccgtca tggcgccccg aaccctcgtc ctgctactct cgggggctct ggccctgacc           60
cagacctggg cgggctctca ctccatgagg tatttcttca catccgtgtc ccggcccggc          120
cgcggggagc cccgcttcat cgcagtgggc tacgtggacg acacgcagtt cgtgcggttc          180
gacagcgacg ccgcgagcca gaggatggag ccgcgggcgc cgtggataga gcaggagggt          240
ccggagtatt gggacgggga gacacggaaa gtgaaggccc actcacagac tcaccgagtg          300
gacctgggga ccctgcgcgg ctactacaac agagcgaggg ccggttctca caccgtccag          360
aggatgtatg gctgcgacgt ggggtcggac tggcgcttcc tccgcgggta ccaccagtac          420
gcctacgacg gcaaggatta catcgccctg aaagaggacc tgcgctcttg gaccgcggcg          480
gacatggcag ctcagaccac caagcacaag tgggaggcgg cccatgtggc ggagcagttg          540
agagcctacc tggagggcac gtgcgtggag tggctccgca gatacctgga aacgggaag           600 gagacgctgc agcgcacgga cgcccccaaa acgcatatga ctcaccacgc tgtctctgac          660
catgaagcca ccctgaggtg ctgggccctg agcttctacc ctgcggagat cacactgacc          720
tggcagcggg atggggagga ccagacccag gacacggagc tcgtggagac caggcctgca          780
ggggatggaa ccttccagaa gtgggcggct gtggtggtgc cttctggaca ggagcagaga          840
tacacctgcc atgtgcagca tgagggtttg cccaagcccc tcaccctgag atgggagccg          900
tcttcccagc ccaccatccc catcgtgggc atcattgctg gcctggttct ctttggagct          960
gtgatcactg gagctgtggt cgctgctgtg atgtggagga ggaagagctc agatagaaaa         1020
ggagggagct actctcaggc tgcaagcagt gacagtgccc agggctctga tgtgtctctc         1080
acagcttgta aagtgttcga acaaaaactc atctcagaag aggatctgaa tatgcatacc         1140
ggtcatcatc accatcacca ttga                                               1164

<210> SEQ ID NO 27
<211> LENGTH: 30
<212> TYPE: DNA
<213> ORGANISM: artificial sequence
<220> FEATURE:
<223> OTHER INFORMATION: primer

<400> SEQUENCE: 27
aggaggaagc ttatgtctcg ctccgtggcc                                            30
```

```
<210> SEQ ID NO 28
<211> LENGTH: 33
<212> TYPE: DNA
<213> ORGANISM: artificial sequence
<220> FEATURE:
<223> OTHER INFORMATION: primer

<400> SEQUENCE: 28
ggaaggttcg aattacatgt ctcgatccca ctt                          33

<210> SEQ ID NO 29
<211> LENGTH: 359
<212> TYPE: DNA
<213> ORGANISM: homo sapiens

<400> SEQUENCE: 29
atgtctcgct ccgtggcctt agctgtgctc gcgctactct ctctttctgg cctggaggct    60
atccagcgta ctccaaagat tcaggtttac tcacgtcatc cagcagagaa tggaaagtca   120
aatttcctga attgctatgt gtctgggttt catccatccg acattgaagt tgacttactg   180
aagaatggag agagaattga aaaagtggag cattcagact tgtctttcag caaggactgg   240
tctttctatc tcttgtacta cactgaattc acccccactg aaaaagatga gtatgcctgc   300
cgtgtgaacc atgtgacttt gtcacagccc aagatagtta gtgggatcg gacatgtaa    359

<210> SEQ ID NO 30
<211> LENGTH: 31
<212> TYPE: DNA
<213> ORGANISM: artificial sequence
<220> FEATURE:
<223> OTHER INFORMATION: primer

<400> SEQUENCE: 30
ggaagggcgg ccgcgtttaa actcaatggt g                            31

<210> SEQ ID NO 31
<211> LENGTH: 31
<212> TYPE: DNA
<213> ORGANISM: artificial sequence
<220> FEATURE:
<223> OTHER INFORMATION: primer

<400> SEQUENCE: 31
ggaattggat ccatgatcga acatacaac c                             31

<210> SEQ ID NO 32
<211> LENGTH: 35
<212> TYPE: DNA
<213> ORGANISM: artificial sequence
<220> FEATURE:
<223> OTHER INFORMATION: primer

<400> SEQUENCE: 32
ggaaggttcg aatcagagtt tgagtaagcc aaagg                        35

<210> SEQ ID NO 33
<211> LENGTH: 786
<212> TYPE: DNA
<213> ORGANISM: homo sapiens
<220> FEATURE:
<221> NAME/KEY: CDS
<222> LOCATION: (1)..(786)

<400> SEQUENCE: 33 atg atc gaa aca tac aac caa act tct ccc cga tct gcg gcc act gga    48
Met Ile Glu Thr Tyr Asn Gln Thr Ser Pro Arg Ser Ala Ala Thr Gly
```

```
1               5                   10                  15
ctg ccc atc agc atg aaa att ttt atg tat tta ctt act gtt ttt ctt       96
Leu Pro Ile Ser Met Lys Ile Phe Met Tyr Leu Leu Thr Val Phe Leu
         20                  25                  30 atc acc cag atg att ggg tca gca ctt ttt gct gtg tat ctt cat aga      144
Ile Thr Gln Met Ile Gly Ser Ala Leu Phe Ala Val Tyr Leu His Arg
         35                  40                  45 agg ttg gac aag ata gaa gat gaa agg aat ctt cat gaa gat ttt gta      192
Arg Leu Asp Lys Ile Glu Asp Glu Arg Asn Leu His Glu Asp Phe Val
50                  55                  60 ttc atg aaa acg ata cag aga tgc aac aca gga gaa aga tcc tta tcc      240
Phe Met Lys Thr Ile Gln Arg Cys Asn Thr Gly Glu Arg Ser Leu Ser
65                  70                  75                  80 tta ctg aac tgt gag gag att aaa agc cag ttt gaa ggc ttt gtg aag      288
Leu Leu Asn Cys Glu Glu Ile Lys Ser Gln Phe Glu Gly Phe Val Lys
             85                  90                  95 gat ata atg tta aac aaa gag gag acg aag aaa gaa aac agc ttt gaa      336
Asp Ile Met Leu Asn Lys Glu Glu Thr Lys Lys Glu Asn Ser Phe Glu
        100                 105                 110 atg caa aaa ggt gat cag aat cct caa att gcg gca cat gtc ata agt      384
Met Gln Lys Gly Asp Gln Asn Pro Gln Ile Ala Ala His Val Ile Ser
        115                 120                 125 gag gcc agc agt aaa aca aca tct gtg tta cag tgg gct gaa aaa gga      432
Glu Ala Ser Ser Lys Thr Thr Ser Val Leu Gln Trp Ala Glu Lys Gly
130                 135                 140 tac tac acc atg agc aac aac ttg gta acc ctg gaa aat ggg aaa cag      480
Tyr Tyr Thr Met Ser Asn Asn Leu Val Thr Leu Glu Asn Gly Lys Gln
145                 150                 155                 160 ctg acc gtt aaa aga caa gga ctc tat tat atc tat gcc caa gtc acc      528
Leu Thr Val Lys Arg Gln Gly Leu Tyr Tyr Ile Tyr Ala Gln Val Thr
                165                 170                 175 ttc tgt tcc aat cgg gaa gct tcg agt caa gct cca ttt ata gcc agc      576
Phe Cys Ser Asn Arg Glu Ala Ser Ser Gln Ala Pro Phe Ile Ala Ser
            180                 185                 190 ctc tgc cta aag tcc ccc ggt aga ttc gag aga atc tta ctc aga gct      624
Leu Cys Leu Lys Ser Pro Gly Arg Phe Glu Arg Ile Leu Leu Arg Ala
        195                 200                 205 gca aat acc cac agt tcc gcc aaa cct tgc ggg caa caa tcc att cac      672
Ala Asn Thr His Ser Ser Ala Lys Pro Cys Gly Gln Gln Ser Ile His
210                 215                 220 ttg gga gga gta ttt gaa ttg caa cca ggt gct tcg gtg ttt gtc aat      720
Leu Gly Gly Val Phe Glu Leu Gln Pro Gly Ala Ser Val Phe Val Asn
225                 230                 235                 240 gtg act gat cca agc caa gtg agc cat ggc act ggc ttc acg tcc ttt      768
Val Thr Asp Pro Ser Gln Val Ser His Gly Thr Gly Phe Thr Ser Phe
                245                 250                 255 ggc tta ctc aaa ctc tga                                              786
Gly Leu Leu Lys Leu
        260

<210> SEQ ID NO 34
<211> LENGTH: 261
<212> TYPE: PRT
<213> ORGANISM: homo sapiens

<400> SEQUENCE: 34

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30
```

```
Ile Thr Gln Met Ile Gly Ser Ala Leu Phe Ala Val Tyr Leu His Arg
         35                  40                  45

Arg Leu Asp Lys Ile Glu Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
        130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 35
<211> LENGTH: 33
<212> TYPE: DNA
<213> ORGANISM: artificial sequence
<220> FEATURE:
<223> OTHER INFORMATION: primer

<400> SEQUENCE: 35
cctttttgcc ctccaaagct gttttctttc ttc                            33

<210> SEQ ID NO 36
<211> LENGTH: 32
<212> TYPE: DNA
<213> ORGANISM: artificial sequence
<220> FEATURE:
<223> OTHER INFORMATION: primer

<400> SEQUENCE: 36
acagctttgg agggcaaaaa ggtgatcaga at                             32

<210> SEQ ID NO 37
<211> LENGTH: 786
<212> TYPE: DNA
<213> ORGANISM: artificial sequence
<220> FEATURE:
<223> OTHER INFORMATION: mutCD40L
<220> FEATURE:
<221> NAME/KEY: CDS
<222> LOCATION: (1)..(786)
<223> OTHER INFORMATION: mutCD40L
```

<400> SEQUENCE: 37

```
atg atc gaa aca tac aac caa act tct ccc cga tct gcg gcc act gga      48
Met Ile Glu Thr Tyr Asn Gln Thr Ser Pro Arg Ser Ala Ala Thr Gly
1               5                   10                  15 ctg ccc atc agc atg aaa att ttt atg tat tta ctt act gtt ttt ctt      96
Leu Pro Ile Ser Met Lys Ile Phe Met Tyr Leu Leu Thr Val Phe Leu
                20                  25                  30 atc acc cag atg att ggg tca gca ctt ttt gct gtg tat ctt cat aga     144
Ile Thr Gln Met Ile Gly Ser Ala Leu Phe Ala Val Tyr Leu His Arg
            35                  40                  45 agg ttg gac aag ata gaa gat gaa agg aat ctt cat gaa gat ttt gta     192
Arg Leu Asp Lys Ile Glu Asp Glu Arg Asn Leu His Glu Asp Phe Val
    50                  55                  60 ttc atg aaa acg ata cag aga tgc aac aca gga gaa aga tcc tta tcc     240
Phe Met Lys Thr Ile Gln Arg Cys Asn Thr Gly Glu Arg Ser Leu Ser
65                  70                  75                  80 tta ctg aac tgt gag gag att aaa agc cag ttt gaa ggc ttt gtg aag     288
Leu Leu Asn Cys Glu Glu Ile Lys Ser Gln Phe Glu Gly Phe Val Lys
                85                  90                  95 gat ata atg tta aac aaa gag gag acg aag aaa gaa aac agc ttt gga     336
Asp Ile Met Leu Asn Lys Glu Glu Thr Lys Lys Glu Asn Ser Phe Gly
                100                 105                 110 ggg caa aaa ggt gat cag aat cct caa att gcg gca cat gtc ata agt     384
Gly Gln Lys Gly Asp Gln Asn Pro Gln Ile Ala Ala His Val Ile Ser
            115                 120                 125 gag gcc agc agt aaa aca aca tct gtg tta cag tgg gct gaa aaa gga     432
Glu Ala Ser Ser Lys Thr Thr Ser Val Leu Gln Trp Ala Glu Lys Gly
    130                 135                 140 tac tac acc atg agc aac aac ttg gta acc ctg gaa aat ggg aaa cag     480
Tyr Tyr Thr Met Ser Asn Asn Leu Val Thr Leu Glu Asn Gly Lys Gln
145                 150                 155                 160 ctg acc gtt aaa aga caa gga ctc tat tat atc tat gcc caa gtc acc     528
Leu Thr Val Lys Arg Gln Gly Leu Tyr Tyr Ile Tyr Ala Gln Val Thr
                165                 170                 175 ttc tgt tcc aat cgg gaa gct tcg agt caa gct cca ttt ata gcc agc     576
Phe Cys Ser Asn Arg Glu Ala Ser Ser Gln Ala Pro Phe Ile Ala Ser
                180                 185                 190 ctc tgc cta aag tcc ccc ggt aga ttc gag aga atc tta ctc aga gct     624
Leu Cys Leu Lys Ser Pro Gly Arg Phe Glu Arg Ile Leu Leu Arg Ala
            195                 200                 205 gca aat acc cac agt tcc gcc aaa cct tgc ggg caa caa tcc att cac     672
Ala Asn Thr His Ser Ser Ala Lys Pro Cys Gly Gln Gln Ser Ile His
    210                 215                 220 ttg gga gga gta ttt gaa ttg caa cca ggt gct tcg gtg ttt gtc aat     720
Leu Gly Gly Val Phe Glu Leu Gln Pro Gly Ala Ser Val Phe Val Asn
225                 230                 235                 240 gtg act gat cca agc caa gtg agc cat ggc act ggc ttc acg tcc ttt     768
Val Thr Asp Pro Ser Gln Val Ser His Gly Thr Gly Phe Thr Ser Phe
                245                 250                 255 ggc tta ctc aaa ctc tga                                             786
Gly Leu Leu Lys Leu
                260
```

<210> SEQ ID NO 38
<211> LENGTH: 261
<212> TYPE: PRT
<213> ORGANISM: artificial sequence
<220> FEATURE:
<223> OTHER INFORMATION: mutCD40L

<400> SEQUENCE: 38

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Gly
            100                 105                 110

Gly Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 39
<211> LENGTH: 1878
<212> TYPE: DNA
<213> ORGANISM: artificial sequence
<220> FEATURE:
<223> OTHER INFORMATION: LS-GFP-C1/C2
<220> FEATURE:
<221> NAME/KEY: CDS
<222> LOCATION: (1)..(1878)
<223> OTHER INFORMATION: LS-GFP-C1/C2

<400> SEQUENCE: 39 atg ccg cgc ccc cgc ctg ctg gcc gcg ctg tgc ggc gcg ctg ctc tgc      48
Met Pro Arg Pro Arg Leu Leu Ala Ala Leu Cys Gly Ala Leu Leu Cys
1               5                   10                  15 gcc ccc agc ctc ctc gtc gcc ctg gat atc gtg agc aag ggc gag gag      96
Ala Pro Ser Leu Leu Val Ala Leu Asp Ile Val Ser Lys Gly Glu Glu
            20                  25                  30 ctg ttc acc ggg gtg gtg ccc atc ctg gtc gag ctg gac ggc gac gta     144
Leu Phe Thr Gly Val Val Pro Ile Leu Val Glu Leu Asp Gly Asp Val
        35                  40                  45 aac ggc cac aag ttc agc gtg tcc ggc gag ggc gag ggc gat gcc acc     192
Asn Gly His Lys Phe Ser Val Ser Gly Glu Gly Glu Gly Asp Ala Thr
```

```
            50                   55                   60
tac ggc aag ctg acc ctg aag ttc atc tgc acc acc ggc aag ctg ccc      240
Tyr Gly Lys Leu Thr Leu Lys Phe Ile Cys Thr Thr Gly Lys Leu Pro
 65                  70                  75                  80 gtg ccc tgg ccc acc ctc gtg acc acc ctg acc tac ggc gtg cag tgc      288
Val Pro Trp Pro Thr Leu Val Thr Thr Leu Thr Tyr Gly Val Gln Cys
                 85                  90                  95 ttc agc cgc tac ccc gac cac atg aag cag cac gac ttc ttc aag tcc      336
Phe Ser Arg Tyr Pro Asp His Met Lys Gln His Asp Phe Phe Lys Ser
            100                 105                 110 gcc atg ccc gaa ggc tac gtc cag gag cgc acc atc ttc ttc aag gac      384
Ala Met Pro Glu Gly Tyr Val Gln Glu Arg Thr Ile Phe Phe Lys Asp
        115                 120                 125 gac ggc aac tac aag acc cgc gcc gag gtg aag ttc gag ggc gac acc      432
Asp Gly Asn Tyr Lys Thr Arg Ala Glu Val Lys Phe Glu Gly Asp Thr
    130                 135                 140 ctg gtg aac cgc atc gag ctg aag ggc atc gac ttc aag gag gac ggc      480
Leu Val Asn Arg Ile Glu Leu Lys Gly Ile Asp Phe Lys Glu Asp Gly
145                 150                 155                 160 aac atc ctg ggg cac aag ctg gag tac aac tac aac agc cac aac gtc      528
Asn Ile Leu Gly His Lys Leu Glu Tyr Asn Tyr Asn Ser His Asn Val
                165                 170                 175 tat atc atg gcc gac aag cag aag aac ggc atc aag gtg aac ttc aag      576
Tyr Ile Met Ala Asp Lys Gln Lys Asn Gly Ile Lys Val Asn Phe Lys
            180                 185                 190 atc cgc cac aac atc gag gac ggc agc gtg cag ctc gcc gac cac tac      624
Ile Arg His Asn Ile Glu Asp Gly Ser Val Gln Leu Ala Asp His Tyr
        195                 200                 205 cag cag aac acc ccc atc ggc gac ggc ccc gtg ctg ctg ccc gac aac      672
Gln Gln Asn Thr Pro Ile Gly Asp Gly Pro Val Leu Leu Pro Asp Asn
    210                 215                 220 cac tac ctg agc acc cag tcc gcc ctg agc aaa gac ccc aac gag aag      720
His Tyr Leu Ser Thr Gln Ser Ala Leu Ser Lys Asp Pro Asn Glu Lys
225                 230                 235                 240 cgc gat cac atg gtc ctg ctg gag ttc gtg acc gcc gcc ggg atc act      768
Arg Asp His Met Val Leu Leu Glu Phe Val Thr Ala Ala Gly Ile Thr
                245                 250                 255 ctc ggc atg gac gag ctg tac aag cgg ccg ccc tcg tac acc tgc aca      816
Leu Gly Met Asp Glu Leu Tyr Lys Arg Pro Pro Ser Tyr Thr Cys Thr
            260                 265                 270 tgc ctt aag ggc tac gcg ggc aac cac tgt gag acg aaa tgt gtc gag      864
Cys Leu Lys Gly Tyr Ala Gly Asn His Cys Glu Thr Lys Cys Val Glu
        275                 280                 285 cca ctg ggc atg gag aat ggg aac att gcc aac tca cag atc gcc gcc      912
Pro Leu Gly Met Glu Asn Gly Asn Ile Ala Asn Ser Gln Ile Ala Ala
    290                 295                 300 tca tct gtg cgt gtg acc ttc ttg ggt ttg cag cat tgg gtc ccg gag      960
Ser Ser Val Arg Val Thr Phe Leu Gly Leu Gln His Trp Val Pro Glu
305                 310                 315                 320 ctg gcc cgc ctg aac cgc gca ggc atg gtc aat gcc tgg aca ccc agc     1008
Leu Ala Arg Leu Asn Arg Ala Gly Met Val Asn Ala Trp Thr Pro Ser
                325                 330                 335 agc aat gac gat aac ccc tgg atc cag gtg aac ctg ctg cgg agg atg     1056
Ser Asn Asp Asp Asn Pro Trp Ile Gln Val Asn Leu Leu Arg Arg Met
            340                 345                 350 tgg gta aca ggt gtg gtg acg caa ggt gcc agc cgc ttg gcc agt cat     1104
Trp Val Thr Gly Val Val Thr Gln Gly Ala Ser Arg Leu Ala Ser His
        355                 360                 365 gag tac ctg aag gcc ttc aag gtg gcc tac agc ctt aat gga cac gaa     1152
Glu Tyr Leu Lys Ala Phe Lys Val Ala Tyr Ser Leu Asn Gly His Glu
```

```
                    370               375               380
ttc gat ttc atc cat gat gtt aat aaa aaa cac aag gag ttt gtg ggt   1200
Phe Asp Phe Ile His Asp Val Asn Lys Lys His Lys Glu Phe Val Gly
385                 390               395                 400 aac tgg aac aaa aac gcg gtg cat gtc aac ctg ttt gag acc cct gtg   1248
Asn Trp Asn Lys Asn Ala Val His Val Asn Leu Phe Glu Thr Pro Val
            405                 410                 415 gag gct cag tac gtg aga ttg tac ccc acg agt tgc cac acg gcc tgc   1296
Glu Ala Gln Tyr Val Arg Leu Tyr Pro Thr Ser Cys His Thr Ala Cys
                420               425               430 act ctg cgc ttt gag cta ttg ggc tgt gag ctg aac gga tgc gcc aat   1344
Thr Leu Arg Phe Glu Leu Leu Gly Cys Glu Leu Asn Gly Cys Ala Asn
            435                 440                 445 ccc ctg ggc ctg aag aat aac agc atc cct gac aag cag atc acg gcc   1392
Pro Leu Gly Leu Lys Asn Asn Ser Ile Pro Asp Lys Gln Ile Thr Ala
450                 455                 460 tcc agc agc tac aag acc tgg ggc ttg cat ctc ttc agc tgg aac ccc   1440
Ser Ser Ser Tyr Lys Thr Trp Gly Leu His Leu Phe Ser Trp Asn Pro
465                 470                 475                 480 tcc tat gca cgg ctg gac aag cag ggc aac ttc aac gcc tgg gtt gcg   1488
Ser Tyr Ala Arg Leu Asp Lys Gln Gly Asn Phe Asn Ala Trp Val Ala
                485                 490                 495 ggg agc tac ggt aac gat cag tgg ctg cag gtg gac ctg ggc tcc tcg   1536
Gly Ser Tyr Gly Asn Asp Gln Trp Leu Gln Val Asp Leu Gly Ser Ser
            500                 505                 510 aag gag gtg aca ggc atc atc acc cag ggg gcc cgt aac ttt ggc tct   1584
Lys Glu Val Thr Gly Ile Ile Thr Gln Gly Ala Arg Asn Phe Gly Ser
            515                 520                 525 gtc cag ttt gtg gca tcc tac aag gtt gcc tac agt aat gac agt gcg   1632
Val Gln Phe Val Ala Ser Tyr Lys Val Ala Tyr Ser Asn Asp Ser Ala
530                 535                 540 aac tgg act gag tac cag gac ccc agg act ggc agc agt aag atc ttc   1680
Asn Trp Thr Glu Tyr Gln Asp Pro Arg Thr Gly Ser Ser Lys Ile Phe
545                 550                 555                 560 cct ggc aac tgg gac aac cac tcc cac aag aag aac ttg ttt gag acg   1728
Pro Gly Asn Trp Asp Asn His Ser His Lys Lys Asn Leu Phe Glu Thr
                565                 570                 575 ccc atc ctg gct cgc tat gtg cgc atc ctg cct gta gcc tgg cac aac   1776
Pro Ile Leu Ala Arg Tyr Val Arg Ile Leu Pro Val Ala Trp His Asn
            580                 585                 590 cgc atc gcc ctg cgc ctg gag ctg ctg ggc tgt ttc gaa caa aaa ctc   1824
Arg Ile Ala Leu Arg Leu Glu Leu Leu Gly Cys Phe Glu Gln Lys Leu
            595                 600                 605 atc tca gaa gag gat ctg aat atg cat acc ggt cat cat cac cat cac   1872
Ile Ser Glu Glu Asp Leu Asn Met His Thr Gly His His His His His
610                 615                 620 cat tga                                                            1878
His
625

<210> SEQ ID NO 40
<211> LENGTH: 625
<212> TYPE: PRT
<213> ORGANISM: artificial sequence
<220> FEATURE:
<223> OTHER INFORMATION: LS-GFP-C1/C2

<400> SEQUENCE: 40

Met Pro Arg Pro Arg Leu Leu Ala Ala Leu Cys Gly Ala Leu Leu Cys
1               5                   10                  15

Ala Pro Ser Leu Leu Val Ala Leu Asp Ile Val Ser Lys Gly Glu Glu
```

```
            20                  25                  30
Leu Phe Thr Gly Val Val Pro Ile Leu Val Glu Leu Asp Gly Asp Val
        35                  40                  45

Asn Gly His Lys Phe Ser Val Ser Gly Glu Gly Glu Gly Asp Ala Thr
 50                  55                  60

Tyr Gly Lys Leu Thr Leu Lys Phe Ile Cys Thr Thr Gly Lys Leu Pro
 65                  70                  75                  80

Val Pro Trp Pro Thr Leu Val Thr Thr Leu Thr Tyr Gly Val Gln Cys
                 85                  90                  95

Phe Ser Arg Tyr Pro Asp His Met Lys Gln His Asp Phe Phe Lys Ser
             100                 105                 110

Ala Met Pro Glu Gly Tyr Val Gln Glu Arg Thr Ile Phe Phe Lys Asp
         115                 120                 125

Asp Gly Asn Tyr Lys Thr Arg Ala Glu Val Lys Phe Glu Gly Asp Thr
     130                 135                 140

Leu Val Asn Arg Ile Glu Leu Lys Gly Ile Asp Phe Lys Glu Asp Gly
145                 150                 155                 160

Asn Ile Leu Gly His Lys Leu Glu Tyr Asn Tyr Asn Ser His Asn Val
                 165                 170                 175

Tyr Ile Met Ala Asp Lys Gln Lys Asn Gly Ile Lys Val Asn Phe Lys
             180                 185                 190

Ile Arg His Asn Ile Glu Asp Gly Ser Val Gln Leu Ala Asp His Tyr
         195                 200                 205

Gln Gln Asn Thr Pro Ile Gly Asp Gly Pro Val Leu Leu Pro Asp Asn
     210                 215                 220

His Tyr Leu Ser Thr Gln Ser Ala Leu Ser Lys Asp Pro Asn Glu Lys
225                 230                 235                 240

Arg Asp His Met Val Leu Leu Glu Phe Val Thr Ala Ala Gly Ile Thr
                 245                 250                 255

Leu Gly Met Asp Glu Leu Tyr Lys Arg Pro Pro Ser Tyr Thr Cys Thr
             260                 265                 270

Cys Leu Lys Gly Tyr Ala Gly Asn His Cys Glu Thr Lys Cys Val Glu
         275                 280                 285

Pro Leu Gly Met Glu Asn Gly Asn Ile Ala Asn Ser Gln Ile Ala Ala
     290                 295                 300

Ser Ser Val Arg Val Thr Phe Leu Gly Leu Gln His Trp Val Pro Glu
305                 310                 315                 320

Leu Ala Arg Leu Asn Arg Ala Gly Met Val Asn Ala Trp Thr Pro Ser
                 325                 330                 335

Ser Asn Asp Asp Asn Pro Trp Ile Gln Val Asn Leu Leu Arg Arg Met
             340                 345                 350

Trp Val Thr Gly Val Val Thr Gln Gly Ala Ser Arg Leu Ala Ser His
         355                 360                 365

Glu Tyr Leu Lys Ala Phe Lys Val Ala Tyr Ser Leu Asn Gly His Glu
     370                 375                 380

Phe Asp Phe Ile His Asp Val Asn Lys Lys His Lys Glu Phe Val Gly
385                 390                 395                 400

Asn Trp Asn Lys Asn Ala Val His Val Asn Leu Phe Glu Thr Pro Val
                 405                 410                 415

Glu Ala Gln Tyr Val Arg Leu Tyr Pro Thr Ser Cys His Thr Ala Cys
             420                 425                 430

Thr Leu Arg Phe Glu Leu Leu Gly Cys Glu Leu Asn Gly Cys Ala Asn
         435                 440                 445
```

-continued

Pro Leu Gly Leu Lys Asn Asn Ser Ile Pro Asp Lys Gln Ile Thr Ala
    450                 455                 460

Ser Ser Ser Tyr Lys Thr Trp Gly Leu His Leu Phe Ser Trp Asn Pro
465                 470                 475                 480

Ser Tyr Ala Arg Leu Asp Lys Gln Gly Asn Phe Asn Ala Trp Val Ala
                485                 490                 495

Gly Ser Tyr Gly Asn Asp Gln Trp Leu Gln Val Asp Leu Gly Ser Ser
                500                 505                 510

Lys Glu Val Thr Gly Ile Ile Thr Gln Gly Ala Arg Asn Phe Gly Ser
            515                 520                 525

Val Gln Phe Val Ala Ser Tyr Lys Val Ala Tyr Ser Asn Asp Ser Ala
    530                 535                 540

Asn Trp Thr Glu Tyr Gln Asp Pro Arg Thr Gly Ser Ser Lys Ile Phe
545                 550                 555                 560

Pro Gly Asn Trp Asp Asn His Ser His Lys Lys Asn Leu Phe Glu Thr
                565                 570                 575

Pro Ile Leu Ala Arg Tyr Val Arg Ile Leu Pro Val Ala Trp His Asn
                580                 585                 590

Arg Ile Ala Leu Arg Leu Glu Leu Leu Gly Cys Phe Glu Gln Lys Leu
            595                 600                 605

Ile Ser Glu Glu Asp Leu Asn Met His Thr Gly His His His His His
    610                 615                 620

His
625

<210> SEQ ID NO 41
<211> LENGTH: 30
<212> TYPE: DNA
<213> ORGANISM: artificial sequence
<220> FEATURE:
<223> OTHER INFORMATION: primer

<400> SEQUENCE: 41
tatgatatcg tgagcaaggg cgaggagctg                                     30

<210> SEQ ID NO 42
<211> LENGTH: 31
<212> TYPE: DNA
<213> ORGANISM: artificial sequence
<220> FEATURE:
<223> OTHER INFORMATION: primer

<400> SEQUENCE: 42
atagcggccg cttgtacagc tcgtccatgc c                                   31

<210> SEQ ID NO 43
<211> LENGTH: 32
<212> TYPE: DNA
<213> ORGANISM: artificial sequence
<220> FEATURE:
<223> OTHER INFORMATION: primer

<400> SEQUENCE: 43
tatgcggccg ccctcgtaca cctgcacgtg cc                                  32

<210> SEQ ID NO 44
<211> LENGTH: 33
<212> TYPE: DNA
<213> ORGANISM: artificial sequence
<220> FEATURE:
<223> OTHER INFORMATION: primer -continued

<400> SEQUENCE: 44
gaaggattcg aaacagccca gcagctccag gcg            33

<210> SEQ ID NO 45
<211> LENGTH: 396
<212> TYPE: DNA
<213> ORGANISM: artificial sequence
<220> FEATURE:
<223> OTHER INFORMATION: hLact28-Myc/His

<400> SEQUENCE: 45
atgccgcgcc cccgcctgct ggccgcgctg tgcggcgcgc tgctctgcgc ccccagcctc      60
ctcgtcgccc tggatatctg ttccaaaaac ccctgccaca acggtggttt atgcgaggag     120
atttcccaag aagtgcgagg agatgtcttc ccctcgtaca cctgcacgtg ccttaagggc     180
tacgcgggca accactgtga gacgaaatgt gtcgagccac tgggcatgga gaatgggaac     240
attgccaact cacagatcgc cgcctcatct gtgcgtgtga ccttcttggg tttgcagcat     300
tggcggccgc tcgagtctag agggcccttc gaacaaaaac tcatctcaga agaggatctg     360
aatatgcata ccggtcatca tcaccatcac cattga                              396

<210> SEQ ID NO 46
<211> LENGTH: 36
<212> TYPE: DNA
<213> ORGANISM: artificial sequence
<220> FEATURE:
<223> OTHER INFORMATION: primer

<400> SEQUENCE: 46
aaggaagcgg ccgccaatgc tgcaaaccca agaagg         36

<210> SEQ ID NO 47
<211> LENGTH: 867
<212> TYPE: DNA
<213> ORGANISM: artificial sequence
<220> FEATURE:
<223> OTHER INFORMATION: LS-GFP-Myc/His
<220> FEATURE:
<221> NAME/KEY: CDS
<222> LOCATION: (1)..(867)
<223> OTHER INFORMATION: LS-GFP-Myc/His

<400> SEQUENCE: 47

```
atg ccg cgc ccc cgc ctg ctg gcc gcg ctg tgc ggc gcg ctg ctc tgc      48
Met Pro Arg Pro Arg Leu Leu Ala Ala Leu Cys Gly Ala Leu Leu Cys
1               5                   10                  15 gcc ccc agc ctc ctc gtc gcc ctg gat atc gtg agc aag ggc gag gag      96
Ala Pro Ser Leu Leu Val Ala Leu Asp Ile Val Ser Lys Gly Glu Glu
            20                  25                  30 ctg ttc acc ggg gtg gtg ccc atc ctg gtc gag ctg gac ggc gac gta     144
Leu Phe Thr Gly Val Val Pro Ile Leu Val Glu Leu Asp Gly Asp Val
        35                  40                  45 aac ggc cac aag ttc agc gtg tcc ggc gag ggc gag ggc gat gcc acc     192
Asn Gly His Lys Phe Ser Val Ser Gly Glu Gly Glu Gly Asp Ala Thr
    50                  55                  60 tac ggc aag ctg acc ctg aag ttc atc tgc acc acc ggc aag ctg ccc     240
Tyr Gly Lys Leu Thr Leu Lys Phe Ile Cys Thr Thr Gly Lys Leu Pro
65                  70                  75                  80 gtg ccc tgg ccc acc ctc gtg acc acc ctg acc tac ggc gtg cag tgc     288
Val Pro Trp Pro Thr Leu Val Thr Thr Leu Thr Tyr Gly Val Gln Cys
                85                  90                  95 ttc agc cgc tac ccc gac cac atg aag cag cac gac ttc ttc aag tcc     336
Phe Ser Arg Tyr Pro Asp His Met Lys Gln His Asp Phe Phe Lys Ser
```

```
gcc atg ccc gaa ggc tac gtc cag gag cgc acc atc ttc ttc aag gac    384
Ala Met Pro Glu Gly Tyr Val Gln Glu Arg Thr Ile Phe Phe Lys Asp
        115                 120                 125 gac ggc aac tac aag acc cgc gcc gag gtg aag ttc gag ggc gac acc    432
Asp Gly Asn Tyr Lys Thr Arg Ala Glu Val Lys Phe Glu Gly Asp Thr
130                 135                 140 ctg gtg aac cgc atc gag ctg aag ggc atc gac ttc aag gag gac ggc    480
Leu Val Asn Arg Ile Glu Leu Lys Gly Ile Asp Phe Lys Glu Asp Gly
145                 150                 155                 160 aac atc ctg ggg cac aag ctg gag tac aac tac aac agc cac aac gtc    528
Asn Ile Leu Gly His Lys Leu Glu Tyr Asn Tyr Asn Ser His Asn Val
                165                 170                 175 tat atc atg gcc gac aag cag aag aac ggc atc aag gtg aac ttc aag    576
Tyr Ile Met Ala Asp Lys Gln Lys Asn Gly Ile Lys Val Asn Phe Lys
            180                 185                 190 atc cgc cac aac atc gag gac ggc agc gtg cag ctc gcc gac cac tac    624
Ile Arg His Asn Ile Glu Asp Gly Ser Val Gln Leu Ala Asp His Tyr
        195                 200                 205 cag cag aac acc ccc atc ggc gac ggc ccc gtg ctg ctg ccc gac aac    672
Gln Gln Asn Thr Pro Ile Gly Asp Gly Pro Val Leu Leu Pro Asp Asn
    210                 215                 220 cac tac ctg agc acc cag tcc gcc ctg agc aaa gac ccc aac gag aag    720
His Tyr Leu Ser Thr Gln Ser Ala Leu Ser Lys Asp Pro Asn Glu Lys
225                 230                 235                 240 cgc gat cac atg gtc ctg ctg gag ttc gtg acc gcc gcc ggg atc act    768
Arg Asp His Met Val Leu Leu Glu Phe Val Thr Ala Ala Gly Ile Thr
                245                 250                 255 ctc ggc atg gac gag ctg tac aag cgg ccg ttc gaa caa aaa ctc atc    816
Leu Gly Met Asp Glu Leu Tyr Lys Arg Pro Phe Glu Gln Lys Leu Ile
            260                 265                 270 tca gaa gag gat ctg aat atg cat acc ggt cat cat cac cat cac cat    864
Ser Glu Glu Asp Leu Asn Met His Thr Gly His His His His His His
        275                 280                 285 tga                                                                867

<210> SEQ ID NO 48
<211> LENGTH: 288
<212> TYPE: PRT
<213> ORGANISM: artificial sequence
<220> FEATURE:
<223> OTHER INFORMATION: LS-GFP-Myc/His

<400> SEQUENCE: 48

Met Pro Arg Pro Arg Leu Leu Ala Ala Leu Cys Gly Ala Leu Leu Cys
1               5                   10                  15

Ala Pro Ser Leu Leu Val Ala Leu Asp Ile Val Ser Lys Gly Glu Glu
            20                  25                  30

Leu Phe Thr Gly Val Val Pro Ile Leu Val Glu Leu Asp Gly Asp Val
        35                  40                  45

Asn Gly His Lys Phe Ser Val Ser Gly Glu Gly Glu Gly Asp Ala Thr
    50                  55                  60

Tyr Gly Lys Leu Thr Leu Lys Phe Ile Cys Thr Thr Gly Lys Leu Pro
65                  70                  75                  80

Val Pro Trp Pro Thr Leu Val Thr Thr Leu Thr Tyr Gly Val Gln Cys
                85                  90                  95

Phe Ser Arg Tyr Pro Asp His Met Lys Gln His Asp Phe Phe Lys Ser
            100                 105                 110

Ala Met Pro Glu Gly Tyr Val Gln Glu Arg Thr Ile Phe Phe Lys Asp
```

```
            115                 120                 125
Asp Gly Asn Tyr Lys Thr Arg Ala Glu Val Lys Phe Glu Gly Asp Thr
        130                 135                 140

Leu Val Asn Arg Ile Glu Leu Lys Gly Ile Asp Phe Lys Glu Asp Gly
145                 150                 155                 160

Asn Ile Leu Gly His Lys Leu Glu Tyr Asn Tyr Asn Ser His Asn Val
            165                 170                 175

Tyr Ile Met Ala Asp Lys Gln Lys Asn Gly Ile Lys Val Asn Phe Lys
        180                 185                 190

Ile Arg His Asn Ile Glu Asp Gly Ser Val Gln Leu Ala Asp His Tyr
            195                 200                 205

Gln Gln Asn Thr Pro Ile Gly Asp Gly Pro Val Leu Leu Pro Asp Asn
        210                 215                 220

His Tyr Leu Ser Thr Gln Ser Ala Leu Ser Lys Asp Pro Asn Glu Lys
225                 230                 235                 240

Arg Asp His Met Val Leu Leu Glu Phe Val Thr Ala Ala Gly Ile Thr
            245                 250                 255

Leu Gly Met Asp Glu Leu Tyr Lys Arg Pro Phe Glu Gln Lys Leu Ile
        260                 265                 270

Ser Glu Glu Asp Leu Asn Met His Thr Gly His His His His His His
        275                 280                 285

<210> SEQ ID NO 49
<211> LENGTH: 10
<212> TYPE: PRT
<213> ORGANISM: artificial sequence
<220> FEATURE:
<223> OTHER INFORMATION: MART1-derived peptide

<400> SEQUENCE: 49

Glu Leu Ala Gly Ile Gly Ile Leu Thr Val
1               5                   10

<210> SEQ ID NO 50
<211> LENGTH: 25
<212> TYPE: DNA
<213> ORGANISM: artificial sequence
<220> FEATURE:
<223> OTHER INFORMATION: primer

<400> SEQUENCE: 50
atggagacag acacactcct gctat                                        25

<210> SEQ ID NO 51
<211> LENGTH: 26
<212> TYPE: DNA
<213> ORGANISM: artificial sequence
<220> FEATURE:
<223> OTHER INFORMATION: primer

<400> SEQUENCE: 51 atggatttc aggtgcagat tttcag                                        26

<210> SEQ ID NO 52
<211> LENGTH: 27
<212> TYPE: DNA
<213> ORGANISM: artificial sequence
<220> FEATURE:
<223> OTHER INFORMATION: primer

<400> SEQUENCE: 52
atgragtcac akacycaggt cttyrta                                      27
```

<210> SEQ ID NO 53
<211> LENGTH: 27
<212> TYPE: DNA
<213> ORGANISM: artificial sequence
<220> FEATURE:
<223> OTHER INFORMATION: primer

<400> SEQUENCE: 53
atgaggkccc cwgctcagyt yctkggr                              27

<210> SEQ ID NO 54
<211> LENGTH: 24
<212> TYPE: DNA
<213> ORGANISM: artificial sequence
<220> FEATURE:
<223> OTHER INFORMATION: primer

<400> SEQUENCE: 54
atgaagttgc ctgttaggct gttg                                 24

<210> SEQ ID NO 55
<211> LENGTH: 33
<212> TYPE: DNA
<213> ORGANISM: artificial sequence
<220> FEATURE:
<223> OTHER INFORMATION: primer

<400> SEQUENCE: 55
agtacgtctc gtgctcactg gatggtggga aga                       33

<210> SEQ ID NO 56
<211> LENGTH: 45
<212> TYPE: DNA
<213> ORGANISM: artificial sequence
<220> FEATURE:
<223> OTHER INFORMATION: primer

<400> SEQUENCE: 56
agtacgtctc ggtttccaga kgtgacatyk tgatgaccca gtctc          45

<210> SEQ ID NO 57
<211> LENGTH: 26
<212> TYPE: DNA
<213> ORGANISM: artificial sequence
<220> FEATURE:
<223> OTHER INFORMATION: primer

<400> SEQUENCE: 57
atggratgsa gctgkgtmat sctctt                               26

<210> SEQ ID NO 58
<211> LENGTH: 26
<212> TYPE: DNA
<213> ORGANISM: artificial sequence
<220> FEATURE:
<223> OTHER INFORMATION: primer

<400> SEQUENCE: 58
atgracttcg ggytgagctk ggtttt                               26

<210> SEQ ID NO 59
<211> LENGTH: 25
<212> TYPE: DNA
<213> ORGANISM: artificial sequence
<220> FEATURE:
<223> OTHER INFORMATION: primer

<400> SEQUENCE: 59
atggctgtct tggggctgct cttct                                           25

<210> SEQ ID NO 60
<211> LENGTH: 35
<212> TYPE: DNA
<213> ORGANISM: artificial sequence
<220> FEATURE:
<223> OTHER INFORMATION: primer

<400> SEQUENCE: 60
agtacgtctc gctgactcag ggaagtagcc cttga                                35

<210> SEQ ID NO 61
<211> LENGTH: 38
<212> TYPE: DNA
<213> ORGANISM: artificial sequence
<220> FEATURE:
<223> OTHER INFORMATION: primer

<400> SEQUENCE: 61
agtacgtctc gctctgrggt scarctkswg sagtcwgg                             38

<210> SEQ ID NO 62
<211> LENGTH: 41
<212> TYPE: DNA
<213> ORGANISM: artificial sequence
<220> FEATURE:
<223> OTHER INFORMATION: primer

<400> SEQUENCE: 62
cgagtacgtc tcgctccaca cccaggrrcc agtggataga c                         41

<210> SEQ ID NO 63
<211> LENGTH: 32
<212> TYPE: DNA
<213> ORGANISM: artificial sequence
<220> FEATURE:
<223> OTHER INFORMATION: primer

<400> SEQUENCE: 63
agtataagct tatgaagttg cctgttaggc tg                                   32

<210> SEQ ID NO 64
<211> LENGTH: 39
<212> TYPE: DNA
<213> ORGANISM: artificial sequence
<220> FEATURE:
<223> OTHER INFORMATION: primer

<400> SEQUENCE: 64
cgagacgact cgtctccaaa caggaagcca gaacatcag                            39

<210> SEQ ID NO 65
<211> LENGTH: 41
<212> TYPE: DNA
<213> ORGANISM: artificial sequence
<220> FEATURE:
<223> OTHER INFORMATION: primer

<400> SEQUENCE: 65
ggagacgagt cgtctcgaac gggctgatgc tgcaccaact g                         41

<210> SEQ ID NO 66
<211> LENGTH: 32

-continued

```
<212> TYPE: DNA
<213> ORGANISM: artificial sequence
<220> FEATURE:
<223> OTHER INFORMATION: primer

<400> SEQUENCE: 66
attattcgaa acactcattc ctgttgaagc tc                                    32

<210> SEQ ID NO 67
<211> LENGTH: 458
<212> TYPE: DNA
<213> ORGANISM: artificial sequence
<220> FEATURE:
<223> OTHER INFORMATION: LCJ-Myc/His

<400> SEQUENCE: 67
atgaagttgc ctgttaggct gttggtgctg atgttctggc ttcctgtttg gagacgagtc      60
gtctcgaacg ggctgatgct gcaccaactg tatccatctt cccaccatcc agtgagcagt     120
taacatctgg aggtgcctca gtcgtgtgct tcttgaacaa cttctacccc aaagacatca     180
atgtcaagtg gaagattgat ggcagtgaac gacaaaatgg cgtcctgaac agttgggctg     240
atcaggacag caaagacagc acctacagca tgagcagcac cctcacgttg accaaggacg     300
agtatgaacg acataacagc tatacctgtg aggccactca caagacatca acttcaccca     360
ttgtcaagag cttcaacagg aatgagtgtt cgaacaaaa actcatctca gaagaggatc     420
tgaatatgca taccggtcat catcaccatc accattga                             458

<210> SEQ ID NO 68
<211> LENGTH: 1150
<212> TYPE: DNA
<213> ORGANISM: artificial sequence
<220> FEATURE:
<223> OTHER INFORMATION: HCJ-Myc/His

<400> SEQUENCE: 68
atggaatgga gttggatatt tctctttctc ctgtcaggaa ctgcaggtgt ccactctgga      60
gacgagtcgt ctcgccaaaa cgacaccccc atcagtctat ccactggccc ctgggtgtgg    120
agatacaact ggttcctccg tgactctggg atgcctggtc aagggctact ccctgagtc     180 agtgactgtg acttggaact ctggatccct gtccagcagt gtgcacacct tcccagctct    240
cctgcagtct ggactctaca ctatgagcag ctcagtgact gtcccctcca gcacctggcc    300
aagtcagacc gtcacctgca gcgttgctca cccagccagc agcaccacgg tggacaaaaa    360
acttgagccc agcgggccca tttcaacaat caaccctgt cctccatgca aggagtgtca    420
caaatgccca gctcctaacc tcagggtgg accatccgtc ttcatcttcc ctccaaatat    480
caaggatgta ctcatgatct ccctgacacc caaggtcacg tgtgtggtgg tggatgtgag    540
cgaggatgac ccagacgtcc agatcagctg gtttgtgaac aacgtggaag tacacacagc    600
tcagacacaa acccatagag aggattacaa cagtactatc cgggtggtca gcaccctccc    660
catccggcac caggactgga tgagtggcaa ggagttcaaa tgcaaggtca acaacaaaga    720
cctcccatca cccatcgaga gaaccatctc aaaaattaaa gggctagtca gagctccaca    780
agtatacatc ttgccgccac cagcagagca gttgtccagg aaagatgtca gtctcacttg    840
cctggtcgtg ggcttcaacc ctggagacat cagtgtggag tggaccagca atgggcatac    900
agaggagaac tacaaggaca ccgcaccagt cctggactct gacggttctt acttcatata    960
tagcaagctc aatatgaaaa caagcaagtg ggagaaaaca gattccttct catgcaacgt   1020
gagacacgag ggtctgaaaa attactacct gaagaagacc atctcccggt ctccgggtaa   1080
```

```
attcgaacaa aaactcatct cagaagagga tctgaatatg cataccggtc atcatcacca    1140
tcaccattga                                                          1150
```

<210> SEQ ID NO 69
<211> LENGTH: 35
<212> TYPE: DNA
<213> ORGANISM: artificial sequence
<220> FEATURE:
<223> OTHER INFORMATION: primer

<400> SEQUENCE: 69

```
agtataagct tatggaatgg agttggatat ttctc                                35
```

<210> SEQ ID NO 70
<211> LENGTH: 40
<212> TYPE: DNA
<213> ORGANISM: artificial sequence
<220> FEATURE:
<223> OTHER INFORMATION: primer

<400> SEQUENCE: 70

```
cgagacgact cgtctccaga gtggacacct gcagttcctg                           40
```

<210> SEQ ID NO 71
<211> LENGTH: 36
<212> TYPE: DNA
<213> ORGANISM: artificial sequence
<220> FEATURE:
<223> OTHER INFORMATION: primer

<400> SEQUENCE: 71

```
ggagacgagt cgtctcgcca aaacgacacc cccatc                               36
```

<210> SEQ ID NO 72
<211> LENGTH: 29
<212> TYPE: DNA
<213> ORGANISM: artificial sequence
<220> FEATURE:
<223> OTHER INFORMATION: primer

<400> SEQUENCE: 72

```
attattcgaa tttacccgga gaccgggag                                       29
```

<210> SEQ ID NO 73
<211> LENGTH: 31
<212> TYPE: DNA
<213> ORGANISM: artificial sequence
<220> FEATURE:
<223> OTHER INFORMATION: primer

<400> SEQUENCE: 73

```
agtattcgaa tgaatctagg gcggccaatt c                                    31
```

<210> SEQ ID NO 74
<211> LENGTH: 30
<212> TYPE: DNA
<213> ORGANISM: artificial sequence
<220> FEATURE:
<223> OTHER INFORMATION: primer

<400> SEQUENCE: 74

```
agtaaccggt accctcacta aagggaagcg                                      30
```

<210> SEQ ID NO 75
<211> LENGTH: 357

```
<212> TYPE: DNA
<213> ORGANISM: artificial sequence
<220> FEATURE:
<223> OTHER INFORMATION: HV-M90/12

<400> SEQUENCE: 75
actctggggt gcagctggag cagtctgggg ctgagatggt gaggcctggg gcttcagtga      60
agttgtcctg caaggcttct ggctacacct tcaccagcta ctggatgcac tgggtgaagc    120
agaggcctgg acaaggcctt gagtggattg gtaagattga tccttctgat agtgaaactc    180
actacaatca aaagttcaag gacaaggcca cattgactgt agacaaatcc tccagcacag    240
cctacatgca gctcaacagc ctgacatctg aagactctgc ggtctattac tgtgcaagag    300
tctccttgct atggactact ggggtcaagg aacctcagtc accgtcttct cagccaa       357

<210> SEQ ID NO 76
<211> LENGTH: 335
<212> TYPE: DNA
<213> ORGANISM: artificial sequence
<220> FEATURE:
<223> OTHER INFORMATION: LV-M90/12

<400> SEQUENCE: 76
gtttccagat gtgacatttt gatgacccag tctcaaaaat tcatgtccac atcagtcgga     60
gacatagtca ccgtcgcctg caaggccagt cagaatgtgg gtagtaatgt agcctggtat    120
caacagaaac cagggcaatc tcctaaggca ctgatttact cggcttccta ccggtacagt    180
ggagtccctg atcgcttcac aggcagtgga tctgggacag atttcactct cattatcagt    240
aatgtgcagt ctgaagactt ggcagaatat ctctgtcagc aatatttcac ctatccgtac    300
acgttcggcg gggggaccaa gctggaaatc aaacg                               335

<210> SEQ ID NO 77
<211> LENGTH: 36
<212> TYPE: DNA
<213> ORGANISM: artificial sequence
<220> FEATURE:
<223> OTHER INFORMATION: primer

<400> SEQUENCE: 77
cgagtacgtc tcgcgtttka yttccagctt ggtscc                               36

<210> SEQ ID NO 78
<211> LENGTH: 36
<212> TYPE: DNA
<213> ORGANISM: artificial sequence
<220> FEATURE:
<223> OTHER INFORMATION: primer

<400> SEQUENCE: 78
cgagtacgtc tcgcgtttsa gctccarctt kgtccc                               36

<210> SEQ ID NO 79
<211> LENGTH: 37
<212> TYPE: DNA
<213> ORGANISM: artificial sequence
<220> FEATURE:
<223> OTHER INFORMATION: primer

<400> SEQUENCE: 79
cgagtacgtc tctcgttggc tgaggatacg ggaaccg                              37

<210> SEQ ID NO 80
<211> LENGTH: 35
```

```
<212> TYPE: DNA
<213> ORGANISM: artificial sequence
<220> FEATURE:
<223> OTHER INFORMATION: primer

<400> SEQUENCE: 80
cgagtacgtc tcgttggctg cagagacagt gcaac                              35

<210> SEQ ID NO 81
<211> LENGTH: 35
<212> TYPE: DNA
<213> ORGANISM: artificial sequence
<220> FEATURE:
<223> OTHER INFORMATION: primer

<400> SEQUENCE: 81
cgagtacgtc tcgttggctg agaagacggt gacyg                              35

<210> SEQ ID NO 82
<211> LENGTH: 768
<212> TYPE: DNA
<213> ORGANISM: artificial sequence
<220> FEATURE:
<223> OTHER INFORMATION: L-M90/12-IRES

<400> SEQUENCE: 82
atgaagttgc tgttaggct gttggtgctg atgttctggc ttcctgtttc cagatgtgac     60
attttgatga cccagtctca aaaattcatg tccacatcag tcggagacat agtcaccgtc   120
gcctgcaagg ccagtcagaa tgtgggtagt aatgtagcct ggtatcaaca gaaaccaggg   180
caatctccta aggcactgat ttactcggct tcctaccggt acagtggagt ccctgatcgc   240
ttcacaggca gtggatctgg gacagatttc actctcatta tcagtaatgt gcagtctgaa   300
gacttggcag aatatctctg tcagcaatat ttcacctatc cgtacacgtt cggcgggggg   360
accaagctgg aaatcaaacg ggctgatgct gcaccaactg tatccatctt cccaccatcc   420
agtgagcagt taacatctgg aggtgcctca gtcgtgtgct tcttgaacaa cttctacccc   480
aaagacatca atgtcaagtg gaagattgat ggcagtgaac gacaaaatgg cgtcctgaac   540
agttgggctg atcaggacag caaagacagc acctacagca tgagcagcac cctcacgttg   600
accaaggacg agtatgaacg acataacagc tatacctgtg aggccactca caagacatca   660 acttcacccca ttgtcaagag cttcaacagg aatgagtgtt cgaacaaaa actcatctca   720 gaagaggatc tgaatatgca taccggtcat catcaccatc accattga                 768

<210> SEQ ID NO 83
<211> LENGTH: 834
<212> TYPE: DNA
<213> ORGANISM: artificial sequence
<220> FEATURE:
<223> OTHER INFORMATION: L-M90/12-Myc/His

<400> SEQUENCE: 83
atgaagttgc tgttaggct gttggtgctg atgttctggc ttcctgtttc cagatgtgac     60
attttgatga cccagtctca aaaattcatg tccacatcag tcggagacat agtcaccgtc   120
gcctgcaagg ccagtcagaa tgtgggtagt aatgtagcct ggtatcaaca gaaaccaggg   180
caatctccta aggcactgat ttactcggct tcctaccggt acagtggagt ccctgatcgc   240
ttcacaggca gtggatctgg gacagatttc actctcatta tcagtaatgt gcagtctgaa   300
gacttggcag aatatctctg tcagcaatat ttcacctatc cgtacacgtt cggcgggggg   360
accaagctgg aaatcaaacg ggctgatgct gcaccaactg tatccatctt cccaccatcc   420
```

```
agtgagcagt taacatctgg aggtgcctca gtcgtgtgct tcttgaacaa cttctacccc    480
aaagacatca atgtcaagtg aagattgat ggcagtgaac gacaaaatgg cgtcctgaac     540
agttgggctg atcaggacag caaagacagc acctacagca tgagcagcac cctcacgttg    600
accaaggacg agtatgaacg acataacagc tatacctgtg aggccactca caagacatca    660
acttcaccca ttgtcaagag cttcaacagg aatgagtgtt tcgaacaaaa actcatctca    720
gaagaggatc tgaatatgca taccggtcat catcaccatc accatttcga acaaaaactc    780
atctcagaag aggatctgaa tatgcatacc ggtcatcatc accatcacca ttga           834

<210> SEQ ID NO 84
<211> LENGTH: 1548
<212> TYPE: DNA
<213> ORGANISM: artificial sequence
<220> FEATURE:
<223> OTHER INFORMATION: H-M90/12-Myc/His

<400> SEQUENCE: 84
atggaatgga gttggatatt tctctttctc ctgtcaggaa ctgcaggtgt ccactctggg     60
gtgcagctgg agcagtctgg ggctgagatg gtgaggcctg ggcttcagt gaagttgtcc    120 tgcaaggctt ctggctacac cttcaccagc tactggatgc actgggtgaa gcagaggcct    180
ggacaaggcc ttgagtggat tggtaagatt gatccttctg atagtgaaac tcactacaat    240
caaaagttca aggacaaggc cacattgact gtagacaaat cctccagcac agcctacatg    300
cagctcaaca gcctgacatc tgaagactct gcggtctatt actgtgcaag agtctcctat    360
gctatggact actggggtca aggaacctca gtcaccgtct tctcagccaa aacgacaccc    420
ccatcagtct atccactggc ccctgggtgt ggagatacaa ctggttcctc cgtgactctg    480
ggatgcctgg tcaagggcta cttccctgag tcagtgactg tgacttggaa ctctggatcc    540
ctgtccagca gtgtgcacac cttcccagct tcctgcagt ctggactcta cactatgagc     600
agctcagtga ctgtcccctc cagcacctgg ccaagtcaga ccgtcacctg cagcgttgct    660
cacccagcca gcagcaccac ggtggacaaa aaacttgagc ccagcgggcc catttcaaca    720
atcaacccct gtcctccatg caaggagtgt cacaaatgcc cagctcctaa cctcgagggt    780
ggaccatccg tcttcatctt ccctccaaat atcaaggatg tactcatgat ctccctgaca    840
cccaaggtca cgtgtgtggt ggtggatgtg agcgaggatg acccagacgt ccagatcagc    900
tggtttgtga acaacgtgga agtacacaca gctcagacac aaaccatag agaggattac     960 aacagtacta tccgggtggt cagcaccctc cccatccggc caggactg gatgagtggc     1020 aaggagttca atgcaaggt caacaacaaa gacctccat cacccatcga gagaaccatc     1080
tcaaaaatta agggctagt cagagctcca caagtataca tcttgccgcc accagcagag    1140
cagttgtcca ggaaagatgt cagtctcact tgcctggtcg tgggcttcaa ccctggagac    1200
atcagtgtgg agtggaccag caatgggcat acagaggaga actacaagga caccgcacca    1260
gtcctggact ctgacggttc ttacttcata tatagcaagc tcaatatgaa acaagcaag    1320 tgggagaaaa cagattcctt ctcatgcaac gtgagacaca agggtctgaa aaattactac    1380
ctgaagaaga ccatctcccg gtctccgggt aaattcgaac aaaaactcat ctcagaagag    1440
gatctgaata tgcataccgg tcatcatcac catcaccatt cgaacaaaaa actcatctca    1500
gaagaggatc tgaatatgca taccggtcat catcaccatc accattga                  1548

<210> SEQ ID NO 85
<211> LENGTH: 34
```

-continued

```
<212> TYPE: DNA
<213> ORGANISM: artificial sequence
<220> FEATURE:
<223> OTHER INFORMATION: primer

<400> SEQUENCE: 85
agtatctaga atggaatgga gttggatatt tctc                              34

<210> SEQ ID NO 86
<211> LENGTH: 33
<212> TYPE: DNA
<213> ORGANISM: artificial sequence
<220> FEATURE:
<223> OTHER INFORMATION: primer

<400> SEQUENCE: 86
agtagcggcc gctcatttac ccggagaccg gga                               33
```

METHODS AND COMPOUNDS FOR RAISING ANTIBODIES AND FOR SCREENING ANTIBODY REPERTOIRES

This application is the US national phase of international application PCT/IB2004/000888 filed 13 Feb. 2004 which designated the U.S. and claims benefit of U.S. Provisional Application No. 60/447,291, filed 14 Feb. 2003, the entire contents of each of which are hereby incorporated by reference.

The present invention relates to compositions and methods for raising antibodies generally comprising 1) providing highly immunogenic vesicles bearing at least one target antigen and 2) immunizing animals with the said antigen-bearing vesicles to induce antigen-specific antibody responses. The invention also relates to methods of screening antibody repertoires comprising 1) providing vesicles bearing at least one target antigen and one marker and 2) isolating antibody-producing cells or particles with defined antigen specificity using the said antigen- and marker-bearing vesicles. Antibodies with defined antigen specificity can then be prepared from isolated antibody-producing cells using known methods of the art. This invention can be used in experimental, research, therapeutic, prophylactic or diagnostic areas.

BACKGROUND

Antibodies are cornerstone proteins that play a critical role in the first line of defense against environmental intruders including microbes. They are research and diagnosis tools and most importantly can be used as therapeutic compounds. Numerous companies and research centers are today at different stages of development of antibody-based therapy candidates and several antibody drugs are already on the market.

The antibodies may be polyclonal or monoclonal. Methods of producing polyclonal antibodies from various species, including mice, rodents, primates, horses, pigs, rabbits, poultry, etc. may be found, for instance, in (1). Briefly, the antigen is injected in the presence of an adjuvant (for instance, complete or incomplete adjuvant e.g., Freund's adjuvant) and administered to an animal, typically by sub-cutaneous, intra-peritoneal, intra-venous or intramuscular injection. Repeated injections may be performed. Blood samples are collected and immunoglobulins or serum are separated.

The first method of producing monoclonal antibodies was established by Kohler and Milstein (2). This method is also described in detail, for instance, in (3). Briefly, this method comprises immunizing an animal with the antigen in the presence of an adjuvant, followed by the recovery of spleen or lymph node cells, which are then fused with inmortalized cells such as myeloma cells. The resulting hybridomas produce the monoclonal antibodies and can be selected by limit dilutions to isolate individual clones.

The preparation of antibodies has become essential for the evaluation of novel protein functions and in many cases, antibodies have grown to be therapeutic drugs. The interest for antibodies as therapeutic compounds was recently revived by the development of technologies for the generation of human and humanized antibodies. The many genome-sequencing programs in progress are providing a wealth of information necessitating the systematic preparation of antibodies against novel putative protein drug targets. This has created a costly bottleneck in the process of new drug target identification and has emphasized the need for a novel approach to streamline the process of monoclonal antibody preparation.

Indeed, the basic method of preparing monoclonal antibodies has several limitations. For instance, the preparation of hybridoma involves tedious, lengthy and inefficient processes of hybrid cells generation, drug-selection, screening and clonal expansion during which rare antibody-producing cells with the desired antigen specificity may be lost. Another difficulty is that rapid screening methods have to be developed to identify unique antibody-producing hybridoma in a large pool of hybridomas. These methods may vary with the nature of the target antigen and its availability. Yet another difficulty is that hybridomas can mainly be generated using cells from mouse or few other non-primate animals. Therefore, unless mice that are transgenic for the expression of human antibodies are used, hybridomas yield non-human antibodies that need to be transformed into humanized antibodies using recombinant DNA methods. The later process is required for therapeutic applications and can only be initiated once clones producing antibodies with desired specificity are obtained.

To address these limitations, two types of strategies have emerged, consisting of 1) improving specific steps of the classical approach described above and 2) developing antibody repertoires using recombinant DNA technology. The first strategy yielded, for instance, the SLAM technology (4) in which the need for preparation and screening of hybridoma is eliminated. The second strategy yielded, for instance, phage display technologies in which target proteins react with libraries of bacteriophage expressing antibodies or fragment thereof using a bacteriophage panning methods (5). More recently, the HuMY technology was developed by GeneTastix (U.S. Pat. No. 6,406,863) in which fragments of target proteins react with a library of antibody repertoire using a two-hybrid method in yeast.

Although improvements have been made, each method developed so far still has limitations. Notably, a major limitation for most methods is that they require large amounts of target protein for animal immunization and/or screening of hybridoma or bacteriophage libraries. Even in the case of the SLAM technology, which does not require the preparation and screening of hybridoma, large amounts of purified target proteins are still needed to perform plaque assays for isolating antibody-forming cells as described by the authors. The need for purification of recombinant proteins in large amounts hampers the rapid validation of multiple potential drug target proteins. In many instances, purification process varies from protein to protein, yields insufficient amounts of material, non-functional or denatured products. The purification process becomes even more problematic when dealing with membrane proteins or entities consisting of multiple polypeptide complexes.

Some phage display as well as two-hybrid methods use libraries of antigenic peptides and, thereby, alleviate the need for large-scale antigen purification. However, one deficiency with these methods is that antibodies against conformational epitopes are difficult to obtain and for instance, antibodies restricted to epitopes rising from multi-polypeptide entities such as anti-MHC/peptide complex antibodies cannot be obtained. Another limitation is that the sizes and qualities of the peptide libraries and of the antibody libraries used do not always allow isolating antibodies with high antigen-specific affinity. This is because affinity maturation of antibodies can only be performed if a first generation antibody is obtained. In contrast, the unlimited repertoire of antibody sequences found in mammals combined with the natural affinity maturation process occurring following repeated immunization of these animals provides the most efficient way to potentially generate antibodies against any epitope.

The present invention addresses the limitations of antibody preparation methods by providing a novel and effective approach. It also provides new valuable tools to improve existing methods of antibody preparation.

SUMMARY OF THE INVENTION

The present invention now discloses novel methods to produce antibodies that combine two technologies related to the display of antigen, adjuvant and/or markers on exosomes and to the use of exosomes as a vehicle for inducing potent humoral immune responses and/or for screening antibody repertoires.

Exosomes are vesicles of endosomal origin that are secreted in the extracellular milieu following fusion of late endosomal multivesicular bodies with the plasma membrane (6,7). Cells from various tissue types have been shown to secrete exosomes, such as dendritic cells, B lymphocytes, tumor cells and mast cells, for instance. Exosomes from different origin exhibit discrete sets of proteins and lipid moieties (8,9). They notably contain proteins involved in antigen presentation and immuno-modulation suggesting that exosomes play a role in cell-cell communications leading to the modulation of immune responses. Indeed, exosomes from dendritic cells (DC) pulsed with peptides derived from tumor antigens elicit anti-tumor responses in animal model using the matching tumor (10,11). Methods of producing, purifying or using exosomes for therapeutic purposes or as research tools have been described for instance in WO99/03499, WO00/44389 and WO97/05900, incorporated therein by reference. Recombinant exosomes have been described in the art, which derive from cells transfected with plasmids encoding recombinant proteins. Such recombinant exosomes contain the plasmid-encoded recombinant protein (WO00/28001).

Methods of manipulating the protein content of exosomes and of displaying antigens, adjuvant and markers for therapeutic purposes or as research tools have been described in WO03/016522.

The invention relates to a method of isolating single antibody-producing particles having specificity for a selected antigen, comprising:
1) preparing vesicles, preferably exosomes, displaying a selected antigen and a marker;
2) contacting or suspending said vesicles of step 1 with an antibody repertoire; and,
3) identifying and isolating single antibody-producing particles reacting with said vesicles.

In a specific embodiment, said antibody-producing particles are antibody-producing cells and said antibody repertoire is a repertoire of antibody-producing cells. Said antibody-producing cells can be plasma cells, hybridoma or lymphocytes. Preferably, said antibody-producing cells display the produced antibody. Said antibody repertoires are prepared by standard recombinant DNA approaches and that are for instances found in phage or yeast display libraries. Therefore, in an other embodiment, said antibody-producing particles are collection of phages or yeasts displaying specific antibodies. Said antibody-producing cells can also be antibody-secreting cells.

The invention relates to a method of identifying single antibody-producing cells having specificity for an antigen comprising:
1) providing antibody-producing cells;
2) preparing vesicles, preferably exosomes, displaying said antigen and a marker;
3) suspending the antibody-producing cells of step 1 with the vesicles of step 2; and,
4) identifying and isolating single antibody-producing cells reacting with said vesicles.

Preferably, said antibody-producing cells are lymphocytes. In a particular embodiment, said lymphocytes are collected from non-human animals immunized with said antigen.

If antibody-producing cells are antibody-secreting cells, the method further comprises, before the step of suspending the antibody-producing cells with the vesicles, the step of incubating antibody-producing cells with a first biotinylated-antibody against a ubiquitous cell surface marker such as CD81 or CD45, streptavidin and a second biotinylated antibody directed against immunoglobulin produced by said antibody-secreting cells. Optionally, said step comprises: 1) incubating the antibody-secreting cells with a first biotinylated-antibody against a ubiquitous cell surface marker and streptavidin; and 2) incubating the resulting antibody-secreting cells with the second biotinylated antibody directed against immunoglobulin of said antibody-secreting cells. Alternatively, said step comprises: 1) incubating streptavidin with a first biotinylated-antibody against a ubiquitous cell surface marker and a second biotinylated antibody directed against immunoglobulin of said antibody-secreting cells; and 2) incubating the resulting streptavidin bearing the first and the second antibodies with the antibody-secreting cells. Preferably, said antibody-secreting cells are selected from the group consisting of lymphocytes, hybridoma, and plasma cells.

The present invention discloses methods of isolating single antibody-producing cells comprising:
1) preparing immunogenic vesicles, preferably exosomes, displaying at least one antigen or an epitope thereof;
2) raising an antibody response by immunizing a non-human animal with said immunogenic vesicles;
3) collecting lymphocytes from an immunized animal;
4) preparing vesicles, preferably exosomes, displaying the said antigen or an epitope thereof of step 1 and a marker;
5) suspending the lymphocytes of step 3 with the vesicles of step 4; and,
6) identifying and isolating single antibody-producing cells reacting with the vesicles of step 4.

Optionally, said animals have been immunized with immunogens other than recombinant exosomes displaying antigens. These immunogens include commonly used antigen formulation such as purified recombinant antigens in adjuvant, nucleotide-based immunogens (naked-DNA, viral DNA) and cells or cell fractions containing antigens.

The invention relates to a method of isolating particles producing a single antibody specific of a variant antigen from an antibody repertoire comprising:
1) preparing a first population of vesicles, preferably exosomes, displaying said variant antigen and a marker;
2) preparing a second population of vesicles, preferably exosomes, displaying the native antigen and not displaying said marker;
3) suspending said antibody repertoire with the first and second populations of vesicles, the second population being in excess; and,
4) identifying and isolating single antibody-producing particles reacting with the vesicles of step 1.

The invention relates to a method of identifying cells producing a single antibody specific of a variant antigen comprising:

1) providing antibody-producing cells;
2) preparing vesicles, preferably exosomes, displaying said variant antigen used for the animal immunization and a marker;
3) preparing vesicles, preferably exosomes, displaying the native antigen and not displaying said marker;
4) suspending the antibody-producing cells of step 1 with the vesicles displaying said variant antigen and marker of step 2 and with an excess of the vesicles displaying said native antigen of step 3; and,
5) identifying and isolating single antibody-producing cells reacting with the vesicles of step 2.

Preferably, said antibody-producing cells are lymphocytes. In a particular embodiment, said lymphocytes are collected from non-human animals immunized with said antigen.

The present invention further discloses methods of isolating cells producing a single antibody specific of a variant antigen comprising:
1) preparing immunogenic vesicles, preferably exosomes, displaying a variant antigen;
2) raising an antibody response by immunizing a non-human animal with the said immunogenic vesicles;
3) collecting lymphocytes from immunized animal;
4) preparing vesicles, preferably exosomes, displaying said variant antigen of step 1 and a marker;
5) preparing vesicles, preferably exosomes, displaying the native antigen and not displaying said marker;
6) suspending the lymphocytes of step 3 with the vesicles displaying said variant antigen and marker of step 4 and with an excess of the vesicles displaying said native antigen of step 5; and,
7) identifying and isolating cells producing a single antibody specific of an antigen variant reacting with the vesicles of step 4.

Optionally, said methods further comprise the following steps: a) recovering DNA or RNA from said selected antibody producing particles, b) amplifying the nucleic acid sequence encoding immunoglobulin sequences or portions thereof, c) cloning the amplified nucleic acid sequence into an expression vector to produce proteins with desired antigen specificity.

In an embodiment of the above-disclosed methods of isolating antibody-producing cells according to the present invention, said antigen displayed by said vesicles is fused to an exosome targeting polypeptide. In an other embodiment, said antigen displayed by said vesicles is cross-linked to an exosome targeting polypeptide.

In an alternative embodiment of the above-disclosed methods of isolating antibody-producing cells according to the present invention, said antigen is a polypeptide having at least one transmembrane domain and said antigen is over-expressed into exosome-producing cells, thereby allowing the generation of recombinant exosomes displaying said antigen. Preferably, said polypeptide having at least one transmembrane domain is a receptor. More preferably, said receptor is a GPCR (G Protein-Coupled Receptor) such as SSTR2, CCR7, CXCR4 and CCR5.

Said antigen can be any protein, for example a receptor or an enzyme, or compounds other than polypeptides, such as glycolipids, polysaccharides, drugs and organic chemicals. Optionally, said antigen is an orphan receptor. Optionally, said antigen is a tumor, a viral or a microbial antigen. Alternatively, said antigen can be a MHC complex, more particularly a MHC I/peptide complex.

In a preferred embodiment of the above-disclosed methods of isolating cells producing a single antibody specific of a variant antigen according to the present invention, said variant antigen is a mutated antigen and said native antigen is a wild-type antigen. Optionally, said variant antigen is the antigen contacting molecules selected in the group consisting of polypeptide, lipid, DNA or small molecule, and said native antigen is the free antigen. Preferably said antigen contacting molecules is MHC/peptide complex. Hence, said variant antigen is an MHC/peptide complex and said native antigen unloaded MHC or MHC loaded with different peptides. In a particular embodiment, said variant antigen is an HLA-C/HIV peptide complex and said native antigen is an unloaded HLA-C or an HLA-C loaded with different peptides. By different peptides is intended peptide different from the first HIV peptide (preferably having less than 50, 30, 20 or 10% identity), for instance a peptide which is not derived from HIV. Alternatively, said variant antigen is ligand-receptor complex and said native antigen is either free ligand or free receptor. In a particular embodiment, said variant antigen includes gp120, CXCR4 and CD4 or gp120, CCR5 and CD4 and said native antigen is gp120. Additionally, said variant and native antigens can be different conformational states of any protein, including an enzyme.

In an other embodiment of the above-disclosed methods of isolating antibody-producing cells according to the present invention, said immunogenic vesicles further display immune accessory molecules. Preferably, said immune accessory molecules are adjuvant polypeptides. More preferably, said adjuvant polypeptides are cytokines such as GM-CSF, IL-2 and CD40L. Said CD40L is preferably a mutated CD40L, said mutation prevents cleavage and release of soluble CD40L. Optionally, said immune accessory molecules are also fused or cross-linked to an exosome targeting polypeptide. Preferably said soluble immune accessory molecules such as GM-CSF or IL-2 are fused to an exosome targeting polypeptide. Alternatively, said immune accessory molecules having at least one transmembrane domain are incorporated into immunogenic vesicles by over expression into the exosome-producing cells. Optionally, said immune accessory molecules are ligands for specific antigen delivery to antigen-presenting cells.

Optionally, said marker is a detectable molecule such as tags, enzyme, biotin, fluorescent molecules. Optionally, said marker is fused or cross-linked to an exosome targeting polypeptide. Alternatively, said marker has a transmembrane domain incorporated into immunogenic vesicles by over expression into the exosome-producing cells. Additionally, said marker is labeled lipids preferentially incorporated in vesicles, preferably exosomes. Preferably said labeled lipids are fluorophore-conjugated lipids such as Rhodamine-DOPE or Fluorescein-DOPE.

Optionally, the step of preparing vesicles, preferably exosomes, comprises the following steps:
a) Providing a genetic construct encoding said antigen;
b) Optionally, providing a construct encoding said marker;
c) Introducing said construct into exosome-producing cells to generate recombinant exosomes; and,
d) Collecting said recombinant exosomes, wherein said exosomes carry at their surface antigens encoded by said genetic construct and, optionally, said marker.

Optionally, several distinct genetic constructs-encoding distinct antigens are introduced into said exosome-producing cells. Preferably, said exosome-producing cells are mammalian cells. More preferably, said mammalian exosome-producing cells are murine cells.

Alternatively, the step of preparing vesicles, preferably exosomes, comprises the following steps:

a) Providing a molecule comprising said antigen fused to an exosome targeting polypeptide;
b) Optionally, providing a molecule comprising said marker fused to an exosome targeting polypeptide; and,
c) contacting said molecule comprising said antigen, and optionally said molecule comprising said marker, with lipid vesicles containing phosphatidyl serine or other lipids naturally contained in exosomes, to create functionalized lipid vesicles presenting said antigen, and optionally said marker, at their surface.

The invention further concerns the isolated antibody-producing particles, preferably cells, and their use for antibody production, and the antibodies produced by said antibody-producing particles, preferably cells. The invention also concerns a composition comprising either said isolated antibody-producing cells or said antibodies produced by said antibody-producing cells and a pharmaceutically acceptable excipient or carrier.

The invention further relates to a method of expressing a polypeptide having at least one transmembrane domain at the surface of exosomes, comprising:
1) Providing a genetic construct encoding said polypeptide or a portion thereof comprising at least one transmembrane domain;
2) Introducing said construct and over expressing said polypeptide or a portion thereof comprising at least one transmembrane domain into exosome-producing cells to generate recombinant exosomes; and
3) Collecting said recombinant exosomes, wherein said exosomes carry at their surface polypeptides encoded by said genetic construct In a preferred embodiment of this method, said polypeptide having at least one transmembrane domain is a receptor. More preferably, said receptor is a GPCR (G Protein-Coupled Receptor) such as SSTR2, CCR7, CXCR4 and CCR5. Alternatively, said polypeptide is a CD40L, preferably a mutated CD40L, said mutation prevents cleavage and release of soluble CD40L.

The invention concerns a functionalized exosome prepared by the above-described method, a composition comprising said functionalized exosome and any use of it. More particularly, the invention concerns a composition comprising said functionalized exosome and a pharmaceutically acceptable excipient or carrier. The invention also concerns the use of said functionalized exosome for producing antibody or for delivering the antigen to a subject.

Therefore, the invention concerns a method of producing an antibody that binds a polypeptide having at least one transmembrane domain or an epitope thereof, comprising:
a) Providing a genetic construct encoding said polypeptide or a portion thereof comprising at least one transmembrane domain;
b) Introducing said construct and over expressing said polypeptide or a portion thereof comprising at least one transmembrane domain into exosome-producing cells to generate recombinant exosomes presenting said polypeptide or epitope at their surface,
c) Collecting said recombinant exosomes and injecting said exosomes or a portion thereof to a non-human mammal to generate antibodies that bind said polypeptide or epitope and,
d) Collecting antibodies or antibody producing cells from said mammal.

In a preferred embodiment of this method, said polypeptide having at least one transmembrane domain is a receptor. More preferably, said receptor is a GPCR (G Protein-Coupled Receptor) such as SSTR2, CCR7, CXCR4 and CCR5. Preferably, said exosomes further display a mutated CD40L, said mutation prevents cleavage and release of soluble CD40L. Antibodies may then be isolated directly from animal serum for the preparation of polyclonal antibody. Monoclonal antibodies may also be prepared from these animals using traditional approaches including generation of hybridomas or isolation of single antibody-producing cells by methods such as SLAM.

The invention also concerns a method of delivering an antigen having at least one transmembrane domain or a portion thereof comprising at least one transmembrane domain to a subject comprising:
a) Providing a genetic construct encoding said antigen or a portion thereof comprising at least one transmembrane domain;
b) Introducing said construct and over expressing said antigen or a portion thereof comprising at least one transmembrane domain into exosome-producing cells to generate recombinant exosomes presenting said antigen or said portion thereof at their surface,
c) Collecting said recombinant exosomes and injecting said exosomes or a portion thereof to said subject.

In a preferred embodiment of this method, said antigen is a receptor. More preferably, said receptor is a GPCR (G Protein-Coupled Receptor) such as SSTR2, CCR7, CXCR4 and CCR5. Preferably, said exosomes further display a mutated CD40L, said mutation prevents cleavage and release of soluble CD40L.

The invention concerns a method of producing an immune response in a subject against a specific antigen having at least one transmembrane domain or a portion thereof comprising at least one transmembrane domain comprising:
a) Providing a genetic construct encoding said antigen or a portion thereof comprising at least one transmembrane domain;
b) Introducing said construct and over expressing said antigen or a portion thereof comprising at least one transmembrane domain into exosome-producing cells to generate recombinant exosomes presenting said antigen or said portion thereof at their surface,
c) Collecting said recombinant exosomes and injecting said exosomes or a portion thereof to said subject.

In a preferred embodiment of this method, said antigen is a receptor. More preferably, said receptor is a GPCR (G Protein-Coupled Receptor) such as SSTR2, CCR7, CXCR4 and CCR5. Preferably, said exosomes further display a mutated CD40L, said mutation prevents cleavage and release of soluble CD40L.

The invention further contemplates a method to biosynthetically label exosomes with fluorophore-conjugated lipids and a method for the cloning of inserts into plasmids without introducing mutation at the cloning sites.

LEGEND TO FIGURES

FIG. 1: ELISA detecting anti-Lactadherin antibody in sera of Lactadherin-immunized mice.

Figure 2:
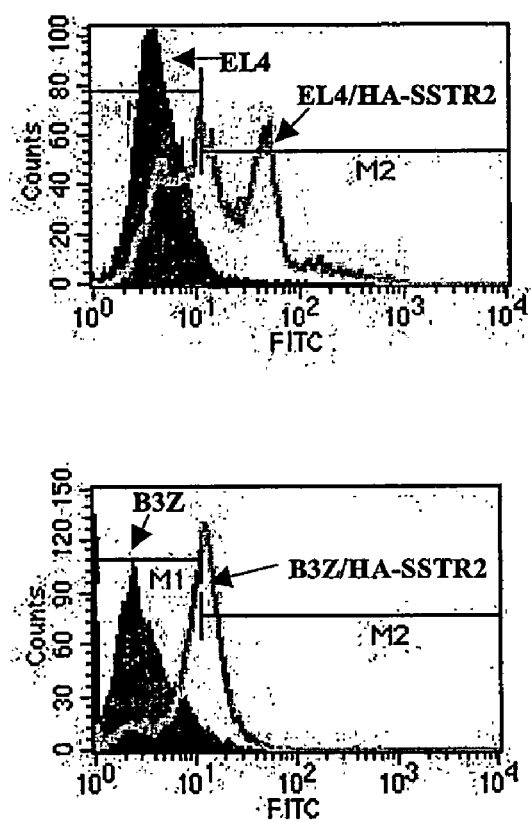

FIG. 2: FACS analysis of recombinant cells transfected with HApC3.1/SSTR2 and labelled with anti-HA tag antibody.

Figure 3:
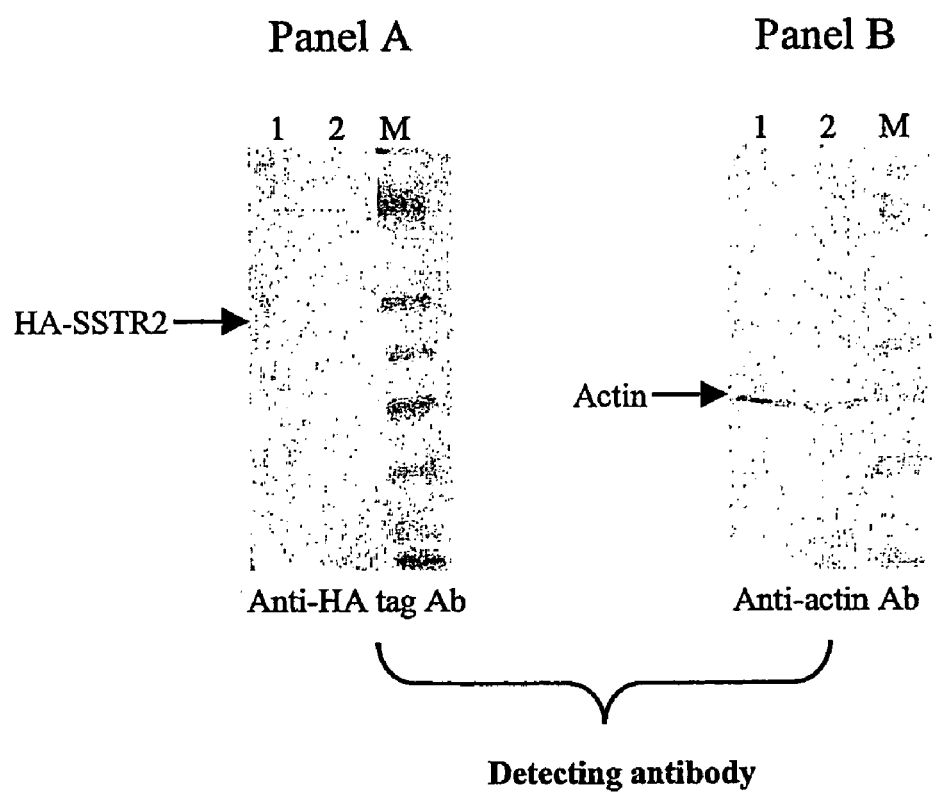

FIG. 3: Western blot analysis detecting HA-SSTR2 expressed in exosomes that are produced by HApC3.1/SSTR2-transfected cells.

Figure 4:
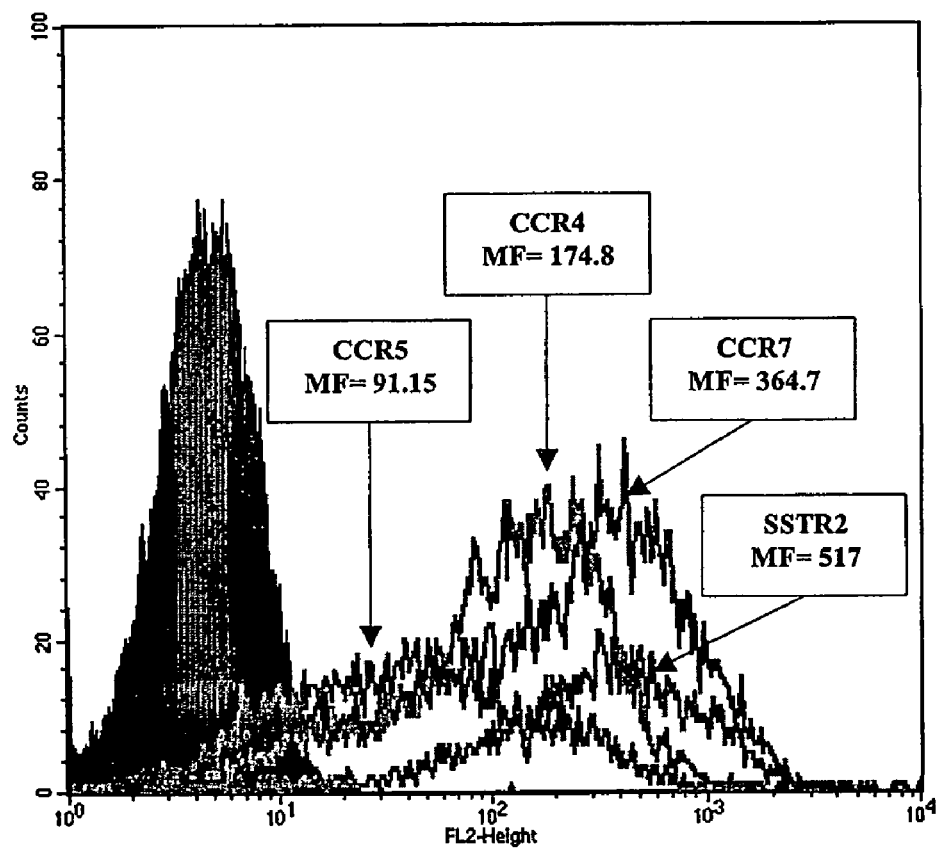

FIG. 4: FACS analysis of a panel of 293 cells transfected with various GPCR-encoding HApC3.1 and labelled with anti-HA tag antibody.

Figure 5:
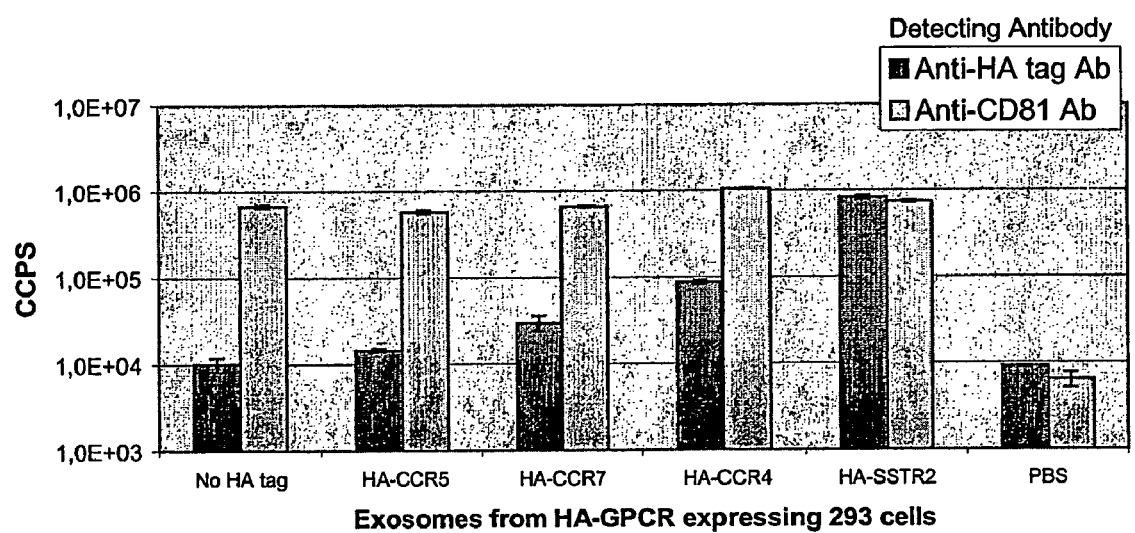

FIG. 5: Capture-ELISA detecting HA-GPCR expression on exosomes derived from a panel of 293 cells transfected with various GPCR-encoding HApC3.1.

Figure 6:
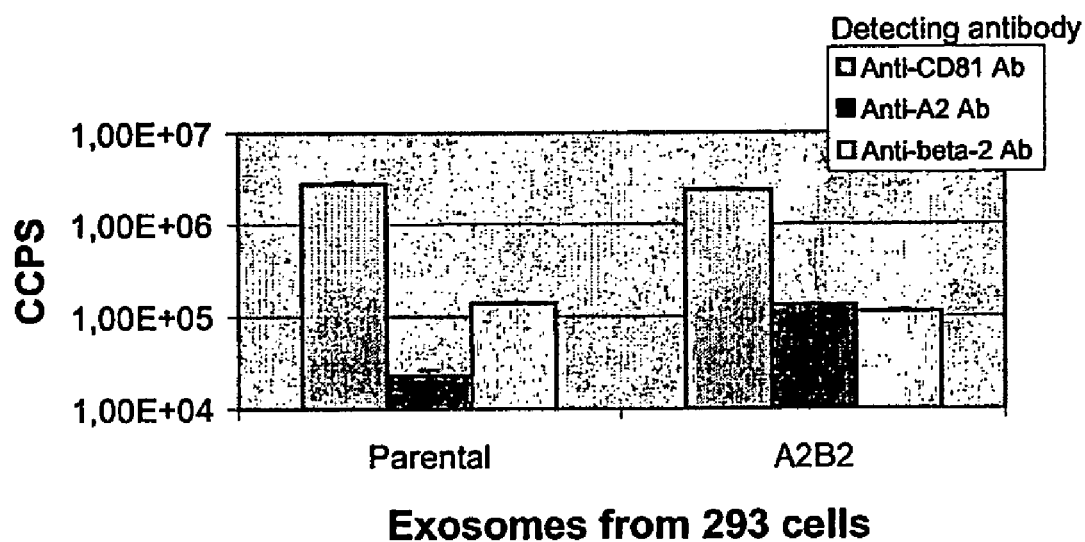

FIG. 6: Capture ELISA detecting HLA-A2 and β2-microglobulin expression on 293 exosomes.

Figure 7:
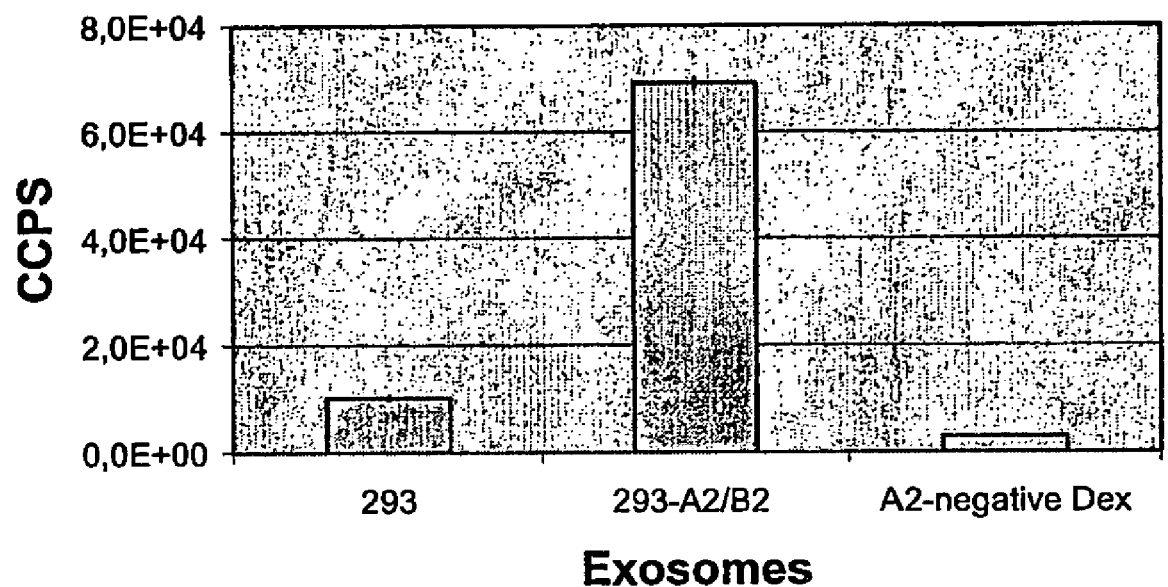

FIG. 7: Capture-ELISA detecting Reference peptide bound to HLA-A2 on exosomes.

Figure 8:
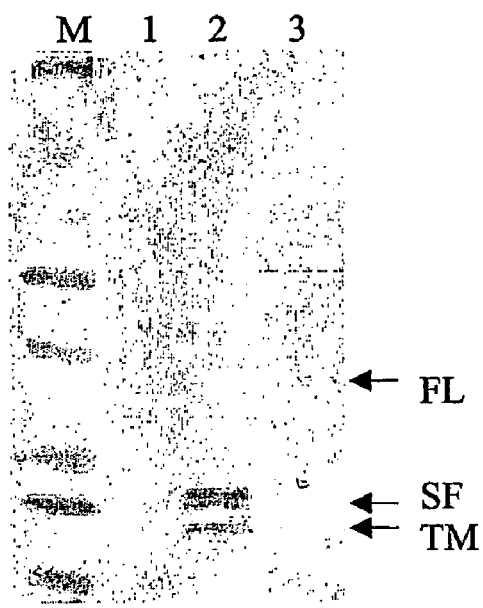

FIG. 8: Western Blot analysis detecting the expression of CD40L and mutCD40L on recombinant exosomes. Western blot analysis revealed that transfection of 293 cells with pcDNA6-CD40L and pcDNA6-mutCD40L resulted in the expression of CD40L expression in exosomes. Exosomes derived from CD40L-expressing 293 cells contained the full-length CD40L (FL on lane 2) as well as the products of its proteolytic cleavage consisting of the soluble form of CD40L (SF on lane 2) and the remaining N-terminal extremity that contains the trans-membrane domain of CD40L (TM on lane 2). In contrast, exosomes derived from mutCD40L-expressing 293 cells contained only the full-length form (FL on lane 3). No protein was detected in exosomes from parental 293 cells (lane 1).

Figure 9:
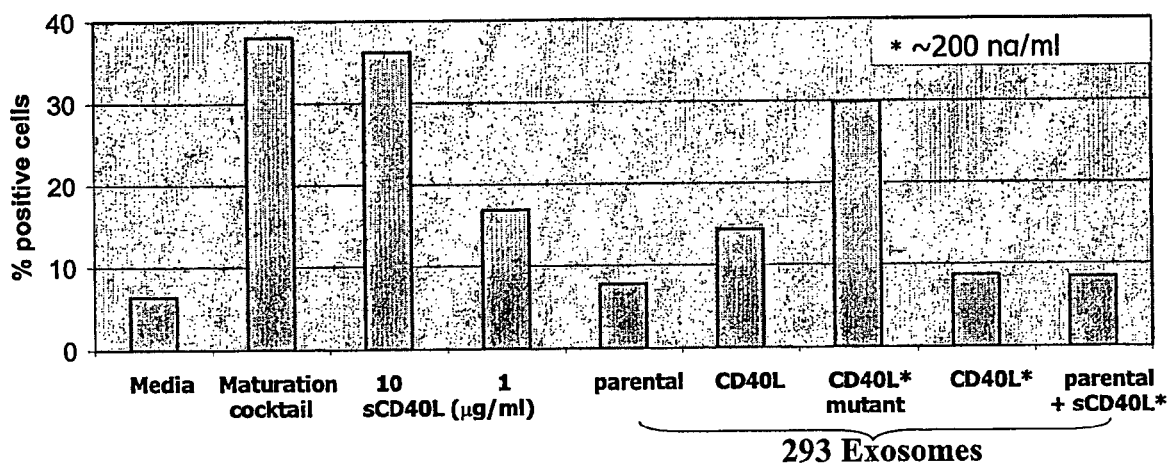

FIG. 9: DC-maturation assay measuring the biological activity of recombinant exosomes displaying CD40L.

Figure 10:
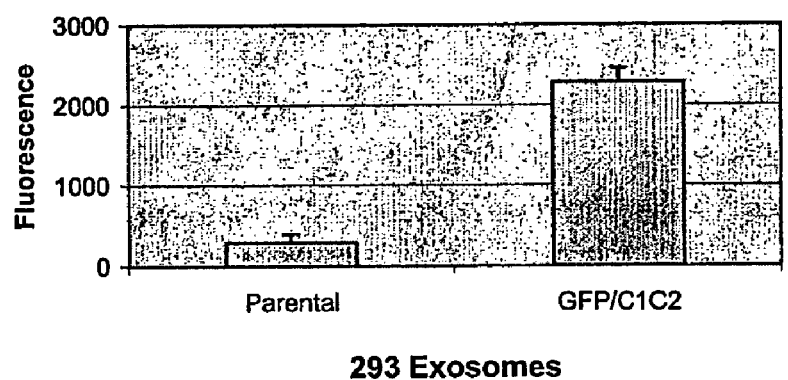

FIG. 10: Measurement of fluorescence associated with recombinant exosome expressing GFP/C1C2 chimeric protein.

Figure 11:
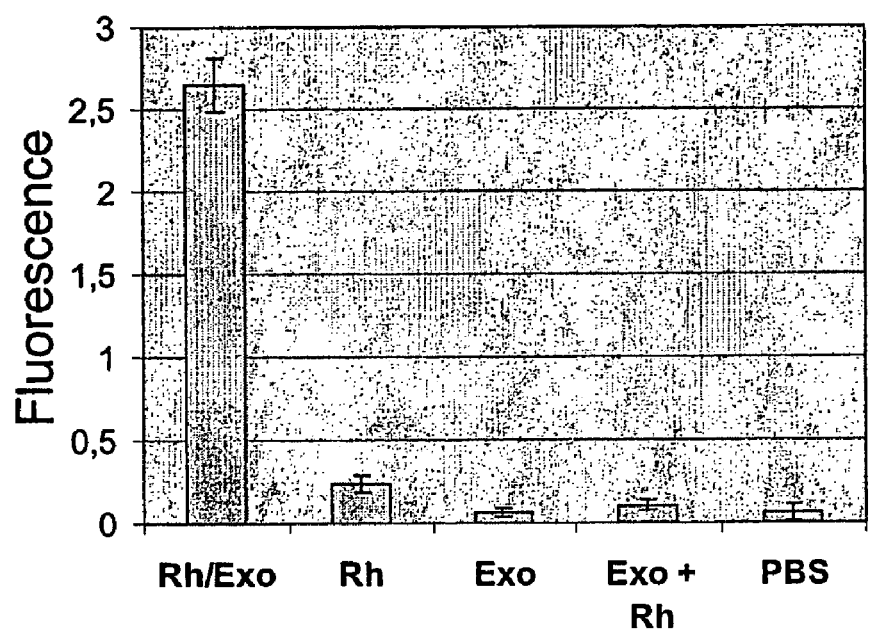

FIG. 11: Capture ELISA detecting fluorescence associated with exosomes derived from cells metabolically labeled with Rh-DOPE.

Figure 12:
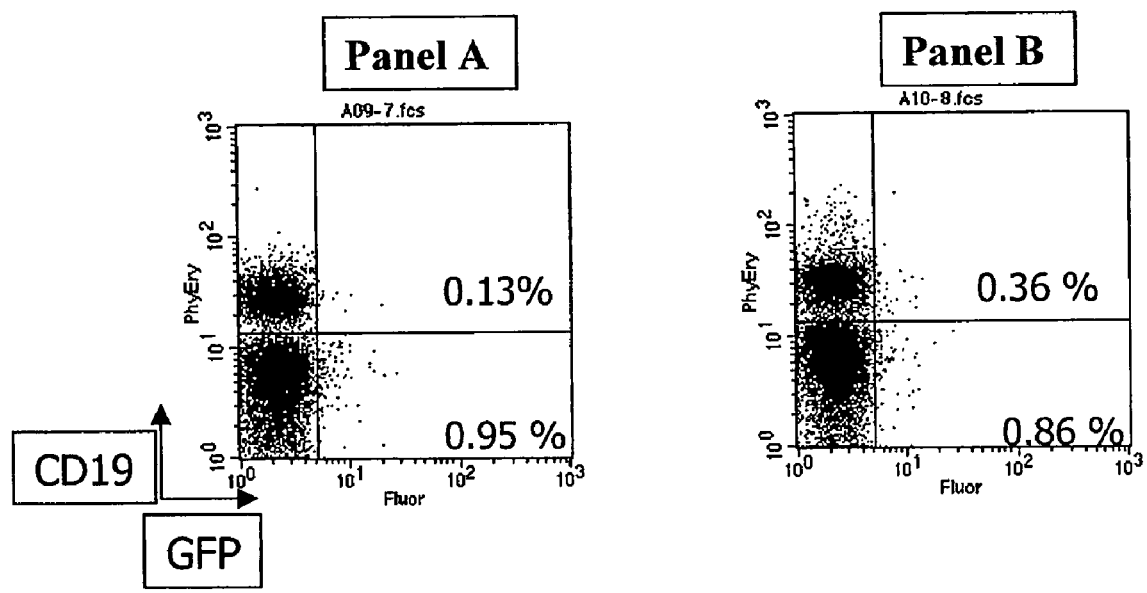

FIG. 12: FACS analysis detecting PLNC bearing GFP/CCR7-293 exosomes.

Figure 13:
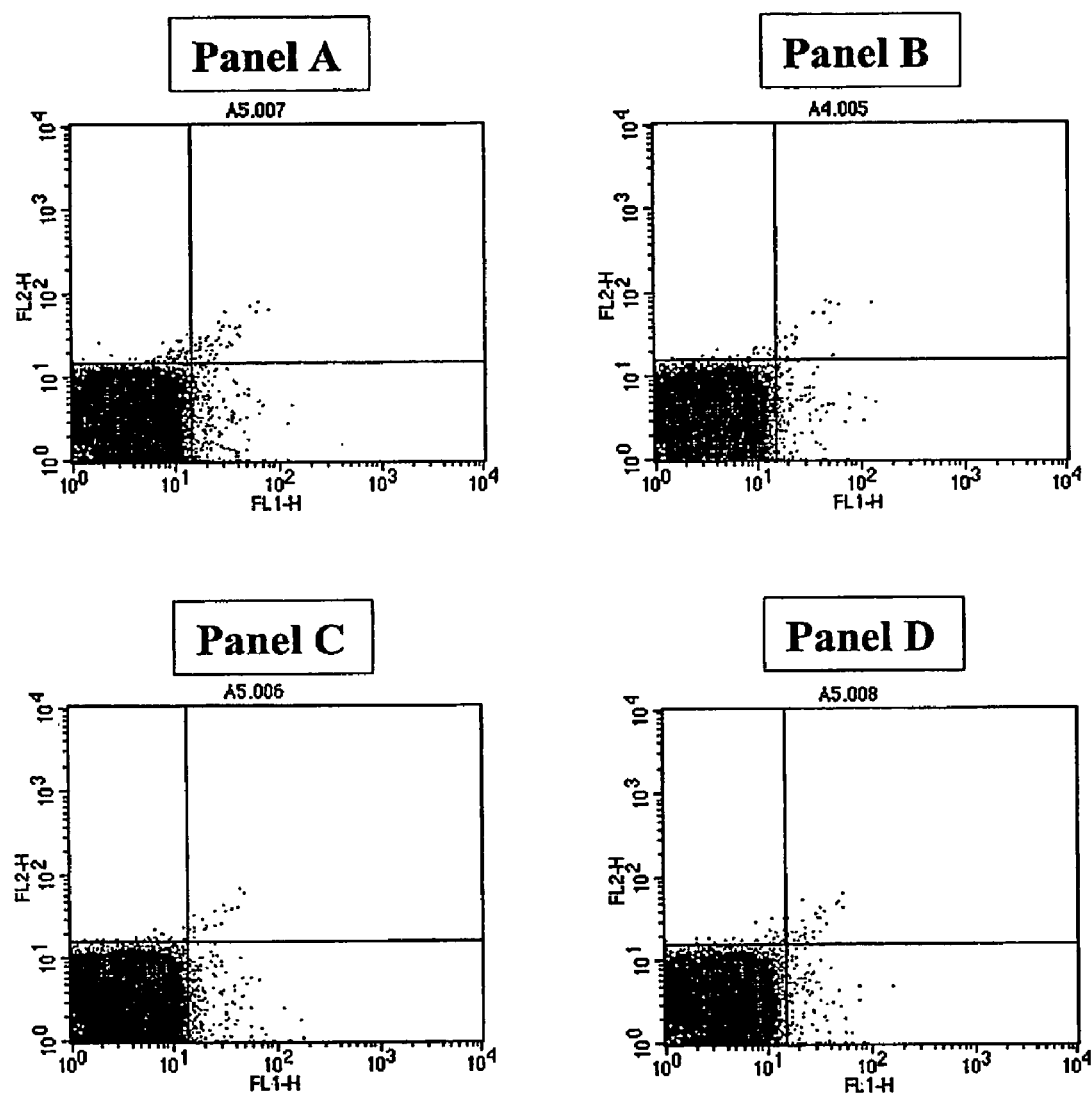

FIG. 13: FACS analysis detecting PLNC bearing GFP/A2/MART1-293 exosomes. The percentage of GFP-positive cells in the left PLNC population derived from the side of the mice immunized with A2/MART1-exosomes was significantly higher when cells were incubated with GFP/A2/MART1-293 exosomes than with GFP/A2-293 exosomes (Panel A, 0.83% positive cells vs Panel B, 0.33% positive cells). In contrast, no significant difference could be detected when comparing the right PLNC incubated with GFP/A2/MART1-293 and GFP/A2-293 (Panel C, 0.49% positive cells vs Panel D, 0.39% positive cells).

Figure 14:
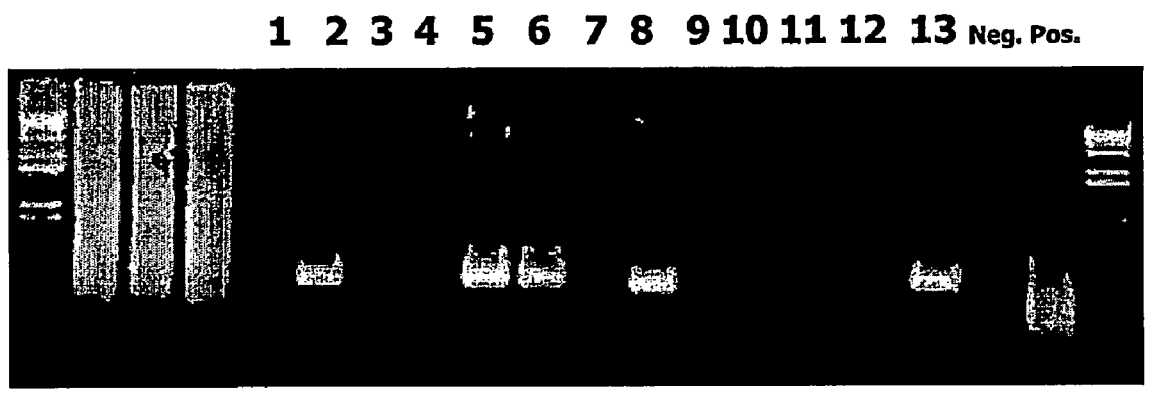

FIG. 14: Gel analysis of single cell-derived RT-PCR products based on their ability to bind fluorescent exosomes in an antigen-specific manner. Two rounds of PCR yielded detectable amounts of PCR products derived from several single cell cDNA (lane 2, 5, 6, 8 and 13). Sequencing of these PCR products confirmed that they encode the variable regions of immunoglobulins.

Figure 15:
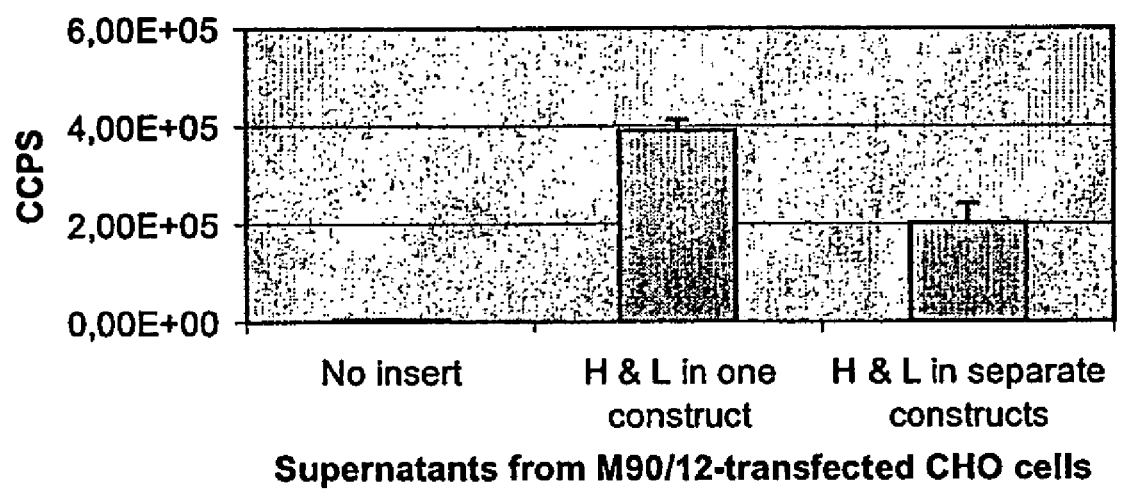

FIG. 15: Capture-ELISA detecting recombinant IgG in CHO-culture supernatants.

Figure 16:
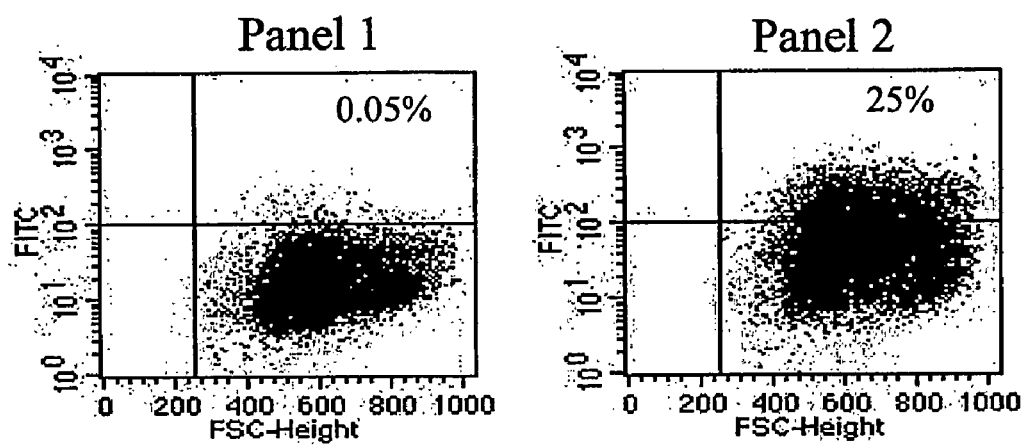

FIG. 16: FACS analysis of AbTrap– and + and – hybridoma producing anti-exosome antibodies. Incubation of biotinylated-exosomes with AbTrap– cells resulted in background fluorescence associated with these cells (panel 1). In contrast, ~25% of these cells were positive when bearing the full AbTrap (panel 2).

DETAILED DESCRIPTION OF THE INVENTION

The present invention discloses novel methods of raising antibodies and screening antibody repertoires. The invention more particularly uses membrane vesicles, of natural or synthetic origin, preferably exosomes, displaying target antigens, co-stimulatory molecules and/or markers. This invention can be used in experimental, research, therapeutic, prophylactic or diagnostic areas.

The present invention stems from the discovery of novel unexpected properties of recombinant chimeric proteins containing exosome-targeting domains and of recombinant membrane receptors. More particularly, the invention shows that antigens targeted to exosomes are highly immunogenic and yield potent humoral immune responses. In addition, it shows that exosomes displaying antigen and a marker can be conveniently used to isolate antigen-specific antibody-producing cells, even at low frequencies of responding cells.

The invention presents many advantages over traditional approaches of antibody preparation. It is most advantageous when dealing with poorly immunogenic antigens, membrane proteins or multi-component polypeptide complexes. It is notably suitable when dealing with difficult targets for which the preparation of antibody using traditional approach failed or does not produce useful antibodies. Also, the preparation of antibodies can be achieved without the need to purify large amounts of antigens. In fact, a single and small-scale purification method to isolate exosomes (U.S. Ser. No. 09/789,748) can be used regardless of the nature of the exogenous antigen expressed at their surface. Thus, the antigen preparation step can be completed very rapidly, i.e., typically within less than 12 hours. This method is rapid and can be performed on many samples in parallel allowing the simultaneous preparation of multiple antigens for immunization. The expression of antigens in a naturally occurring vesicle combined with a gentle purification procedure helps preserve the native conformation of antigens, which may enable the generation of relevant antibodies with potential therapeutic applications. Moreover, the invention generates lipid vesicles that contain a high density of antigen at their surface. This high density can be compared to a polymeric state, which highly favours antibody production by increasing antigen avidity. A further advantage of this invention is that the polypeptides can be expressed by exosome producing cells and thus subjected to natural pathways of processing and post-translational modifications (glycosylations, etc.). Another advantage is that antibody-producing cells can be isolated even when low frequencies of responding cells are generated. Such low frequencies generally occur following immunization with poorly immunogenic antigens or with low amounts of antigens. The sorting of B cells using exosome-bearing antigens allows isolating very rare antigen-specific antibody-producing cells. An added advantage of the sorting of B cells using exosome-bearing antigens is that the stringency and specificity of the sorting may be adjusted in order to selectively isolate B cells producing antibodies to unique epitopes or conformational epitopes. For instances, subtractive sorting performed in the presence of an excess of exosome-bearing a receptor and low amounts of traceable exosomes bearing the same receptor bound to its physiological ligand may allow isolating B cells producing antibody reacting with receptor/ligand complex only. Hence, the invention also allows generation of smart functional antibodies that can discriminate subtle conformational changes on the target antigen due to interaction with other compounds or to mutation/deletion. The latter feature is a considerable advantage over other antibody preparation methods.

Immunization with highly immunogenic compounds combined with the highly selective sorting of unique and rare antibody-producing cells provides an efficient novel method to produce antibodies against defined epitopes.

Method for Raising Antibodies

In this method, antibodies are raised when immunogenic vesicles, preferably exosomes, expressing at least one target antigen are introduced into an animal. The production of antibody may be evaluated by testing the serum of immunized-animal by standard approaches. The preparation of antibody may be accomplished by affinity purification of antibodies from the serum for polyclonal antibodies or by isolating antigen-specific antibody producing cells for monoclonal antibodies. The latter may preferably be performed using the method for screening antibody repertoires described below. Alternatively, monoclonal antibodies may be prepared using the various known approaches of monoclonal antibody preparation from immunized animal such as Hybridoma screening and SLAM.

Preparation of Immunogenic Vesicles Displaying Antigens

Immunogenic vesicles displaying antigens are generally prepared by fusing antigen sequences to exosome-targeting domains, preferably the C1C2 domain of Lactadherin. Immunogenic vesicles are natural or synthetic vesicles such as exosomes and liposomes. Methods for the preparation of vesicles bearing chimeric proteins that contain exosome targeting domains and their use are described in WO03/016522.

Lactadherin is almost exclusively found associated with exosomes. The C1/C2 domain of Lactadherin contains a highly specific targeting motif for exosome surfaces. Therefore, the introduction into a protein of part or the entirety of the C1 and/or C2 domain of Lactadherin or a functional equivalent thereof allows the targeting of the resulting chimeric protein to exosomes and other lipidic structures.

Therefore, said exosome targeting polypeptide comprises Lactadherin or a portion thereof comprising a functional C1 and/or C2 domain. In performing the present invention it is possible to use Lactadherin from various sources or origins. More preferably, said Lactadherin or a portion thereof is a non-human mammalian Lactadherin or a portion thereof. Mammalian Lactadherin includes murine, rat, bovine, porcine and equine Lactadherin, for instance. More particularly, said non-human mammalian Lactadherin or a portion thereof is selected from: (i) murine Lactadherin, (ii) a fragment of murine Lactadherin comprising a functional C1 and/or C2 domain, and, (iii) a polypeptide comprising at least 50% primary structure identity with the polypeptides of (i) or (ii). More preferably, said protein is fused to a functional C1/C2 domain.

As indicated above, the targeting moiety may be a polypeptide comprising at least 50% primary structure identity with the polypeptides of (i) or (ii) above. Identity may be determined according to various known techniques, such as by computer programs, preferably be the CLUSTAL method. More preferably, the targeting polypeptide has at least 60% identity, advantageously at least 70% identity with the polypeptides of (i) or (ii). Such Lactadherin variant (or functional equivalent) should retain the ability to target polypeptides to exosomes. This property may be verified as described in the examples, e.g., by creating a chimeric gene comprising said variant fused to a marker polypeptide, expressing the same in an exosome-producing cell and determining the presence of the marker polypeptide at the surface of the exosome. Preferred Lactadherin variants have at least 85% identity with the polypeptides of (i) or (ii) above. Possible variations include amino acid deletion(s), substitution(s), mutation(s) and/or addition(s).

The amino acid sequence of murine Lactadherin is depicted (SEQ ID No. 1; see also (12), as well as Genbank Accession no. M38337). Optionally, said Lactadherin has an amino acid sequence comprising SEQ ID No. 1 or a fragment thereof comprising a functional C1 and/or C2 domain. Preferably, said Lactadherin has an amino acid sequence comprising a functional C1/C2 domain of SEQ ID No. 1. More preferably, said Lactadherin has an amino acid sequence comprising amino acid residues 111-266, 109-266, 271-426, 111426 or 109-426 of SEQ ID No. 1.

Optionally, said exosome targeting polypeptide comprises a functional C1 and/or C2 domain of Del-1, Neuropilin-1, coagulation factor 5 or coagulator factor 8. Optionally, said antigen is fused upstream, downstream or at any internal domain junction of the targeting polypeptide.

In another particular embodiment, the exosome-producing cells and/or the exosome-targeting polypeptide (preferably the Lactadherin or a portion or variant thereof comprising a functional C1 and/or C2 domain) are from the same species as the mammal used for immunization. Indeed, in such a system, the exosomes and targeting polypeptide are not immunogenic and antibodies are produced essentially only against the selected antigen.

In a particular embodiment, the exosome-producing cells are murine cells, the Lactadherin is a murine Lactadherin or a portion or variant thereof comprising a functional C1 and/or C2 domain, the non-human mammal is a mouse, and the antigen or epitope is from a different species, for instance of human origin. Even more preferably, the mouse is a humanized mouse, allowing humanized antibodies to be produced.

To that effect, the nucleotide sequence of a protein (the antigen or an epitope) can be fused to the C1 and/or C2 domain of mouse Lactadherin and the resulting chimeric sequence is cloned into a eukaryotic expression vector using standard molecular biology techniques. Plasmids encoding the chimeric protein are transfected into an exosome-producing mouse cell line and recombinant exosomes are harvested after several days of culture of the transfected cells. Recombinant exosomes are then purified by centrifugation on a sucrose gradient (U.S. Ser. No. 09/780,748). The presence of chimeric proteins on recombinant exosomes is established by Western blot analysis or ELISA. Recombinant exosomes bearing chimeric proteins are then injected into syngeneic mice to generate antibodies. In this context, only the antigenic determinants contained in the protein sequences used to generate chimeric proteins represent foreign antigens in the immunized mice.

Alternative exosome-targeting domains can be screened, identified or selected by the method comprising:

providing a first genetic construct encoding a candidate polypeptide, preferably a candidate trans-membrane polypeptide;

introducing the first genetic construct into exosome-producing cells and testing expression of the candidate polypeptide into exosomes;

selecting a candidate polypeptide which is expressed in exosomes and preparing a second genetic construct encoding said selected polypeptide fused to a targeted polypeptide;

introducing the second genetic construct into exosome-producing cells and testing expression of the fusion polypeptide into exosomes; and selecting the polypeptide, which causes efficient expression of the targeted polypeptide into exosomes.

Our results show that different proteins or polypeptides that contain specific targeting signals directing expression on exosomes can be identified, selected and/or improved using the above methods. These polypeptides require both the ability to be expressed into exosomes and to target other molecules to such vesicles. These polypeptides may be derived from transmembrane proteins, and may include all or a portion of such proteins, typically a portion comprising at least the trans-membrane domain. These constructs are particularly suited for the delivery of antigens to exosomes, particularly receptors and trans-membrane proteins. Candidate targeting polypeptides may be derived from virtually any protein comprising such a trans-membrane domain, such as receptors, channels, etc. Specific examples of such targeting polypeptides include MelanA/MART1, CD40L, CD81, etc., or a portion thereof. The targeting polypeptide may comprise an entire trans-membrane protein, or only a portion thereof comprising at least one trans-membrane domain.

Said antigen can be any protein, for example receptors or enzymes, or compounds other than polypeptides, such as glycolipids, polysaccharides, drugs and organic chemicals. In a first embodiment, said antigens are non-characterized proteins. Antibodies against said antigens are necessary in order to identify the function of said proteins and to characterize it. Such approach is useful in the post-genomic area. Indeed, all the genomic sequences are known but it is now essential to find the function of the encoded proteins. Moreover, said antigen can be an orphan receptor. In a second embodiment, said antigen can be rare. Therefore, the preparation of antibodies against said antigen need to be very efficient. The method according to the present invention is particularly adapted to such applications.

Other examples of antigens are tumor antigens, viral antigens, and microbial antigens, for instance. Illustrative examples of tumor antigens are MAGE, BAGE, Prostate tumor antigens, oncogenes, etc. The amino acid sequence of these antigens is known per se and can, be produced by recombinant techniques or by synthesis. Particular antigens to be targeted or presented with this invention include soluble antigens and extracellular domains of receptors. Additional examples of antigens include lymphokines (IL-2, IL-4, IL-13), trophic factors (TNF, IFN, GM-CSF, G-CSF, etc.), enzymes, clotting factors, hormones, lipoproteins, etc.

A type of antigens with particular interest is a receptor having at least one trans-membrane domain, more preferably a GPCR or a portion thereof. Indeed, the invention now allows the preparation of exosomes displaying trans-membrane polypeptides with or without any exosome targeting polypeptides. The expression of GPCRs within vesicles allows their purification, characterization, the screening for ligands (whether synthetic or natural), the production of antibodies, etc. A specific example of a GPCR is, for instance, SSTR2, CCR7, CXCR4 and CCR5 although the invention can be used as well with other receptors.

In another embodiment, natural immunogenic vesicles displaying antigens containing at least one trans-membrane domain may be prepared by transfecting exosome-producing cells and over-expressing the said trans-membrane proteins. Indeed, we found that recombinant trans-membrane proteins may be transferred and expressed in exosome compartment when they are over-expressed by exosome-producing cells. This unexpected phenomenon was demonstrated for trans-membrane proteins that do not occur naturally on exosomes and appears to be restricted to specific cell lines (as described in Example 2). It is in contrast with the previous findings demonstrating that protein fusion to exosome-targeting domain is required for expression of soluble proteins or extracellular domains of receptors on exosomes. Also, in the absence of exosome-targeting signals, recombinant trans-membrane proteins are found mainly on the cell surface and only a fraction of the expressed protein is found on exosomes. The amount found on exosomes appears to be directly proportional to the amount of proteins found on the cell surface.

In yet another embodiment, the epitope profile of proteins expressed on recombinant exosome may be modified by reacting exosomes with soluble compounds. This can yield multimeric entities consisting for instances of MHC molecules loaded with a specific peptide or receptor-ligand complexes. The objective here is to generate antibodies such as restricted antibodies that react with MHC/peptide complex but not with unloaded MHC molecules. The method to load MHC molecules with peptide (Direct Loading) was recently described in WO01/82958. Restricted antibodies are sought after diagnostic and therapeutic agents as they react with markers of cancer and infected cells. In addition to classical MHC molecules, they can be raised against complexes including other polymorphic entities such as CD1 and non-classical MHC molecules. Restricted antibodies are however very difficult to obtain by classical antibody preparation methods. An example of application for restricted antibodies is the generation of compounds capable of killing HIV-infected cells. More specifically, this can be achieved by using restricted antibodies that react with HLA-C/HIV peptide complexes. Indeed, HIV has been shown to down-regulate HLA-A and B as one of the many means towards adoptive immune evasion by the virus. However, maintaining HLA-C is also crucial to virus survival as down-regulation HLA-C with A and B subtypes would trigger innate response by NK cells. Hence, it is likely that most HIV-infected cells express HLA-C/HIV peptide complexes and restricted antibodies against these flags on infected cells constitute a powerful means to eliminate HIV reservoirs in HIV patients. Therefore, the invention also concerns the use of restricted antibodies against HLA-C/HIV for the preparation of a pharmaceutical composition for treating and/or preventing HIV infection. The invention further concerns a pharmaceutical composition comprising said antibodies and a method for treating and/or preventing HIV infection in a subject comprising administering to said subject an effective amount of restricted antibodies against HLA-C/HIV.

Other examples are to generate antibodies reacting with an active form of a receptor or a ligand (triggered by conformational changes upon receptor/ligand interaction) but not the inactive form or empty receptor or ligand and reacting with a mutated form of an antigen but not with the wild type antigen. A typical example here is the preparation of neutralizing antibodies against HIV. Indeed, neutralizing epitopes have been found on HUV gp120 only when this antigen is bound to its receptors on target cells. Hence, generating receptor/ligand complexes including gp120, CXCR4 and CD4 or gp120, CCR5 and CD4 is required for raising neutralizing antibodies that inhibit receptor-mediated binding of HIV to cells. In this context, the present invention provides an efficient means to prepare appropriate immunogens comprising complex entities that are maintained in native and functional conformation and generate antibodies against specific conformational epitopes present in the complex but not on the separate entities included in it.

The generation and isolation of antibody reacting to subtle epitopes are enabled by further performing contralateral immunization and subtractive sorting of B cells as described below.

In yet another embodiment, immunogenic vesicles displaying antigens may also display adjuvant and/or ligand for specific antigen-delivery to antigen-presenting cells. This would provide further mean to increase vesicles immunogenicity, which may result in increasing the strength of the humoral responses and thereby the frequency of antigen-specific antibody producing cells. In addition, this may lower even more the amount of antigen required to induce detectable humoral responses. Vesicles with increased immunogenicity may be prepared by transfecting exosome-producing cells with plasmid encoding adjuvant fused to exosome-targeting domains such as GM-CSF/C1C2. Stable cell lines selected for optimum exosome-linked adjuvant activity may be established by standard method using drug selection and may be used as recipient for target antigen. Methods for the preparation of vesicles with increased immunogenicity and bearing chimeric adjuvants that contain exosome-targeting domains and their use have been described in WO03/016522.

Alternatively, adjuvant with trans-membrane domain may be displayed on exosomes following over-expression in exosome-producing cells as described above. The class of adjuvant containing a trans-membrane domain includes for instances CD40 ligand (CD40L), a potent immunostimulator that is produced in a trans-membrane form at the surface of CD40L-expressing cells and also as a circulating soluble form. We have found that transfection of cell lines with a plasmid encoding CD40L resulted in the expression of this adjuvant on exosomes produced by transfected cells. Such recombinant exosomes displayed increase immune potency as described in Example 4. We also found that the cleavage site of CD40L yielding the soluble form of this adjuvant may be mutated to prevent cleavage and release of soluble CD40L from exosome surface. This results in exosomes expressing the trans-membrane form of CD40L only and that display even more potent immunological activity than exosomes expressing wild type CD40L. A possible explanation for this unexpected phenomenon is that the latter contain a mixture of full-length and soluble forms of CD40L as well as residual trans-membrane domain of CD40L, which may hamper the efficacious formation of functional trimeric form of CD40L. This invention concerns an exosome comprising a CD40L mutated for the cleavage motif.

Therefore, the invention concerns a new method of expressing a polypeptide having at least one transmembrane domain at the surface of exosomes, comprising:
1) Providing a genetic construct encoding said polypeptide or a portion thereof comprising at least one transmembrane domain;
2) Introducing said construct and overexpressing said polypeptide or a portion thereof comprising at least one transmembrane domain into exosome-producing cells to generate recombinant exosomes; and
3) Collecting said recombinant exosomes, wherein said exosomes carry at their surface polypeptides encoded by said genetic construct.

In a preferred embodiment of this method, said polypeptide having at least one transmembrane domain is a receptor. More preferably, said receptor is a GPCR (G Protein-Coupled Receptor) such as SSTR2, CCR7, CXCR4 and CCR5. Alternatively, said polypeptide is a CD40L, preferably a mutated CD40L, said mutation prevents cleavage and release of soluble CD40L.

An example of ligand for specific antigen-delivery is immunoglobulin and fragment thereof, such as for instance Fc fragments of immunoglobulins. Such Fc fragments, when expressed at the surface of exosomes, can act to target the exosomes to cells expressing receptors for such Fc fragments, such as antigen-presenting cells. The expression of such Fc fragments, either alone or in combination with the expression of antigens, facilitates and enhances exosome recognition by antigen-presenting cells, particularly dendritic cells, and increases cross-priming of such antigens.

Fusions

Chimeric polypeptides or compounds can be prepared by genetic or chemical fusion.

For the genetic fusion, the region of the chimeric gene coding for the polypeptide of interest may be fused upstream, downstream or at any internal domain junction of Lactadherin or a targeting polypeptide. Furthermore, the domains may be directly fused to each other, or separated by spacer regions that do not alter the properties of the chimeric polypeptide. Such spacer regions include cloning sites, cleavage sites, flexible domains, etc. In addition, the chimeric genetic construct may further comprise a leader signal sequence to favor secretion of the encoded chimeric polypeptide into the endoplasmic reticulum of exosome-producing cells. Moreover, the chimeric gene may further comprise a tag to facilitate purification or monitoring, such as a myc tag, a poly-histidine tag, etc.

For the chemical fusion, the partial or full-length Lactadherin sequence may be selected or modified to present at its extremity a free reactive group such as thiol, amino, carboxyl group to cross-link a soluble polypeptide, a glycolipid or any small molecule. In a preferred embodiment, the Lactadherin construct encodes at least amino acids 1-271 of SEQ ID No. 1 in which the C1 domain (amino acids 111-266) provides the targeting motif to exosomes and Cysteine 271 provides the free thiol-residue for chemical cross-linking to other molecules. Cross-linking peptides, chemicals to SH group can be achieved through well-established methods (13). The advantage of this method is that it extends the scope of the invention to the preparation of antibodies to compounds other than polypeptides, such as glycolipids, drugs and organic chemicals. It also provides a means to target polypeptide and compounds to exosomes without introducing putative neo-antigenic determinants. Selected cross-linking reagents have been shown to be immunologically silent (13). Neo-antigenic determinants sometimes occur at the junction of chimeric genes and may limit the usage of chimeric gene products for specific prophylactic and therapeutic human applications. Modified exosomes or lipid vesicles (e.g., liposomes) can thus be prepared by producing exosomes (or liposomes) presenting the relevant Lactadherin construct such as SEQ ID No. 1 and then reacting them with the product to be linked. Alternatively, the Lactadherin fragment cross-linked to a product may be prepared and subsequently added to purified exosomes or liposomes.

Vectors

This invention further encompasses a vector comprising a chimeric genetic construct as described above, as well as recombinant cells comprising a chimeric genetic construct or a vector as described above. The vector may be a plasmid, a phage, a virus, an artificial chromosome, etc. Typical examples include plasmids, such as those derived from commercially available plasmids, in particular pUC, pcDNA, pBR, etc. Other preferred vectors are derived from viruses, such as replication defective retroviruses, adenoviruses, AAV, baculoviruses or vaccinia viruses. The choice of the vector may be adjusted by the skilled person depending on the recombinant host cell in which said vector should be used. In this regard, it is preferred to use vectors that can transfect or infect mammalian cells. Indeed, preferred recombinant host cells are mammalian cells. These can be primary cells or established cell lines. Mustrative examples include fibroblasts, muscle cells, hepatocytes, immune cells, etc., as well as their progenitor or precursor cells. Most preferred mammalian cells are exosome-producing mammalian cells. These include, for instance, tumor cells, dendritic cells, B and T lymphocytes or mastocytes.

Exosome-Producing Cells

Exosome-producing cells include any cell, preferably of mammalian origin, that produces and secretes membrane vesicles of endosomal origin by fusion of late endosomal multivesicular bodies with the plasma membrane (6). Cells from various tissue types have been shown to secrete exosomes, such as dendritic cells, B lymphocytes, tumor cells, T lymphocytes and mast cells, for instance. Methods of producing, purifying or using exosomes for therapeutic purposes or as research tools have been described for instance in WO99/

03499, WO00/44389, WO97/05900, incorporated therein by reference. Preferred exosome-producing cells of this invention are mammalian tumor cells, mammalian B and T lymphocytes and mammalian dendritic cells, typically of murine or human origin. In this regard, the cells are preferably immortalized dendritic cells (WO94/28113), immature dendritic cells or tumor cells (WO99/03499). Furthermore, for the production of antibody, it may be advantageous to use B lymphocytes as exosome-producing cells, since the resulting exosomes comprise accessory functions and molecules such as MHC class II molecules that facilitate antibody production. Furthermore, it has been shown that B cells-derived exosomes are able to bind to follicular dendritic cells, which is another important feature for antibody induction (14).

The cells may be cultured and maintained in any appropriate medium, such as RPMI, DMEM, AIM V etc, preferably protein-free media to avoid contamination of exosomes by media-derived proteins. The cultures may be performed in any suitable device, such as plates, dishes, tubes, flasks, etc.

The genetic construct (or vector) can be introduced into the exosome-producing cells by any conventional method, such as by naked DNA technique, cationinc lipid-mediated transfection, polymer-mediated transfection, peptide-mediated transfection, virus-mediated infection, physical or chemical agents or treatments, electroporation, etc. In this regard, it should be noted that transient transfection is sufficient to express the relevant chimeric gene so that it is not necessary to create stable cell lines. The exosomes produced by such cells may be collected and/or purified according to techniques known in the art, such as by centrifugation, chromatography, etc. Preferred techniques have been described in WO00/44389 and in U.S. Ser. No. 09/780,748, incorporated therein by reference.

Inoculums and Route of Injection

Antibodies are raised following inoculation of antigen to animals, preferably in the form of recombinant exosomes prepared as described above. Alternatively, antigens may be administered in a DNA form or in a recombinant protein form. Yet another possibility is to administer whole recombinant exosome-producing cells.

The antibodies may be polyclonal or monoclonal. Animals can be from various species, including mice, rodents, primates, horses, pigs, rabbits, poultry, etc. Preferred animals are mice.

Genetic immunization can be performed using a variety of viral vectors, such as vaccinia, poxvirus, adenovirus, adeno-associated virus, etc., non-viral vectors, such as DNA associated with various lipidic or peptidic compositions, or using pure (e.g., naked) DNA. Various vector delivery devices or techniques may be used for genetic vaccination, including gene gun or electroporation. As indicated above, the genetic construct may be any DNA or RNA molecule, typically a plasmid, viral vector, viral particle, naked DNA or any cell comprising the same. The various genetic constructs may be comprised within a single vector or in separate vectors or in any combination(s).

Protein immunization may also be used in a similar way. In this respect, recombinant chimeric antigens may be used in a purified form for administration into the animals.

Following such an administration, chimeric antigens with exosome targeting domain, preferably C1 and/or C2 domain of Lactadherin, will be loaded in vivo on the animal's own circulating exosomes, thereby inducing an immune response.

The inoculum composition generally further comprises a pharmaceutically acceptable excipient or vehicle, such as a diluent, buffer, isotonic solution, etc. The composition may also include transfection-facilitating agents, as described above for genetic immunization. The composition can further comprise an adjuvant.

Administration of inoculum can be performed by various routes, such as by systemic injection, e.g., intravenous, intra-muscular, intra-peritoneal, intra-tumoral, sub-cutaneous, intra-splenic, intra-nodal etc.

Contralateral immunization may be performed to further increase the local frequency of cells producing antibodies reacting to defined epitopes. This approach is very advantageous for the preparation and isolation of antibodies against specific epitopes found for instances on MHC/peptide complex but not on empty MHC molecules or on receptor/ligand complex but not on receptor alone. Other examples for this approach consist of epitopes found on active compounds but not the inactive form of that compound or on a mutated but not the normal form of an antigen. Contralateral immunization was first described as a mean to isolate antibody-producing cells directed against an antigen found in a mixture of proteins such as cell extracts (15). It is performed by injecting for instances the one side of an animal with a cell extract alone and then by later boosting the animal simultaneously with the cell extract alone at the same site and with the same cell extract containing a target antigen at the opposite side of the animal. The route of injection generally used for this approach is subcutaneous in the left and right footpad of an animal. In this case, antibody-producing cells are isolated from the popliteal lymph node located on the side of the animal that received the target antigen. In the present invention, contralateral immunization is applied to the preparation and isolation of epitope-specific antibodies by injecting the one side of an animal with an antigen and the other side with a conformational variant of that antigen. Conformational variant may result from protein-protein interactions, mutation/deletion or any modification of an antigen that results in the formation of neo-antigenic determinants. In this invention, contralateral immunization is best used in combination with subtractive sorting of B cells described below.

Method for Screening Antibody Repertoires

The invention now discloses a method for the screening of antibody repertoires comprising 1) contacting traceable recombinant exosomes bearing a target antigen and a marker with antibody repertoires and 2) isolating antigen-specific antibodies based on their association with the said marker via exosomes bearing antigens. Antibodies derived from cell-based library of antibody repertoire and of desired specificity may be prepared by standard antibody preparation method including recombinant DNA and hybridoma. The method is best suited for preparing antibodies from animals immunized according to the method for raising antibodies described above.

By "antibody repertoire" is intended a population of antibody-producing particles displaying different antibodies. By "antibody-producing particles" is intended a particle comprising a nucleic acid encoding an antibody displayed by the particle. Preferably said particle is a cell, a yeast, or a phage. More particularly, said antibody-producing cells can be plasma cells, hybridoma or lymphocytes. Said antibody-producing cells can also be antibody-secreting cells.

Preparation of Traceable Vesicles Displaying Antigens and a Marker

Traceable vesicles are synthetic or natural vesicles, preferably exosomes, as described above. They display the target antigen and may be detected by standard immunological, biochemical or physico-chemical methods via for instances, tags, biotin, enzymatic markers or fluorophores.

Methods for the preparation of vesicles displaying antigens have already been described above. In cases where chimeric proteins were used for immunization, a second chimeric protein is prepared where the same protein antigen sequence is fused with an extended exosome-targeting domain. Alternatively, the protein antigen may be fused to homologues of the exosome-targeting domain derived from a different species. The objective here is to create chimeric proteins with new junction sequences, thereby, avoiding the detection/selection of antibodies reacting with neo-antigenic determinant that may be found at the junction of the chimeric protein used for immunization.

Traceable exosomes may be prepared similarly to antigen-displaying exosomes, by transfecting cells with a vector encoding a marker (tags, enzyme, and fluorescent proteins for instances) fused to an exosome-targeting domain or more simply by over-expressing the marker when the latter contains a trans-membrane moiety. Exosome displaying both an antigen and a marker may be prepared using a pre-established stable cell line producing traceable exosomes only. The stable cell line used here may be any laboratory cell line generally used for its capacity to produce high amounts of recombinant proteins such as 293 cells or CHO. This cell line should preferably produce large amounts of exosomes and should also be derived from a different species than the cell line producing exosome displaying antigens used for immunization. In other terms, when the screening of antibody repertoire is performed using antibody-producing cells derived from an immunized animal, a mouse for instances, and when antibody responses in this animal were induced following immunization with mouse-cell line derived recombinant exosome, traceable exosomes displaying the target antigen and a marker used for the screening of antibody repertoire should be produced by a cell line derived from a species other than mouse. This is to avoid selecting/isolating antibodies that may have been induced against mouse-derived exosomal proteins and also to avoid the interaction of traceable exosomes with antibody-expressing cells other than via antibody-antigen interaction, through ligand-receptor for example.

In another embodiment, traceable exosomes may be prepared by conjugating active reagents to exosome such as biotin.

In another embodiment, traceable exosomes may be prepared by biosynthetic pathways using for instances labeled lipids that incorporate preferentially in endosomal vesicles including exosomes. It was recently shown that incubation of reticulocytes with the fluorophore-conjugated lipid lissamine rhodamine B dioleoyl-phosphatidyl ethanolamine (Rh-DOPE) resulted in the release of rhodamine-containing vesicles of similar density than exosomes (16). As shown in Example 6, we have found that culture of 293 cells in media supplemented with Rh-DOPE or Fluorescein-DOPE yield fluorescent 293-derived exosomes. In contrast, similar culture of dendritic cells did not yield fluorescent exosomes. This discrepancy may be explained by the different lipid composition of exosomes derived from dendritic cells and tumor cell lines.

Therefore, the invention concerns a method for preparing traceable exosomes comprising the following steps:
1) incubating exosome-producing cells with fluorophore-conjugated lipids; and,
2) producing and isolating exosomes from said cells which have incorporated said fluorophore-conjugated lipids.

Preferably, said fluorophore-conjugated lipids are fluorophore-conjugated DOPE (dioleoyl-phosphatidyl ethanolamine). More preferably, said fluorophore-conjugated DOPE is Rh-DOPE or Fluorescein-DOPE. Optionally, said exosome-producing cells are 293 cells.

Isolation of Antigen-Specific Antibodies

The isolation of antigen-specific monoclonal antibodies is performed by screening antibody repertoires in which cell-surface antibodies expressed by antibody-producing cells are contacted with traceable exosomes bearing the said antigen and a marker prepared as described above. Antibody-producing cells are preferably primary or immortalized B lymphocytes. Immortalization may result from transformation of B lymphocytes with transforming agents including viruses and oncogenes or from fusion with immortalized cells to prepare hybridoma. Antibody-producing cells may also be libraries of prokaryotic or eukaryotic recombinant cells expressing antibodies, preferably human antibodies. B lymphocytes may be derived from immunized animals, preferably transgenic animals expressing human immunoglobulins. Immunized animals may be prepared using the present invention for raising antibodies described above or with immunogens other than recombinant exosomes displaying antigens. These include commonly used antigen formulation such as purified recombinant antigens in adjuvant, nucleotide-based immunogens (naked-DNA, viral DNA) and cells or cell fractions containing antigens.

The detection and isolation of individual or population (pools of 2 or more) of antibody-expressing cells bearing traceable-exosomes may be performed using techniques known of the art and according to the nature of the antibody-expressing cells and the marker on exosomes used. For instances, a rapid and efficient method to isolate single B lymphocyte or a population of B lymphocytes contacting fluorescent exosomes is by sorting cells using a Fluorescent Activated Cell Sorter (FACS). To do so, cells from tissues or organ known to contain B lymphocytes such as blood, spleen and lymph nodes or a fraction thereof are collected from immunized animals and incubated with fluorescent recombinant exosomes bearing the antigen used for immunization. An excess of non-fluorescent parental exosomes may also be added to block binding sites other than antigen-specific sites on B lymphocytes. Fluorescent cells are then analysed by FACS and single or pools (2 or more) of fluorescent cells can be isolated by appropriately adjusting the settings of the apparatus.

In an other embodiment, cells such as plasma cells or hybridoma that do not express antibodies at their cell surface but only produce soluble antibodies that are released in the extracellular milieu may be isolated using traceable-exosomes as well. In this case, an antibody trap is formed at the cell surface to capture secreted antibodies as they are released, before incubating antibody-expressing cells with traceable-exosomes. Antibody traps may comprise for instances, a first biotinylated-antibody against a ubiquitous cell surface marker such as CD81 or CD45, Streptavidin and a second biotinylated antibody directed against immunoglobulin specific of the lymphocytes species. For example, if the antibody-producing cells are from mouse, the second biotinylated antibody is directed against mouse immunoglobulin. The trap is prepared by successfully incubating cells with the first biotinylated anti-cell surface marker antibody and Streptavidin. The remaining free biotin-binding sites on Streptavidin can then be used to bridge the surface of antibody-producing cell and an antibody-capturing moiety, i.e. the second biotinylated anti-immunoglobulin antibody. Alternatively, antibody traps can be prepared using preformed bridge containing Streptavidin bearing both biotinylated antibodies. Antibody trapping occurs during culture of cells to allow release of endogenously produced antibody and its capture at the cell surface of producing cells. The detection and isolation of individual or population (pools of 2 or more) of antibody-secreting cells may be performed using traceable-exosomes as described above. Of course, this method can also be performed with means equivalent to the couple biotin-streptavidin.

The invention also relates to the isolation of soluble antibodies that may be derived from blood of immunized animals or a fraction thereof. Soluble antibodies may also be derived from any expression system producing recombinant antibodies individually or as pools or libraries of recombinant antibodies with various antigen specificities. Here, recombinant exosomes expressing antigens are used as vehicle to isolate antibodies by a classical method of affinity-purification.

In another embodiment, the invention also relates to the isolation of epitope specific or conformation-specific antibodies. Such antibodies may react specifically to a variant form of a given antigen but not to the native form of that antigen. Variant and native antigens may be represented by mutated and wild type antigen or by antigen contacting another polypeptide, a lipid, DNA or a small molecule and free antigen. Examples of the latter are MHC/peptide complexes and unloaded MHC or MHC loaded with different peptides. A preferred MHC/peptide complex according to the present invention is the HLA-C/HIV peptide. Another class of such variants and native antigens is ligand-receptor complex and free ligand or free receptor. Preferred ligand receptor complexes according to the present invention are a gp120, CCR5, CD4 complex and a gp120, CXCR4, CD4 complex. Antigen variants may also result from physiological processes yielding non-constitutive forms of a given antigen. These include transient conformational states of antigens induced by activation/deactivation pathways involving modifying enzymes such as kinases, proteases, glycosylases and phosphatases. Isolation of epitope-specific or conformation specific antibodies may be performed by subtractive screening where a variant antigen bearing the targeted epitope is expressed on traceable exosomes and the native form of the said antigen lacking the targeted epitope is expressed on non-traceable exosomes. When added in excess to antibody-producing cells, the latter allows the blocking of binding sites on cells producing antibodies that react to common epitopes on the variant and native form of the said antigen. Hence, when traceable exosomes expressing variant antigen and an excess of non-traceable exosomes expressing native antigen are added simultaneously, cells producing antibodies directed to specific epitopes found on the variant antigen react more likely to the traceable exosomes. Thereby, epitope-specific or conformation-specific may be selectively isolated. Subtractive isolation of epitope-specific or conformation-specific antibodies is better used when antibody-producing cells are derived from immunized-animals receiving contra lateral injection as described above since the cell population collected from these animals is also enriched in epitope-specific or conformation-specific antibody-producing cells.

Production of Antigen-Specific Antibodies

The nucleotide sequences encoding at least the variable regions of heavy and light chains of immunoglobulins produced by the antibody-producing cells isolated as described above may then be cloned into expression vectors for their production as full-length or fragments of recombinant antibodies. To do this, RNA is extracted from single or pools (2 or more) of selected antibody-producing cells and nucleotide sequences encoding antibodies are amplified using standard RT-PCR methods with appropriate primers. The PCR products are then cloned into expression vectors. When only the variable regions of immunoglobulins are amplified, the cloning may be performed in a vector recipient already containing the full-length or part of the matching leader sequence and constant regions of heavy and light chains of immunoglobulin, preferably of human origin Production of recombinant antibodies or fragments thereof is then performed by transfecting cells with a mixture of DNA plasmids encoding the matching heavy and light chain of immunoglobulins. Alternatively, both chains may be cloned into a unique plasmid allowing the simultaneous expression of two gene transcripts. When heavy and light chain-PCR products are derived from more than one antibody-producing cell, a matrix of different combinations of heavy and light chain DNA plasmids may be created to reconstitute immunoglobulins with the appropriate antigen specificity. The recipient cells for expression of recombinant antibodies may be any cell line capable of producing recombinant proteins such as CHO, 293 or myeloid cell lines. Expression of recombinant immunoglobulins may be determined by standard methods such as ELISA. Antigen-specificity of recombinant immunoglobulins may also be verified by standard immunological methods according to the nature and availability of the target antigen. For instances, ELISA may be performed using recombinant exosomes expressing antigen as described above. Antibody sequences may be further manipulated by recombinant DNA techniques to increase the affinity of the antibody for its target antigen, a process known as antibody maturation, or to humanize the antibody for therapeutic applications.

In another embodiment, the invention relates to the usage of recipient vectors for the cloning of variable sequences of immunoglobulins that contain a cassette framed by two restriction sites recognized by restriction enzymes type IIs, such as BsmB I. These type IIs enzymes cut double stranded DNA outside their recognition sites, which allows insertion of DNA fragments using overlapping bases of the insert sequence, while conventional cloning uses overlapping bases of restriction sites usually added at the extremities of the insert. Hence, the invention allows cloning of variable sequences between the leader sequence and constant region of immunoglobulins without introducing mutations at the cloning sites. In contrast, most conventional cloning methods of variable sequences introduce mutation that may modify the affinity of the recombinant immunoglobulin. Example 10 further details the recipient vector and the advantages of this invention.

Therefore, the invention concerns a method of cloning of a variable sequence between the leader sequence and constant region of immunoglobulins without introducing mutations at the cloning sites comprising the steps of:
1) providing a vector containing sequentially said leader sequence, a cloning cassette framed by two restriction sites recognized by restriction enzymes type II such that the restriction sites are removed from said vector after restriction enzyme cleavage, and said constant region;
2) providing said variable sequence;
3) incubating said vector with said restriction enzyme;
4) ligating said variable sequence and said vector resulting from step 3.
5) isolating said vector comprising said variable sequence between said leader sequence and said constant sequence.

In another embodiment, isolated antibody-producing cells may be expanded in vitro by culturing them in appropriate medium. Alternatively, these cells may be immortalized by transformation or fusion as described above. Antibodies produced thereby are then purified from culture supernatants by methods known to the art such as chromatography using Protein-G beads.

In yet another embodiment, polyclonal antibodies may be purified from serum by affinity purification using for instances recombinant exosomes coupled to a solid support. Antibody bound to the solid support through antigen-specific interaction may be eluted using standard method of antibody elution, i.e. low pH.

In a more general aspect, the invention concerns a method of cloning of a sequence in a vector without introducing mutations at the cloning sites comprising the steps of:
1) providing a vector containing a cloning cassette framed by two restriction sites recognized by Type IIs restriction enzymes such that the restriction sites are removed from said vector after restriction enzyme cleavage;
2) providing said sequence with compatible extremities;
3) incubating said vector with said restriction enzyme;
4) ligating said sequence and said vector resulting from step 3.
5) isolating said vector comprising said sequence.

The following examples are offered by way of illustration and not by way of limitation.

EXAMPLE 1

Exosomes are Potent Novel Vehicle for Raising Antibodies

Nine Balb/C mice were arranged in three immunization groups of three mice. Each mouse was immunized intraperitoneally with either ~20 ng recombinant human Lactadherin in PBS (Group 1), ~20 ng recombinant human Lactadherin in a 1:1 PBS/Complete Freund's Adjuvant mix (Group 2) or recombinant WEHI exosomes containing ~20 ng human Lactadherin in PBS (Group 3).

Human recombinant Lactadherin was prepared from recombinant exosomes produced by CHO cells transfected with the plasmid pcDNA6hLactlf/His encoding the full-length recombinant human Lactadherin fused to a $(His)_6$ tag (SEQ ID No. 2). pcDNA6hLactlf/His was prepared as follows. Two overlapping fragments of human Lactadherin cDNA were amplified from hematopoietic cell-derived cDNA using primer pairs LTDNf15(SEQ ID No. 3)/LTDNr8 (SEQ ID No. 4) and LTDNf2(SEQ ID No. 5)/LTDNr13(SEQ ID No. 6), respectively. LTDN/f15 and LTDNr13 were extended at their 5' end to include a Hind III and an Age I restriction site whereas LTDNr8 and LTDNf2 included an EcoR I site. The amplification of the 3' end fragment of Lactadherin cDNA with LTDNf2/LTDNr13 yielded multiple products, the longest of which corresponding to the Lactadherin cDNA. The 5' end fragment was digested with Hind III and EcoR I whereas the 3' end fragment was digested with Age I and EcoR I. The 5' end and 3' end fragments were ligated together and into pcDNA6A-His (Invitrogen) that was precut with Hind III and Age I to yield pcDNA6hLactlf/His. This plasmid was transfected into CHO cells, a hamster ovarian cell line (ATCC) using lipofectamine (Invitrogen). At day 1 of culture in complete media (CHO-SFM supplemented with 2 mM L-glutamine, 100 U/ml Penicillin, 0.1 mg/ml Streptomycin and 2% fetal bovine serum (FBS)) at 37° C. in a 5% $CO_2$ atmosphere, stably transfected cells were selected in media supplemented with 2 μg/ml Blasticidin. After 4 days of culture, stable clones were isolated by the limiting dilution technique. Clones producing large amounts of Lactadherin were selected by Western blot analysis of recombinant Lactadherin expressed in exosomes as follows. Culture supernatants were harvested and successively spun at 200 g and filtered through a 0.2 μm filter to remove cell debris. The cleared supernatants were then spun at 4° C. for 90 min. under 100,000 g to pellet exosomes. The pellets were resuspended into 100 μl of ice-cold PBS. Eight μl of SDS-PAGE Sample Buffer 5× (SB) was added to thirty-two μl of exosome in PBS, incubated at 10° C. for 5 min. then analyzed by SDS-PAGE. Proteins on the gel were transferred to PVDF membranes following semi-dry electro-transfer. The presence of human Lactadherin in the samples was established by immunodetection using a 1/2500 dilution of polyclonal antibody directed to the RGD motif of human Lactadherin (a gift from Dr. Sebastian Amigorena). Antibody bound to Lactadherin was detected using a 1/5000 dilution of secondary anti-rabbit IgG antibody conjugated to horse-radish peroxidase (Jackson ImmunoResearch) and a colorimetric substrate (CN/DAB, Pierce). The clone CHO-3.2 was selected for production and expanded into 1-liter spinner flask in complete media without FBS for large-scale production of Lactadherin. Seven-day cell culture supernatant was transferred into 250-ml centrifuge bottles and spun 5 min at 2000 rpm to pellet cells. The supernatant was then filtered through 0.2 μm filter and concentrated to 100 ml using a fiber cartridge with a 500 KD size cut-off. Concentrated supernatant was then spun under 100,000 g for 1 hour 15 min at 4° C. The pellet containing exosome was resuspended in 1 ml MLBII (50 mM NaPO4 pH 8/300 mM NaCl/10 mM imidazole/0.5% Tween) and transferred into a tube containing 2 ml Ni-NTA slurry (prespun to remove EtOH). After an incubation of 2-3 hours at 4° C. on a shaker, the sample was poured into a BioRad column and allowed to settle at 4° C. The column was washed with 10 ml MWBI (50 mM NaPO4 pH 8/300 mM NaCl/20 mM imidazole/0.05% Tween then with 20 ml MWBII (50 mM NaPO4 pH 8/500 mM NaCl/20 mM imidazole). Proteins bound to the column were eluted with 8 ml MEBII (50 mM NaPO4 pH 8/300 mM NaCl/250 mM imidazole). Eluted proteins were concentrated and buffer was exchanged to PBS pH 7.4 using a Millipore Ultrafree-4 10,000 MWCO device. The protein sample was aliquoted and stored at −20° C. This procedure yields highly purified recombinant Lactadherin.

Exosomes derived from the mouse cell line WEHI and expressing recombinant human Lactadherin were prepared exactly as described above using CHO cell lines except that exosomes were collected after 4 days of culture of transiently transfected cells. Samples for injections in immunization group 1 to 3 were normalized for the amount of recombinant Lactadherin injected per mouse. Normalization was established by Western blot analysis as described above using serial dilutions of recombinant Lactadherin and recombinant exosomes.

Animals received one boost two weeks after the first injection with the same samples except group 2 where the antigen was resuspended in a 1:1 PBS/Incomplete Freund's Adjuvant mix. Animals were bled after the second immunization and tested for anti-human Lactadherin antibody by ELISA. For the ELISA, 50 ng human Lactadherin in PBS was coated to the wells of a microtitration plate for one hour at 37° C. Blocking buffer containing 0.05% Tween-20 and 6% Non-Fat Dry Milk in PBS was added to the wells for one hour at room temperature (RT) to saturate the remaining free binding sites. Wells were then incubated for one hour at RT with serum of immunized mice at a dilution 1/1000 in Blocking buffer. After washing the wells three times with Blocking buffer, bound antibodies were detected using a 1/10000 dilution of secondary anti-mouse IgG conjugated to horse-radish peroxidase (Jackson ImmunoResearch) and a ECL substrate (Amersham). The results of this ELISA are shown in FIG. 1.

Results: Anti-Lactadherin antibodies were detected in the serum of mice immunized with human Lactadherin-coated mouse exosomes whereas no antibody response was generated when human Lactadherin was given alone or as an emulsion in Freund's Adjuvant. No antibody was detected when using Freund's adjuvant even after four injections of the inoculum whereas the titer of antibody in serum of mice receiving Lactadherin-bearing exosomes increased with subsequent injections (data not shown).

Conclusion: Exosomes bearing antigens are highly immunogenic in the absence of any adjuvant and can induce an antibody response using very low amounts of antigens, amounts at which a classical and already potent adjuvant such as Freund's Adjuvant is inefficient. Hence, recombinant exosomes displaying antigens are powerful tools to raise antibodies against said antigens.

EXAMPLE 2

Method for the Generation of Exosomes Expressing Recombinant Membrane Proteins

The cDNA encoding the Somatostatin receptor (SSTR2), a G Protein-Coupled Receptor (GPCR), and derived from human brain RNA (Clontech, CA) was amplified by PCR using the primers SSTR2f1 (SEQ ID No. 7) and SSTR2r2 (SEQ ID No. 8). The primers contained 5' end extensions with a Hind m restriction site for SSTR2f1 and a Not I restriction site for SSTR2r2. Following digestion with Hind m and Not I, the PCR product was cloned into HApC3.1, a modified pcDNA3.1 (Invitrogen, CA) to prepare the expression vector HApC3.1/SSTR2 (SEQ ID No. 9). HApC3.1 contains a HA tag-insert (SEQ ID No. 11) that was obtained synthetically (Genset, CA) and cloned into pcDNA3.1 between the Nhe I and Hind III sites of the vector. The HA tag encodes an initiation codon followed by a stretch of codons derived from the hemagglutinin antigen sequence and HApC3.1/SSTR2 encodes HA-SSTR2, a recombinant SSTR2 with the HA tag at its N-terminal extremity (SEQ ID No. 10). HApC3.1/ SSTR2 was transfected into the mouse cell lines EL-4 and B3-Z by electroporation (under 220v, 950 microF with BioRad GenePulser electroporator). Transfected cells were cultured in selection media (RPMI 1640-2 mM Lglutamine, 100 U/ml Penicillin, 0.1 mg/ml Streptomycin, 1 mM Sodium Pyruvate and 10% fetal bovine serum (FBS)) supplemented with the antibiotic G418 (Invitrogen) at 1 mg/ml for over 7 days at 37° C. in a 5% $CO_2$ atmosphere. Cells were harvested for FACS analysis whereas culture supernatants were collected for exosome preparation. For FACS analysis, 10E6 transfected and parental cells were incubated for 1 hour at 4° C. in 1 ml PBS/5% FBS with anti-HA antibody conjugated to FITC (Roche, CA). After several washes in PBS/5% FBS cells were analyzed by FACS to evaluate the expression of HA-SSTR2 at their surface. The profile of HA-SSTR2 expression on ELA and B3-Z cells is shown FIGS. 2A and B, respectively.

Exosomes were prepared from culture supernatants as described in Example 1. Exosome production and the presence of HA-SSTR2 were determined by Western Blot analysis also as described in Example 1 using an anti-Actin (Sigma, MO) and an anti-HA antibody (HRP-conjugate, Roche, Calif.) as detecting antibodies, respectively. Exosomes from recombinant EL-4 and B3-Z were analyzed in lane 1 and 2 of FIG. 3. Detecting antibodies were anti-Actin antibody in panel A and anti-HA antibody in panel B of FIG. 3.

A panel of cDNA encoding other GPCR including CXCR4, CCR5 and CCR7 was also cloned into HApcDNA3.1 using the same cloning strategy described above for SSTR2. The primer pairs CXCR4f1 (SEQ ID No. 10)/CXCR4r2(SEQ ID No. 11), CCR5f1 (SEQ ID No. 12)/ CCR5r2(SEQ ID No. 13) and CCR7f7(SEQ ID No. 14)/ CCR7r8(SEQ ID No. 15) were used to produce PCR products encoding CXCR4, CCR5 and CCR7, respectively, using cDNA derived from human hematopoietic cell culture. The resulting plasmids HApcDNA3.1/CXCR4 (SEQ ID No. 16), HApcDNA3.1/CCR5 (SEQ ID No. 20) and HApcDNA3.1/ CCR7 (SEQ ID No. 22) encode the recombinant protein HA-CXCR4 (SEQ ID No. 19), HA-CCR5 (SEQ ID No. 21) and HA-CCR7 (SEQ ID No. 22), respectively. These plasmids as well as HApcDNA3.1/SSTR2 were transfected into the human embryonic cell line 293 cells by electroporation (220V, 950 μF on a BioRad GenePulser). Stable transfectants were established in cultures with 293-SFM media supplemented with 4 mM L-glutamine, 100 U/ml Penicillin, 0.1 mg/ml Streptomycin, 2% FBS and 250 μg/ml G418. Expression of recombinant protein containing HA tags at the cell surface and on exosomes of transfectants was monitored by FACS analysis as described above and capture ELISA, respectively. The profile of HA-GPCR expression on transfected 293 cells is shown FIG. 4. For capture ELISA, the wells of a microtitration plate were coated with 100 ng of anti-CD81 capture antibody (PharMingen) for 1 hour at 37° C. The plate was washed 3 times with 200 μL/well of PBS/ 0.05% Tween20 then incubated at room temperature (RT) for 1 hour with 200 μL/well of DPBS/1% BSA. Following a washing step, purified exosomes prepared as described in Example 1 were added to the wells. After an incubation overnight at RT with shaking, the wells were washed 3 times with washing buffer. Detecting antibody was then added to the wells and measured by subsequently adding either secondary antibody-HRP conjugates or Streptavidin-HRP when a detecting antibody conjugated to biotin is used, followed by chemiluminescent substrate (Amersham). A normalization assay was performed to quantify exosomes based on the measurement of CD81 using serial dilution of the exosome preparations and a detecting anti-CD81 antibody conjugated to HRP. A second assay was then performed to evaluate expression of recombinant antigens using equal and unsaturating amounts of exosomes and anti-HA antibody. The results of the second assay are shown FIG. 5.

Results: FIG. 2 reveals that anti-HA antibody detected specifically recombinant HA tag-containing proteins at the surface of both EL4 and B3Z transfected with HApcDNA3.1/ SSTR2 whereas this antibody did not bind to the parental EL4 and B3Z cells. HA-tag containing protein could also be detected by Western blot in exosomes derived from stably transfected EL-4 cells (FIG. 3A, lane 1) supporting that recombinant SSTR2 can be expressed on exosomes without requiring fusion to exosome-targeting domains. In contrast, the same analysis did not allow the detection of HA-SSTR2 in exosomes from stably transfected B3Z cells (FIG. 3A, lane 2). Exosome production by both cell lines was verified by Western blot analysis using an antibody against Actin, a constitutive component of exosomes (FIG. 3B, lane 1 and 2). Similar results were obtained when using an anti-SSTR2 antibody to detect HA-SSTR2 expression on cells and exosomes (data not shown).

Transfection of 293 cells with HA-pcDNA3.1/GPCR also resulted in expression of HA tag-containing protein on the cell surface of transfected cells. FIG. 4 shows the staining profile of four stable transfectants expressing HA-SSTR2, HA-CXCR4, HA-CCR5 and HA-CCR7, respectively. The mean fluorescence of the four profiles indicates that the relative levels of expression were: SSTR2> CXCR4>CCR7>CCR5. Capture ELISA revealed that, as for EL-4 cells, transfected 293 also produced exosomes bearing HA-GPCR (FIG. 5). As illustrated by the results obtained with the anti-CD81 antibody, normalized amounts of exosomes produced by the various transfectants were used. Therefore, the amounts of GPCR detected were directly proportional to the amount of GPCR expressed per exosome. Remarkably, the same ranking with regard to the relative levels of GPCR expressed at the cell surface and on exosomes was found, with SSTR2>CXCR4>CCR7>CCR5.

Conclusion: Trans-membrane proteins including GPCR that do not occur naturally on exosomes can be detected on exosomes following transfection of cells with membrane protein encoding DNA. This phenomenon does not require fusion of the trans-membrane protein sequence with exosome-targeting sequences and appears to be recipient cell-dependent. It may be due to over-expression of recombinant trans-membrane protein and could serve as an alternative pathway of secretion of excess receptors. It should be noted that only a fraction of the recombinant protein produced by transfected cells is expressed on exosomes, the bulk of the proteins being directed toward the cell surface. Regardless, this method allows expression of detectable amounts of full-length receptor on exosomes and therefore may be used for exosome display of trans-membrane proteins that otherwise are not found on exosomes or for the further enrichment of known exosomal trans-membrane proteins.

EXAMPLE 3

Method for the Generation of Exosomes Expressing Recombinant MHC I/Peptide Complex The a chain of Human Leukocyte Antigen (HLA) A201 cDNA derived from A2-positive human leucocytes by reverse transcription was amplified by PCR using the primers HLA2f1 (SEQ ID No. 17) and HLA2r2 (SEQ ID No. 18). The primers were extended at their 5' end to contain a Hind III restriction site for HLA2f1 and a BstB I restriction site for HLA2r2. The PCR product was digested with both Hind III and BstB I enzymes and ligated into pcDNA6-Myc/His that was precut with Hind III and BstBI I to yield pcDNA6-A2-Myc/His (SEQ ID No. 19).

Similarly, the β chain of HLA (β2-microglobulin or β2M) sequence was amplified by RT-PCR using the primers β2-MICf1 (SEQ ID No. 20) and β2-MICr3 (SEQ ID No. 21) and was cloned into pcDNA6-Myc/His to yield pcDNA6-β2M (SEQ ID No. 22). The β2M insert in pcDNA6-β2M was then sub-cloned into pcDNA3, which contains a different antibiotic resistance gene than pcDNA6. For this purpose, the insert was amplified with the primers β2-MICf1 and pcDNA6r4 (SEQ ID No. 23), a primer with a Not I 5' end extension. Following Hind III/Not I digestion, the PCR product was ligated into pcDNA3 precut with the same enzymes to yield pcDNA3-β2M.

The human 293 cells were transfected with both pcDNA6-A2-Myc/His and pcDNA3-β2M by electroporation as described above. Two days after transfection, cells were placed under double antibiotic selection, i.e. 2 μg/ml Blasticidin and 250 μg/ml Neomycin (G418), to establish stable double transfectant expressing both A2 and β2M. After 2 weeks under selection, a bulk population of cells was expanded to prepare exosomes as described above. Expression of human A2 and β2M on normalized exosome samples was assessed by capture-ELISA as described in Example 2. Peptide loading of HLA-A2 on 293-derived exosomes was verified using the Direct Loading method which has been shown to yield functional MHC Class I/peptide complex (WO01/82958). Briefly, samples were incubated at pH 5 with 100 μg/ml biotinylated reference Hepatitis B-peptide FLPSDCFPSV and 20 μg/ml β2M (Sigma) for 1 hour. Exosomes were then lysed in 1% NP40 and analyzed by capture-ELISA using an anti-MHC Class I antibody as capture antibody and Streptavidin-labeled Europium to detect bound biotinylated reference peptide. Results of capture ELISA measuring recombinant protein expression and peptide loading are shown FIGS. 6 and 7, respectively.

Results: Transfection of 293 cells with HLA-A2-encoding plasmid resulted in the expression of recombinant A2 in exosomes produced by transfected cells (FIG. 6). As expected, parental 293-derived exosomes also contained endogenous HIA-A2 since 293 is a human HLA-A2$^+$ cell line. However, analysis using normalized samples indicates that recombinant exosomes contained ~5 times more HLA-A2 than the parental exosomes. In contrast, the amount of β2M was similar in parental and recombinant exosomes, although the overall expression of β2M by recombinant 293 cells increased significantly (data not shown). Because the β chain of MHC Class I complex is a soluble protein, its association with exosomes is mediated through its interaction with the a chain only. Therefore our results suggest that the total amount of αβ chain complex on exosomes remains constant whereas the subtype of α chain is shifted towards recombinant HLA-A2 subtypes. As shown FIG. 7, A2-specific reference peptide could be detected on recombinant exosomes whereas measurements were only slightly above background when using parental exosomes. Background level of peptide detection in this assay was determined using exosomes produced by DC from an A2$^-$ donor (A2 negative Dex on FIG. 7). This data indicates that recombinant HLA-A2 can be loaded by A2-specific peptides using the direct loading method.

Conclusion: Transfection of exosome-producing cells with MHC Class I-encoding plasmid results in the expression of recombinant MHC Class I molecules on exosomes. This method allows the preparation of exosomes carrying a unique MHC Class I subtype. Combined with the Direct Loading method, it provides a powerful mean to produce exosomes enriched in subtype-specific MHC Class I peptide complex. These exosomes are potent vehicle for the preparation of antibodies restricted to specific MHC Class I peptide complex.

EXAMPLE 4

Method for the Generation of Enhanced Exosome Displaying CD40L Activity

Human CD40L cDNA was amplified by RT-PCR of activated-T cell RNA using primers CD40Lf8 (SEQ ID No. 24) and CD40Lr10 (SEQ ID No. 25). The primer CD40Lf8 was extended at its 5' end to include a BamH I restriction site whereas CD40Lr10 contained a BstB I 5'end extension. The PCR product was digested with BamH I and BstB I and ligated into pcDNA6-Myc/His precut with the same restriction enzymes to yield pcDNA6-CD40L (SEQ ID No. 26). The CD40L insert of pcDNA6-CD40L was then used as template to generate a 5'-end and a 3'-end overlapping fragment. The 5'-end fragment was generated using the primer CD40Lf8 and CD40Lr21 (SEQ ID No. 35) whereas the 3'-end fragment was generated using the primer CD40Lf20 (SEQ ID No. 36) and CD40Lr10. CD40Lf20 and CD40Lr21 are complementary to each other and derived from the sense and anti-sense region of CD40L that encompasses the sequence encoding residues 112 and 113 of CD40L. Proteolytic cleavage at this site mediates the release of soluble CD40L. The primers were designed to change residues 112 and 113, a Glutamic acid and Methionine in wild type CD40L, into two Glycines to produce a mutated form of CD40L that cannot be cleaved at this site and remains in its trans-membrane form. The full-length sequence encoding mutated CD40L at position 112 and 113 (mutCD40L) was generated by PCR using a mixture of 5'- and 3'-end fragments as template and the primers pair CD40Lf8/CD40Lr10. The resulting product was cloned into pcDNA6 as above to yield pcDNA6-mutCD40L (SEQ ID No. 37). pcDNA6-CD40L and pcDNA6-mutCD40L encode full-length CD40L (SEQ ID No. 34) and mutCD40L (SEQ ID No. 27), respectively. Recombinant exosomes derived from transfected 293 cells were prepared as described in Example 2 and 3. Expression of recombinant CD40L and mutated CD40L was monitored by Western Blot analysis as described in Example 1 and 2 using a rabbit anti-CD40L antibody (Santa Cruz Biotechnology) as detecting antibody. An assay was also performed to assess whether recombinant 293 acquired CD40L-like activity by stimulating dendritic cell (DC) maturation. Exosomes were normalized using the cross-capture ELISA described in Example 2 based on 1) the amount of CD81 and 2) the amount of CD40L they expressed. Normalized amounts of exosomes were added to 7-day DC cultures grown in IL4/GM-CSF-containing AIM V medium. After overnight culture, DC maturation was evaluated by measuring CD83 expression at the surface of the cells. This was achieved by standard FACS analysis as described in Example 2 using a monoclonal anti-CD83 antibody conjugated to FITC. Double staining with anti-CD83 and anti-CD86 antibodies was performed to identify the DC population (CD86-positive cells) that also expresses CD83. The results of Western blot analysis for CD40L expression and FACS analysis for DC maturation experiments are shown in FIGS. 8 and 9, respectively.

Results: Western blot analysis of recombinant exosomes revealed that transfection of 293 cells with pcDNA6-CD40L and pcDNA6-mutCD40L resulted in the expression of CD40L expression in exosomes (FIG. 8). Exosomes derived from CD40L-expressing 293 cells contained the full-length CD40L (FL on lane 2) as well as the products of its proteolytic cleavage consisting of the soluble form of CD40L (SF on lane 2) and the remaining N-terminal extremity that contains the trans-membrane domain of CD40L (TM on lane 2). In contrast, exosomes derived from mutCD40L-expressing 293 cells contained only the full-length form (FL on lane 3). No protein was detected in exosomes from parental 293 cells (lane 1).

Cell staining and FACS analysis revealed that the number of DC positives for CD83, a marker of DC maturation, increased when DC were cultured with exosomes bearing CD40L and mutCD40L whereas parental exosomes had no effect (FIG. 9). Moreover, exosomes bearing mutCD40L showed superior activity whether equal amounts of exosomes or CD40L bound to exosomes was used in the assay. Indeed, DC maturation was detected when 200 ng/ml mutCD40L bound to exosomes was used in the assay. In contrast, the same amount of CD40L bound to exosomes or soluble CD40L mixed with parental exosomes had no detectable effect. Soluble CD40L activity could be detected in the assay only for concentrations of CD40L of 1 µg/ml and above.

Conclusion: CD40L, like other trans-membrane proteins (Example 2 and 3) is expressed on exosomes following overexpression of transfected cells without requiring fusion to exosome-targeting domains. Recombinant exosomes expressing CD40L also display CD40L activity. Therefore, the present invention may be used to enhance exosome immuno-competency. A mutation in the proteolytic cleavage site of CD40L resulted in the further increase of exosome immuno-competency. A possible explanation for this property is that the wild type CD40L on exosomes consists of a mixture of full-length and soluble forms of CD40L as well as residual trans-membrane domain of CD40L, which may hamper the efficacious formation of the functional trimeric form of CD40L. In this context, preventing the cleavage of CD40L into its fragments results in the production of enhanced exosomes displaying higher specific activity. This may be required for vaccine and other research applications using recombinant exosomes since circulating proteases might cleave CD40L and inactivate exosomes shortly after injection.

EXAMPLE 5

Method for the Generation of Traceable Exosomes Using GFP/C1C2 Chimeric Protein

The cDNA encoding the fluorescent protein GFP minus the initiation codon was cloned between the leader sequence and the C1/C2 domain of Lactadherin to produce LS-GFP-C1/C2 (SEQ ID No. 40). GFP cDNA was amplified by PCR using pEGFP (Clontech, CA) as template and primers GFPf1 (SEQ ID No. 41) and GFPr2 (SEQ ID No. 42). The primer GFPf1 was extended at its 5'end to include an EcoR I restriction site whereas GFPr2 contained a Not I 5'end extension. The PCR product was digested with EcoR V and Not I and ligated to C1/C2 PCR product precut with Not I and BstB I. C1/C2 cDNA fragment was generated by PCR using pcDNA6-hLactlf/His as template and the primers LIDNf40 (SEQ ID No. 43) and LTDNr35 (SEQ ID No. 44). The ligation mix was then added to pcDNA6-hLact28-Myc/His (SEQ ID No. 45) precut with EcoR V and BstB I. pcDNA6-hLact28-Myc/His encodes the N-terminus of human Lactadherin that includes its leader sequence and EGF domain. It was prepared by ligating the product of a PCR using pcDNA6-hLactlf/His as template and the primers LTDNf15 and LTDNr28 (SEQ ID No. 46). Digesting pcDNA6-hLact28-Myc/His with EcoRV and BstB I released the DNA fragment between the Lactadherin leader sequence and the Myc/His tags which was replaced by GFP-C1/C2 DNA to produce pcDNA6-LS-GFP-C1/C2-Myc/His (SEQ ID No. 39). The control plasmid pcDNA6-LS-GFP-Myc/His (SEQ ID No. 28) encoding LS-GFP-Myc/His (SEQ ID No. 29) was also prepared using a similar approach where GFPr2 was modified to contain a BstB I extension and GFP sequence was inserted into precut pcDNA6-hLact28-Myc/His omitting the pre-ligation step with C1/C2 PCR product. Clones derived from stable cell lines transfected with the GFP plasmids were prepared, and exosomes were purified as described above for other constructions (Example 1 to 4). Exosomes were assessed for the presence of GFP on the basis of their fluorescent emission. Measurement was performed on exosomes placed in the wells of a 96-well plate and by fluorescence reading using a Wallac 1420 Victor$^2$ plate reader. The results of this measurement are shown FIG. 10.

Results: Fluorescence was detected with exosomes derived from cells transfected with pcDNA6-LS-GFP-C1/C2-Myc/His whereas background levels were read with exosomes produced by pcDNA6-LS-GFP-Myc/His-transfected cells (FIG. 10). Western blot analysis revealed that, as expected, the latter produced recombinant GFP that was released in the culture supernatant as a soluble protein (data not shown).

Conclusion: These data further confirm that fusion of sequences encoding soluble proteins to exosome-targeting domains direct expression of proteins to exosomes. Expression of GFP associated with exosomes can be used to prepare traceable tools for various applications including the sorting of antigen-specific antibody producing cells (see Example 7, below).

EXAMPLE 6

Method for the Generation of Traceable Exosomes by Metabolic Labeling Using Fluorescent Lipids In this example, traceable exosomes were prepared using fluorescent lipids that metabolically label exosomes. The lipid 1,2-Dioleoyl-sn-Glycero-3-Phosphoethanolamine-N-(Lissamine Rhodamine B Sulfonyl) (Rh-DOPE, Avanti Polar Lipids) was prepared by diluting an ethanol solution of the lipid into sterile PBS to give a final concentration of 40 μM. Incremental amounts of the 40 μM stock solution were then added to 293 cells cultures to yield 3.0 μM of the fluorescent lipid. Exosomes from day-7 culture we're harvested and purified as described in Example 14. Fluorescence associated with purified exosomes was assessed by capture-ELISA where samples were added to the well of a 96-well plate pre-coated with an anti-CD81 antibody. Following extensive washing, fluorescence emission at 600 nm upon excitation of the wells at 560 nm was read using a Wallac 1420 Victor$^2$ plate reader. Control samples for this experiment consisted of exosomes derived from fluorescent lipid-free media (Exo), exosomes derived from fluorescent lipid-free media and incubated with fluorescent lipid-containing media for 24 hours (Exo+Rh), fluorescent lipid-containing media alone (Rh) and PBS. Results are shown in FIG. 11.

Results: The production of exosomes by cells exposed to the Rh-DOPE lipid (Rh/Exo on FIG. 11) yielded highly fluorescent exosomes. In contrast, low to background levels of fluorescence were detected when exosomes were incubated directly with fluorescent lipids (Exo+Rh on FIG. 11) or when exosomes were produced in the absence of fluorescent lipid (Exo on FIG. 11). The fluorescence measured was directly associated to exosomes since only background fluorescence was detected in the assay when Rh-DOPE-containing media alone was added to the wells (Rh on FIG. 11). Production of exosomes by cells exposed to other florescent lipids such as 1,2-Dioleoyl-sn-Glycero-3-Phosphoethanolamine-N-(Carboxyfluorescein) (Fl-DOPE) also yielded highly fluorescent exosomes (data not shown).

Conclusion: The method described here results in the production of traceable exosomes. The intensity of fluorescence associated with these exosomes is far superior to that of exosomes directly labeled with florescent lipids. Their usage should allow read out in many research and screening applications with increased sensitivity. Traceable exosomes containing fluorescent lipids are, for instances, a very powerful tool to select and isolate antigen-specific antibody-producing cells (see Example 7 below).

EXAMPLE 7

Method for Identifying and Isolating Antigen-Specific B Cell

Popliteal Lymph Nodes, cells (PLNC) from mice immunized with recombinant GPCR-expressing exosomes were harvested after four successive injections of inoculum in the footpad at 1-week intervals. The inoculum consisted of purified exosomes derived from mouse cells transfected with GPCR-encoding plasmids and prepared as described in Example 2. PLNC were washed twice in PBS/5% FBS at 4° C. then two aliquots of 10E6 PLNC were resuspended into 500 μl PBS/5% FBS. Normalized amounts of GFP-expressing exosomes, GFP- and GPCR-expressing exosomes and parental exosomes were prepared as described in Example 2 and 5. An equal amount of traceable control exosomes (GFP-293) and traceable test exosomes (GFP/GPCR-293) was added to the first and second PLNC sample, respectively. A 10× excess of parental exosomes was added to both samples to block non-specific interaction of exosomes with PLNC. An anti-CD19 antibody conjugated to phycoerythrin was also added to the samples to specifically select the B cell subpopulation in PLNC. The samples were adjusted to 1 ml final with PBS/5% FBS and incubated for 1 hour at 4° C. Cells were then analyzed by FACS to identify double positives for GFP and CD19. These double positive cells are expected to be antibody producing cells, i.e. B cells, and to express antibodies at their surface that react specifically with the recombinant GPCR on GFP-exosomes. The results of an experiment performed using CCR7 as model are shown FIG. 12.

Results: The percentage of GFP-positive cells in the PLNC population derived from immunized cells was significantly higher when cells were incubated with GFP/CCR7-293 exosomes than with control GFP-293 exosomes (FIG. 12, Panel A, 0.13% positive cells vs Panel B 0.36% positive cells). Although this percentage is low, a similar trend was observed when using PLNC from mice immunized with exosomes expressing other GPCR such as CXCR4, CCR5 and SSTR2 and the matching traceable recombinant exosomes (data not shown).

Conclusion: Traceable exosomes represent a convenient tool to identify antigen-specific antibody-producing cells. Combined with FACS analysis and sorting, they should allow isolating individual cells with defined antigen specificities even at very low frequency of responding cells.

EXAMPLE 8

Subtractive Method for Identifying and Isolating B Cells Producing Epitope-Specific Antibody In this example, the sorting of antibody-producing cells is extended to epitope-specific antibody-producing cells. The method is similar to that described in Example 7 with the exception that PLNC of immunized mice are now incubated with an excess of antigen-expressing exosomes instead of parental exosomes to block B cells producing antibodies reacting with undesirable epitopes on the antigen. In such subtractive sorting, B cells reacting to neo-epitopes found on mutated antigens or conformational variants of the antigen are free to react with traceable GFP-293 expressing the antigen variant. This approach is best illustrated for the preparation of restricted antibodies that react with MHC/peptide complex. The preparation of exosomes expressing HLA-A2/peptide complex has been described in Example 3. In order to enrich the PLNC in epitope-specific antibody-producing cells, mice were immunized with recombinant exosomes using countralateral injections. Here, the right footpad of mice received six inoculums of mouse-derived exosomes expressing recombinant A2 at day −3, 0, 3, 10, 17 and 24. The left footpad received five inoculums at day 0, 3, 10, 17 and 24 of the same exosomes loaded with a MART1-derived peptide (SEQ ID No. 30). Right and left PLNC were prepared separately for staining as described in Example 7. An equal amount of traceable control exosomes (GFP/A2-293) or traceable test exosomes (GFP/A2/MART1-293) was added to both PLNC populations, respectively. A 10× excess of A2-293 was added to all samples to mask B cells producing antibody reacting with A2 alone. The results of a FACS analysis with these samples are shown FIG. 13.

Results: The percentage of GFP-positive cells in the left PLNC population derived from the side of the mice immunized with A2/MART1-exosomes was significantly higher when cells were incubated with GFP/A2/MART1-293 exosomes than with GFP/A2-293 exosomes (FIG. 13, Panel A, 0.83% positive cells vs Panel B, 0.33% positive cells). In contrast, no significant difference could be detected when comparing the right PLNC incubated with GFP/A2/MART1-293 and GFP/A2-293 (FIG. 13, Panel C, 0.49% positive cells vs Panel D, 0.39% positive cells).

Conclusion: The subtractive method that uses traceable exosomes described here is a powerful approach to identify epitope-specific antibody-producing cells. Combined with FACS analysis and sorting, it enables isolation of individual cells with defined epitope specificities. Subtractive sorting is amenable, for instances, to isolating B cells producing restricted antibodies that react with MHC/peptide complex.

EXAMPLE 9

Method for Retrieving Immunoglobulin Sequences by RT-PCR

Cells producing antibodies with defined antigen or epitope specificities and identified by FACS as described in Example 7 and 8, were sorted individually in the wells of a 96-well plate containing 25 μl of ice-cold lysis buffer (Cells to cDNA II kit, Ambion). RNases were heat-inactivated by incubating the 96-well plate at 75° C. for 15 minutes. Samples were then treated with 1 Unit of DNase I to eliminate genomic DNA. The resulting samples contained RNA that was transferred into a new plate for cDNA synthesis using Reverse Transcriptase and oligo-dT (SuperScript II, Invitrogen). cDNA encoding the variable region of the light and heavy chains of immunoglobulins that contains the complementary determinant regions involved in contacting antigens was amplified by nested-PCR. A mixture of forward primers including IGLKf1 (SEQ ID No. 31), IGLKf2 (SEQ ID No. 32), IGLKf3 (SEQ ID No. 33), IGLKf4 (SEQ ID No. 34), IGLKf5 (SEQ ID No. 35) and the reverse primer IGKr15 (SEQ ID No. 36) were used for a first round PCR of light chain sequences. A second round PCR (nested-PCR) was performed using an aliquot of the first round PCR as template and the degenerated primers IGKf6 (SEQ ID No. 37) and IGKr15. Similarly, a mixture of forward primer including IGLHf1 (SEQ D No. 38), IGLHf2 (SEQ ID No. 39) and IGLHf3 (SEQ ID No. 40) and the reverse primer IGHr5 (SEQ ID No. 41) were used for a first round PCR of heavy chain sequences. A second round PCR (nested-PCR) was performed using an aliquot of the first round PCR as template and the degenerated primers IGHf11 (SEQ ID No. 42) and IGHr13 (SEQ ID No. 43). The results of amplification of light chain sequences using cDNA from cells sorted individually based on their ability to bind fluorescent exosomes in an antigen-specific manner is shown FIG. 14.

Results: Two rounds of PCR yielded detectable amounts of PCR products derived from several single cell cDNA (FIG. 14, lane 2, 5, 6, 8 and 13). Sequencing of these PCR products confirmed that they encode the variable regions of immunoglobulins. Several possibilities may explain the lack of PCR products in the empty lanes of FIG. 14. One possibility is that the PCR cycling conditions and primer pairs used here were not optimum to amplify efficiently the variable sequences of immunoglobulin expressed by the single cell of the original well. Indeed, every variable region is unique and may require different PCR conditions for amplification. Other primer combinations and cycling conditions may be tried with each cDNA for optimum results. Another possibility is that the cell sorted in the original well was a non-B cell or a resting B cell. These cells which can be sorted due to non-specific interactions of traceable exosomes with PLNC (see background staining in Example 7 and 8) contain no or too low levels of RNA encoding immunoglobulins for detection by RT-PCR. This emphasizes that the sensitivity of the method proposed here to retrieve variable sequences of immunoglobulin may avoid the further carry over of cDNA from non-antibody-producing cells.

Conclusion: Variable sequences of immunoglobulin from single cells isolated based on their ability to interact with traceable exosomes in an antigen-specific manner can successfully be retrieved by classical RT-PCR. The PCR products can then be cloned into expression vectors as described in Example 10, below.

EXAMPLE 10

Method for Cloning of Variable Sequences of Immunoglobulins into Expression Vectors Expression vectors were constructed with embedded portions of heavy and light chain antibody sequences to receive the variable region PCR products generated in Example 9. Cloning of variable region PCR products in these vectors yields full-length heavy and light chain sequences. Unlike classical methods of insert cloning, the cloning strategy used here does not introduce mutations at the cloning sites. This method is advantageous since mutations at either extremity of the variable region of immunoglobulins may modify antigen affinity and specificity. It uses type "IIs" restriction enzymes such as BfuAI, BsaI and BsmBI that cut outside the sequence recognition site, leaving the recognition sequence on one side of the cut. A cassette containing two such restriction sites allows the release of inserts framed by the two sites, leaving only the embedded antibody sequence. Inserts for cloning are generated to include similar sites at both ends with sequence extremities compatible to the embedded antibody sequence. Thereby, ligation of inserts occurs via annealing of gene-specific sequences without the need to insert or modify bases matching the recognition sites of restriction enzymes.

Separate vectors were constructed for antibody heavy and light chains. These contained the leader sequence and constant regions of a prototypical heavy and light chain, respectively, flanking a linker-free cloning cassette. Mouse spleen cDNA encoding light chain sequences was amplified to generate an upstream leader sequence fragment using primers IGKf1 (SEQ ID No. 44) and IGKr2 (SEQ ID No. 45) and a downstream constant region fragment using primers IGKf12 (SEQ ID No. 46) and IGKr4 (SEQ ID No. 47). IGKr2 and IGKf12 were designed to contain overlapping sequences encompassing the linker-free cloning cassette. The complete DNA fragment including leader sequence, linker-free cloning cassette and constant region was generated by a second PCR using the upstream and downstream fragments as template and primers IGKf1 and IGKr4. These primers contained 5' end extensions with a Hind III restriction site for IGKf1 and a BstB I for IGKr4. Following digestion with Hind III and BstB I, the PCR product was cloned into pcDNA6-Myc/His precut with the same enzymes yielding pcDNA6-LCJ-Myc/His (SEQ ID No. 48). pcDNA6-HCJ-Myc/His (SEQ ID No. 49) encoding the heavy chain equivalent of pcDNA6-LCJ-Myc/His was prepared using the same approach. Here, the first round of PCR was performed with primer pairs IGHf1 (SEQ ID No. 50)/IGHr2(SEQ ID No. 51) and IGHf15(SEQ ID No. 52)/IGHr4(SEQ ID No. 53). The second round PCR was performed with IGHf1 and IGHr4.

Another construction was prepared to express the heavy and light chains of antibody in a single vector. This is to ensure that any transfected cell produces both the heavy and light chains. For this purpose, an internal nbosome entry site (IRES) and a second multiple cloning site (mcs2) derived from pIRES (Clontech) was cloned downstream of LCJ in pcDNA6-LCJ-Myc/His. The IRES/mcs2 insert was generated by PCR using pIRES as template and primer pIRf1(SEQ ID No. 54) and pIRr2 (SEQ ID No. 55). After digestion with BstBI and Age I, the PCR product was ligated into pcDNA6-LCJ-Myc/His precut with the same enzymes, yielding pcDNA6-LCJ-IRES. The cloning of heavy and light chain variable regions into pcDNA6-LCJ-IRES was then performed in two steps. First, the light and heavy chains was cloned into pcDNA6-LCJ-IRES and pcDNA6-HCJ-Myc/His, respectively. Second, the full-length heavy chain prepared in the first step in pcDNA6-HCJ-Myc/His was sub-cloned into pcDNA6-L-IRES also prepared in the first step and already encoding the full-length light chain.

An experiment was performed to verify that the PCR products generated in Example 9 and cloned into expression vectors using the method described here yielded immunoglobulins. The PCR products HV-M90/12 (SEQ ID No. 56) and LV-M90/12 (SEQ ID No. 57) encoding the variable regions of heavy and light chains sequences, respectively, derived from a single cell isolated as described in Example 8 were used as model. BsmB I restriction sites were introduced at the extremities of each DNA fragment by a 10-cycle PCR using primers IGKf6 and a 1:1 mix of IGKr10(SEQ ID No. 58): IGKr11 (SEQ ID No. 59) for LV-M90112 and primers IGHf11 and a 1:1:1 mix of IGHr16(SEQ ID No. 60)/IGHr17 (SEQ ID No. 61)/IGHr18(SEQ ID No. 62) for HV-M90/12. These primers were designed to leave overhang extremities complementary to the junctions of the embedded antibody sequences in the recipient expression vectors. Following digestion with BsmB I, LV-M90/12 was cloned into pcDNA6-LCJ-IRES and pcDNA6-LCJ-Myc/His precut with the same enzyme yielding pcDNA6-L-M90/12-IRES (SEQ ID No. 63) and pcDNA6-L-M90/12-Myc/His (SEQ ID No. 64), respectively. HV-M90/12 was first cloned into pcDNA6-HCJ-Myc/His precut with BsmB I yielding pcDNA6-H-M90/12-Myc/His (SEQ ID No. 65). The full-length H-M90/12 heavy chain sequence was then sub-cloned into mcs2 of pcDNA6-L-M90/12-IRES. To do so, Xba I and Not I restriction sites were introduced by PCR at the 5' and 3' end, respectively, of H-M90/12 using pcDNA6-H-M90/12-Myc/His as template and the primers pIRHf1 (SEQ ID No. 66) and pIRHr2 (SEQ ID No. 67). Following digestion with Xba I and Not I, H-M90/12 was cloned into pcDNA6-L-M90/12-IRES precut with the same enzymes yielding pcDNA6-L+H-M90/12. CHO cells were transfected with either empty plasmid, pcDNA6-L+H-M90/12 or a 1:1 mix of pcDNA6-L-M90/12-Myc/His: pcDNA6-H-M90/12-Myc/His. Day-3 culture supernatants were harvested and tested for immunoglobulin production by capture-ELISA as described in Example 2 using a donkey anti mouse IgG antibody (Jackson ImmunoResearch) as capture antibody and a rabbit anti-mouse IgG as detecting antibody. A standard curve was established using incremental amounts of purified mouse IgG. The results of this ELISA are shown FIG. 15.

Results: Recombinant immunoglobulins were successfully detected in the supernatant of CHO-transfected cells (FIG. 15). Moreover, transfection with expression vector encoding both light and heavy chains of antibodies was superior to co-transfection with plasmids encoding each chain separately.

Conclusion: The cloning strategy for the construction of plasmids encoding full-length immunoglobulin described here yields expression vectors producing significant amounts of recombinant immunoglobulins without introducing insertion or mutations in the variable regions of the antibody produced. Overall, Example 7 to 10 support that antibody sequences derived from individual cells producing antibodies with defined specificity can be retrieved, cloned and expressed as recombinant proteins using the methods described in this invention. The antigen specificity of the recombinant antibody produced can then be evaluated in binding assays, preferably using recombinant exosomes as source of antigen.

EXAMPLE 11

Isolation of Antibody-Secreting Hybridoma Using Biotinylated Exosomes

Spleen cells of mice immunized as described in Example 8 were fused with the mouse myeloma cell line Sp2/0 using standard method of hybridoma preparation. Following fusion, cells were grown as a bulk-culture in media supplemented with Azaserine for selection of hybridoma. At day-8 of the culture, cells were harvested and incubated successively with biotinylated anti-CD45 antibody and Streptavidin. Cells were then separated into two equal fractions, i.e. antibody-trap positive (AbTrap+) and negative (AbTrap−) fractions. The antibody trap of the AbTrap+ fraction was completed by incubating cells with biotinylated anti-mouse IgG antibody. Both cell fractions were then incubated overnight in culture media at 37° C. under a 10% $CO_2$ atmosphere to allow hybridoma antibody secretion and capture by the antibody trap. Hybridoma secreting antibodies that were trapped at their cell surface and displayed desired antigen specificities were isolated by FACS following incubation with biotinylated exosomes. These traceable exosomes were prepared by incubating exosomes with chemically reactive biotin bearing tetrafluorophenol (TFP) conjugated to biotin via a polyethylene oxide (PEO) linker. TFP activated biotin reacts with primary amines on exosomes to form a covalent linkage. Hybridroma bearing biotinylated exosomes at their surfaces were detected using Streptavidin conjugated to the fluorophore Alexa488. FACS analysis of AbTrap + and − hybridoma producing anti-exosome antibodies is shown FIG. 16.

Results: Incubation of biotinylated-exosomes with AbTrap− cells resulted in background fluorescence associated with these cells (FIG. 16, panel 1). In contrast, ~25% of these cells were positive when bearing the full AbTrap (FIG. 16, panel 2).

Conclusion: The antibody trap designed here successfully captured antibodies secreted by hybridoma, which enable hybridoma isolation by FACS. In addition, these results show that biotinylated exosomes are suitable traceable exosomes to isolate antibody-producing cells in an antigen-specific manner.

REFERENCES

1. Vaitukaitis J, Robbins J B, Nieschlag E and Ross G T.
   A method for producing specific antisera with small doses of immunogen.
   J CLIN ENDOCRINOL METAB. 33(6), 988-91, 1971.

2. Kohler G and Milstein C.
   Continuous cultures of fused cells secreting antibody of predefined specificity.
   NATURE. 256, 495-7, 1975.
3. Harlow E and Lane D.
   Antibodies: A laboratory manual
   COLD SPRING HARBOR LABORATORY, 1988
4. Babcook, J. S.; Leslie, K. B.; Olsen, O. A.; Salmon, R. A. and Schrader, J. W.
   A novel strategy for generating monoclonal antibodies from single, isolated lymphocytes producing antibodies of defined specificities
   PROC. NATL. ACAD. SCI. U.S.A 93, 7843-48, 1996
5. Rader C. and Barbas C. F.
   Phage display of combinatorial antibody libraries
   CURR. OPIN. BIOTECHNOL. 8,503-508, 1997.
6. Garin, J., Diez, R., Kieffer, S., Dermine, J. F., Duclos, S., Gagnon, E., Sadoul, R., Rondeau, C. and Desjardins, M.
   The phagosome proteome: insight into phagosome functions.
   J CELL BIOL 152, 165-80., 2001
7. Thery C., Zitvogel L. and Amigorena S.
   Exosomes: Composition, Biogenesis and Function.
   NATURE REVIEW 2 (2002) 569
8. Thery, C., Regnault, A., Garin, J., Wolfers, J., Zitvogel, L., Ricciardi-Castagnoli, P., Raposo, G. and Amigorena, S.
   Molecular characterization of dendritic cell-derived exosomes. Selective accumulation of the heat shock protein hsc73.
   J CELL BIOL 147, 599-610, 1999
9. Thery, C., Boussac, M., Veron, P., Ricciardi-Castagnoli, P., Raposo, G., Garin, J. and Amigorena, S.
   Proteomic analysis of dendritic cell-derived exosomes: a secreted-subcellular compartment distinct from apoptotic vesicles.
   J IMMUNOL 166, 7309-18., 2001
10. Wolfers, J., Lozier, A., Raposo, G., Regnault, A., Thery, C., Masurier, C., Flament, C., Pouzieux, S., Faure, F., Tursz, T., Angevin, E., Amigorena, S. and Zitvogel, L.
    Tumor-derived exosomes are a source of shared tumor rejection antigens for CTL cross-priming.
    NAT MED 7, 297-303., 2001
11. Zitvogel, L., Regnault, A., Lozier, A., Wolfers, J., Flament, C., Tenza, D., Ricciardi-Castagnoli, P., Raposo, G. and Amigorena, S.
    Eradication of established murine tumors using a novel cell-free vaccine: dendritic cell-derived exosomes.
    NAT MED 4, 594-600, 1998
12 Stubbs J D, Lekutis C, Singer K L, Bui A, Yuzuki D, Srinivasan U and Parry G.
    cDNA cloning of a mouse mammary epithelial cell surface protein reveals the existence of epidermal growth factor-like domains linked to factor VIII-like sequences.
    PROC NATL ACAD SCI USA. 87, 8417-21, 1990.
13 Hermanson, G T
    Bioconjugate Techniques
    SAN DIEGO ACADEMIC PRESS, 758 pages, 1996
14 Denzer, K, van Eijk, M, Kleijmeer, M J, Jakobson, E, de Groot, C and Geuze, H J.
    Follicular Dendritic Cells carry MHC Class II-Expressing Microvesicles at Their Surface.
    J. IMMUNOL. 165, 1259-1265, 2000.
15 Yin, A H, Miraglia, S, Zanjani, E D, Almeida-Porada, G, Ogawa, M, Leary, A G, Olweus, J, Kearney, J and Buck, D W.
    AC133, a novel marker for human hematopoietic stem and progenitor cells.
    BLOOD 90, 5002-12, 1997.
16 Vidal, M, Mangeat, P and Hoekstra, D.
    Aggregation reroutes molecules from a recycling to a vesicle-mediated secretion pathway during reticulocyte maturation.
    JOURNAL OF CELL SCIENCE 110, 1867-1877, 1997.

The invention claimed is:

1. A method of isolating single antibody-producing particles having specificity for a selected antigen, comprising:
   1) preparing exosomes displaying a selected antigen and a marker, said antigen being fused to an exosome targeting polypeptide, and said exosome targeting polypeptide being a partial murine lactadherin sequence selected from the group consisting of amino acid residues 111-266, 109-266, 271-426, 111-426 and 109-426 of SEQ ID NO: 1;
   2) contacting said exosomes of step 1 with an antibody-producing particles repertoire; and,
   3) identifying and isolating single antibody-producing particles reacting with said exosomes.

2. The method of claim 1, wherein said antibody-producing particles are antibody-producing cells and wherein said antibody-producing particles repertoire is a repertoire of antibody-producing cells.

3. The method according to claim 2, wherein said antibody-producing cells are selected from the group consisting of plasma cells, hybridoma and lymphocytes.

4. The method according to claim 1, wherein said method comprises:
   1) providing antibody-producing cells;
   2) preparing exosomes displaying said antigen and a marker;
   3) suspending the antibody-producing cells of step 1 with the exosomes of step 2; and,
   4) identifying and isolating single antibody-producing cells reacting with said exosomes.

5. The method according to claim 4, wherein said antibody-producing cells are lymphocytes collected from non-human animals immunized with said antigen.

6. The method according to claim 1, wherein said method comprises:
   1) providing antibody-producing cells;
   2) preparing the exosomes displaying said antigen and said marker;
   3) suspending the antibody-producing cells of step 1 with the exosomes of step 2; and,
   4) identifying and isolating single antibody-producing cells reacting with said exosomes; and wherein said antibody-producing cells are antibody-secreting cells and the method further comprises, before the step of suspending the antibody-secreting cells with the exosomes, the step of incubating antibody-producing cells with a first biotinylated-antibody against a ubiquitous cell surface marker, streptavidin and a second biotinylated antibody directed against immunoglobulin of said antibody-producing cells.

7. A method of isolating single antibody-producing cells having specificity for a selected antigen, comprising:
   1) preparing immunogenic exosomes displaying at least one antigen or an epitope thereof, said antigen or said epitope being fused to an exosome targeting polypeptide, and said exosome targeting polypeptide being a partial murine lactadherin sequence selected from the group consisting of amino acid residues 111-266, 109-266, 271-426, 111-426 and 109-426 of SEQ ID NO: 1;
   2) raising an antibody response by immunizing a non-human animal with said immunogenic exosomes;
   3) collecting lymphocytes from said immunized animal;
   4) preparing exosomes displaying the said antigen or an epitope thereof of step 1 and a marker;
   5) suspending the lymphocytes of step 3 with the exosomes of step 4; and,
   6) identifying and isolating single antibody-producing cells reacting with the exosomes of step 4.

8. The method of claim 1, wherein said antibody-producing particles are antibody-producing phages or yeasts and wherein said antibody-producing particles repertoire is a repertoire of antibody-producing phages or yeasts.

9. The method according to claim 1 wherein said method further comprises the following steps: a) recovering DNA or RNA from said selected antibody producing particles, b) amplifying the nucleic acid sequence encoding immunoglobulin sequences or portions thereof, c) cloning the amplified nucleic acid sequence into an expression vector to produce proteins with desired antigen specificity.

10. The method according to claim 7, wherein said immunogenic exosomes further display immune accessory molecules.

11. The method according to claim 10, wherein said immune accessory molecule is an adjuvant polypeptide.

12. The method according to claim 10, wherein said immune accessory molecules are fused or cross-linked to an exosome targeting polypeptide.

13. The method according to claim 10, wherein said immune accessory molecules have at least one transmembrane domain and are incorporated into immunogenic exosomes by over expression into the exosome-producing cells.

14. A method of isolating particles producing a single antibody specific for a variant antigen from an antibody-producing particles repertoire comprising:
  1) preparing a first population of exosomes displaying said variant antigen and a marker, said variant antigen being fused to an exosome targeting polypeptide, and said exosome targeting polypeptide being a partial murine lactadherin sequence selected from the group consisting of amino acid residues 111-266, 109-266, 271-426, 111-426 and 109-426 of SEQ ID NO: 1;
  2) preparing a second population of exosomes displaying the wild-type antigen and not displaying said marker, said wild-type antigen being fused to an exosome targeting polypeptide, and said exosome targeting polypeptide being a partial murine lactadherin sequence selected from the group consisting of amino acid residues 111-266, 109-266, 271-426, 111-426 and 109-426 of SEQ ID NO: 1;
  3) suspending said antibody-producing particles repertoire with the first and second populations of exosomes, the second population being in excess; and,
  4) identifying and isolating single antibody-producing particles reacting with the exosomes of step 1.

15. The method according to claim 14, wherein said method comprises:
  1) collecting lymphocytes from a non-human animal immunized with said variant antigen;
  2) preparing exosomes displaying said variant antigen used for the animal immunization and said marker;
  3) preparing exosomes displaying the wild-type antigen and not displaying said marker;
  4) suspending the lymphocytes of step 1 with the exosomes displaying said variant antigen and marker of step 2 and with an excess of the exosomes displaying said wild-type antigen of step 3; and,
  5) identifying and isolating single antibody-producing cells reacting with the exosomes of step 2.

16. A method of isolating cells producing a single antibody specific for a variant antigen from an antibody-producing particles repertoire comprising:
  1) preparing immunogenic exosomes displaying a variant antigen, said variant antigen being fused to an exosome targeting polypeptide, and said exosome targeting polypeptide being a partial murine lactadherin sequence selected from the group consisting of amino acid residues 111-266, 109-266, 271-426, 111-426 and 109-426 of SEQ ID NO: 1;
  2) raising an antibody response by immunizing a non-human animal with the said immunogenic exosomes;
  3) collecting lymphocytes from said immunized animal;
  4) preparing exosomes displaying said variant antigen of step 1 and a marker;
  5) preparing exosomes displaying the wild-type antigen and not displaying said marker;
  6) suspending the lymphocytes of step 3 with the exosomes displaying said variant antigen and marker of step 4 and with an excess of the exosomes displaying said wild-type antigen of step 5; and,
  7) identifying and isolating cells producing a single antibody specific for a variant antigen reacting with the exosomes of step 4.

17. The method according to claim 14, wherein said variant antigen is a mutated antigen.

18. The method according to claim 14, wherein said variant and wild-type antigens are different conformational states of any protein, including an enzyme.

19. The method according to claim 1, wherein said marker is a detectable molecule selected from tags, biotin, enzyme, and fluorescent molecules.

20. The method according to claim 19, wherein said marker is fused or cross-linked to an exosome targeting polypeptide.

21. The method according to claim 19, wherein said marker has a transmembrane domain incorporated into immunogenic exosomes by over expression into exosome-producing cells.

22. The method according to claim 19, wherein said marker is a labeled lipid.

23. The method according to claim 22, wherein said labeled lipids are fluorophore-conjugated lipids.

24. The method according to claim 1, wherein said antigen is a receptor.

25. The method according to claim 24, wherein said receptor is a GPCR (G Protein-Coupled Receptor).

26. The method according to claim 1, wherein said antigen is any protein or compounds other than polypeptides.

27. The method according to claim 11, wherein said adjuvant polypeptide is a cytokine.

28. The method of claim 27 wherein said cytokine is selected from the group consisting of GM-CSF, IL-2 and CD40L.

29. The method of claim 27 wherein cytokine is a mutated CD40L.

30. The method of claim 29 wherein said mutated CD40L contains a mutation which prevents cleavage and release of soluble CD40L.

31. The method according to claim 22, wherein said labeled lipid is incorporated in an exosome.

32. The method according to claim 26, wherein said protein is a receptor or an enzyme, and said compounds other than polypeptides are glycolipids, polysaccharides, drugs or organic chemicals.

* * * * *